United States Patent
Baubet et al.

(10) Patent No.: US 7,763,443 B2
(45) Date of Patent: Jul. 27, 2010

(54) POLYNUCLEOTIDES ENCODING CHIMERIC GFP-AEQUORIN AS BIOLUMINESCENT CA++ REPORTERS

(75) Inventors: Valérie Baubet, Kansas City, MO (US); Hervé Le Mouellic, Paris (FR); Philippe Brulet, Paris (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 1395 days.

(21) Appl. No.: 11/149,177

(22) Filed: Jun. 10, 2005

(65) Prior Publication Data

US 2008/0213879 A1   Sep. 4, 2008

Related U.S. Application Data

(60) Division of application No. 10/307,389, filed on Dec. 2, 2002, now Pat. No. 6,936,475, which is a continuation of application No. PCT/EP01/07057, filed on Jun. 1, 2001.

(60) Provisional application No. 60/255,111, filed on Dec. 14, 2000, provisional application No. 60/210,526, filed on Jun. 9, 2000, provisional application No. 60/208,314, filed on Jun. 1, 2000.

(51) Int. Cl.
*C12P 21/06* (2006.01)
(52) U.S. Cl. .................. 435/69.1; 435/320.1; 435/6; 435/7.1; 530/350
(58) Field of Classification Search ............. None
See application file for complete search history.

(56) References Cited

U.S. PATENT DOCUMENTS 5,498,521 A * 3/1996 Dryja et al. .................. 435/6

6,800,492 B2   10/2004  Baubet et al. ............... 436/182
6,936,475 B2    8/2005  Baubet et al. ............... 436/182

OTHER PUBLICATIONS

Baubet et al., Chimeric green flourescent protein-aequorin as bioluminescent $Ca^{2+}$ reporters at the single-cell level. Proc. Nat'l Acad. Sci., vol. 97, pp. 7260-7265 (2000).
Chiesa et al. Recombinant aequorin and green flourescent protein as valuable tools in the study of cell signalling. Biochem. J., vol. 355, pp. 1-12 (2001).
Miyawaki et al. Dynamic and quantitative $Ca^{2+}$ measurements using improved cameleons, Proc. Nat'l Acad. Sci., vol. 96, pp. 2135-2140 (1999).
Miyawaki et al., Fourescent indicators for $Ca^{2+}$ based on green flourescent proteins and calmodulin. Nature, vol. 388, pp. 882-887 (1997).
Pinton et al., New light on mitochondrial calcium, BioFactors, vol. 8, pp. 243-253 (1998).
Rutter et al. Subcellular imaging of intramitochondrial $Ca^{2+}$ with recombinant targeted aequorin: Significance for the regulation of pyruvate dehydrogenase activity. Proc. Nat'l Acad. Sci., vol. 93, pp. 5489-5494 (1996).
Campbell et al., "Chemiluminescence Energy Transfer," *Principles and Application in Biology and Medicine*, eds. pp. 474-534 (1988).
Campbell et al., "Luminescence in Cells and Vesicles Isolated from the Hydroid Obelia Geniculata," *Proc. Physiol. Soc.*, vol. 287, pp. 4-5 (1978).

* cited by examiner

*Primary Examiner*—Hope A Robinson
(74) *Attorney, Agent, or Firm*—Finnegan, Henderson, Farabow, Garrett & Dunner, LLP

(57) ABSTRACT

A modified bioluminescent system comprising a fluorescent molecule covalently linked with a photoprotein, wherein said link between the two proteins has the function to stabilize the modified bioluminescent system and allowing the transfer of the energy by Chemiluminescence Resonance Energy Transfer(CRET).

22 Claims, 14 Drawing Sheets

A.1
CaCl₂
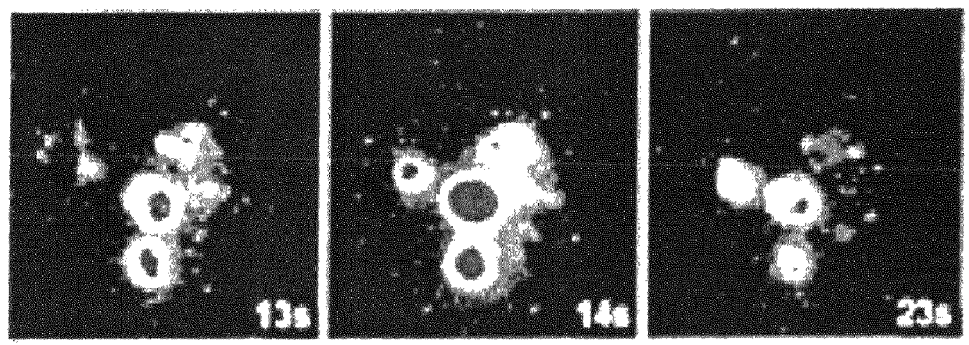
FIG. 4A.1
A23187
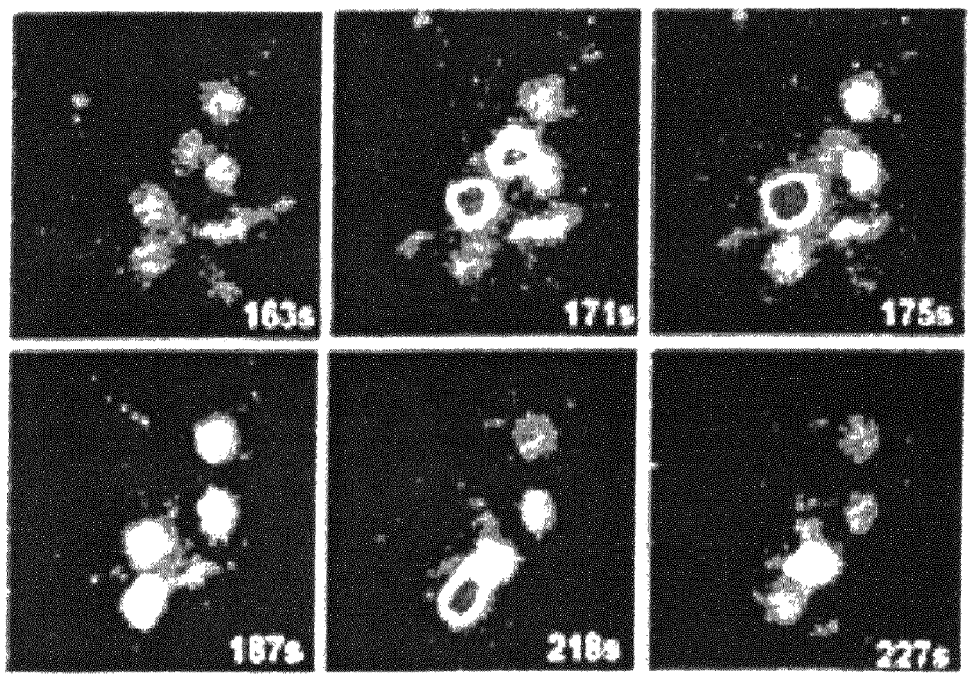
FIG. 4A.2

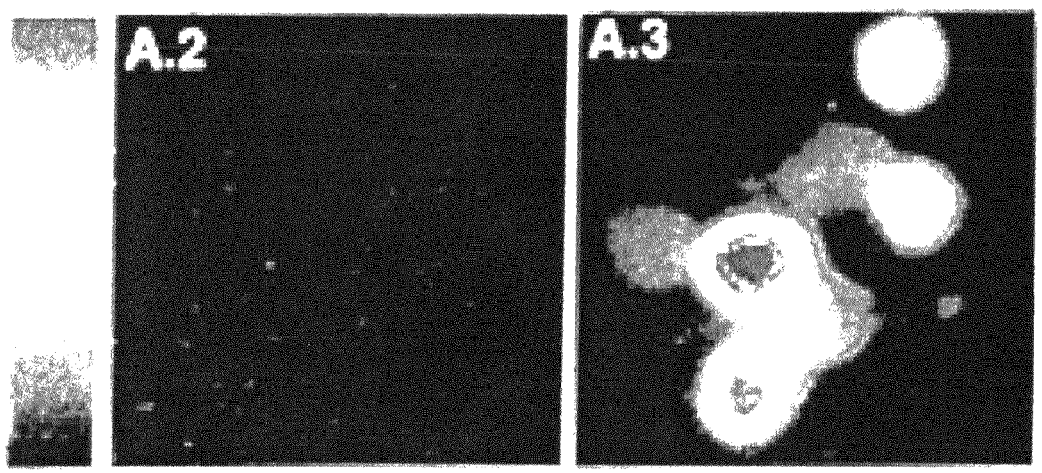
FIG. 4A.3

Fluorescence and Ca2+-induced bioluminescent activity in dissociated neurons in culture infected with adenoviral-G5A vectors.

Fluorescence and Ca2+-induced bioluminescent activities
in dissociated neurons in culture infected with adenoviral-SG5A vectors.

POLYNUCLEOTIDES ENCODING CHIMERIC GFP-AEQUORIN AS BIOLUMINESCENT CA++ REPORTERS

CROSS-REFERENCE TO RELATED APPLICATIONS

This is a division of application Ser. No. 10/307,389, filed Dec. 2, 2002, now U.S. Pat. No. 6,936,475 which is a Continuation of International Application No. PCT/EP01/07057, filed Jun. 1, 2001, which claims the benefit of U.S. Provisional Application Nos. 60/255,111, filed Dec. 14, 2000; 60/210,526, filed Jun. 9, 2000; and 60/208,314, filed Jun. 1, 2000; all pending, all of which are incorporated herein by reference.

BACKGROUND OF THE INVENTION

This invention relates to a modified bioluminescent system comprising a flourescent molecule covalently linked with a photoprotein allowing the transfer of energy by Chemiluminescence Resonance Energy Transfer (CRET). This invention also relates to the use of the modified bioluminescent system in in vivo and in vitro assays.

Calcium is implicated in the regulation of a great variety of intracellular processes (1). Several techniques are most commonly used for intracellular $Ca^{++}$ monitoring. Patch-clamp and $Ca^{++}$ selective microelectrodes give cumulative measurements of CaH fluxes in a restricted number of cells. On the other hand, intracellular $[Ca^{++}]$ dynamics in large populations of cells can be visualized with fluorescent probes (2). Genetic tools could provide new methods for Cam monitoring.

Two groups of genetic Cad probes are at present available. The first category uses the principle of Fluorescence Resonance Energy Transfer (FRET) between two variants of the green fluorescent protein (GFP). The two GFP are covalently linked by a calmodulin binding sequence alone or in combination with calmodulin so that intramolecular FRET does (3) or does not (4) occur in response to $Ca^{++}$ influx. The second category is composed by bioluminescent proteins, such as aequorin (5, 6). The active protein is formed in the presence of molecular oxygen from apoaequorin (189 amino acids) and its luciferin, coelenterazine (Mr 423) (7).

The binding of $Ca^{++}$ to aequorin, which has three EF-hand structures characteristic of $Ca^{++}$ binding sites, induces a conformational change resulting in the oxidation of coelenterazine via an intramolecular reaction. Moreover, the coelenteramide so produced is in an excited state, and blue light (max: 470 nm) is emitted when it returns to its ground state (8). Such a bioluminescent genetic marker presents the advantage over $Ca^{++}$ sensitive fluorescent dyes of being easily targeted to specific cells and in subcellular compartments with appropriate regulatory elements and peptide signals (9). The bioluminescent process does not require light excitation like fluorescent probes or proteins, and thus does not induce autofluorescence, photobleaching and biological degradation problems. Furthermore, aequorin is not toxic, does not bind other divalent cations and does not interfere with the $[Ca^{++}]_i$ buffer system even when microinjected at high concentrations. Its low affinity for $Ca^{++}$ (Kd=10 µM) is probably responsible for this and makes aequorin a good sensor in the range of biological $[Ca^{++}]$ variations.

Although providing a good ratio of signal over background, aequorin signals are very difficult to detect because of aequorin's low light quantum yield, that is, the number of emitted photons per protein that bind $Ca^{++}$. In the jellyfish, *Aequorea victoria*, from which aequorin has been isolated (10), the protein is associated with the GFP (11). After $Ca^{++}$ binding, the energy acquired by aequorin is transferred from the activated oxyluciferin to GFP without emission of blue light The GFP acceptor fluorophore is excited by the oxycoelenterazine through a radiationless energy transfer. Then, a green light (max, 509 nm) is emitted when the excited GFP returns to its ground state (12).

Such intermolecular radiationless energy transfer is not unusual in bioluminescence and has already been shown to increase the quantum yield of the bioluminescent process in *Renilla*, another coelenterate (13). The gain measured in vitro ranges from 3 to 5 fold (14). It is possible to reconstitute in vitro the Renilla system and obtain the spectral shift with low equimolar concentrations of its components because the luciferase and the green fluorescent protein bind together (14).

In the *Aequorea* system, binding between purified photoprotein and GFP does not occur in solution, even when present at high concentrations (15). In vivo, energy transfer occurs because of the high concentration of GFP. It can be obtained in vitro through the co-adsorption of aequorin and GFP on DEAE cellulose membranes (15). The Forster equation shows that the efficiency of this process depends on several conditions described in the case of FRET. The emission spectrum of the donor must have the greatest overlap with the excitation spectrum of the acceptor. The energy transferred is also strongly dependent on the geometry, in particular, the relative orientation and distance of the two dipoles and modulated by their respective motion (16).

An aim of this invention is to develop a dual reporter gene combining properties of $Ca^{++}$-sensitivity and fluorescence of aequorin and GFP, respectively. The fusion protein, which can be detected with classical epifluorescence, can be used to monitor calcium activities. The configuration of the molecules of the invention increases their overall turnover and allows an efficient intramolecular Chemiluminescence Resonance Energy Transfer (CRET). As a result, the quantum yield of aequorin appears to be higher. This invention shows that physiological calcium signals can be visualized in single eukazyotic cells with an intensified CCD camera Other constructs described here target the fusion protein to the neurite membrane.

SUMMARY OF THE INVENTION

This invention thus provides a modified bioluminescent system comprising a fluorescent molecule covalently linked with a photoprotein, wherein the link between the two proteins has the function to stabilize the modified bioluminescent system and allow the transfer of the energy by Chemiluminescence Resonance Energy Transfer (CRET). In a preferred embodiment, the bioluminescent system comprises a GFP protein covalently linked to an aequorin protein, wherein the link between the two proteins has the function to stabilize the modified bioluminescent system and to allow the transfer of the energy by Chemiluminescence Resonance Energy Transfer (CRET).

In one embodiment of a modified bioluminescent system according to the invention, the bioluminescent system comprises a GFP protein covalently linked to an aequorin protein, wherein the link between the two proteins is constituted by at least 5 amino acids and optionally at least 5 amino acids and at least one copy of 9 amino acids. The link has the function of stabilizing the system and allowing the transfer of energy by Chemiluminescence Resonance Energy Transfer (CRET).

In a preferred embodiment, the bioluminescent system comprises a GFP protein covalently linked to an aequorin protein, wherein the link between the two proteins is preferably constituted by at least 5 amino acids and five copies of 9 amino acids and has the function of stabilizing the system and allowing the transfer of energy by Chemiluminescence Resonance Energy Transfer (CRET).

The two proteins can be separate or together functional. In addition, the modified bioluminescent system can be calcium sensitive and/or light sensitive.

This invention also provides a method of screening in vitro a change in a physical, chemical, biochemical, or biological condition. The method comprises:
   a) providing in different samples a bioluminescent system according to the invention in a reaction system containing an analyte of interest;
   b) measuring whether light is produced; and
   c) detecting a change based on the production of light.

Further, this invention provides a method of screening in vivo a change in a physical, chemical, biochemical, or biological condition. The method comprises the steps of:
   a) administering to a mammal an acceptable composition comprising a bioluminescent system according to the invention;
   b) detecting whether light is produced; and
   c) optionally measuring ionic concentration of calcium flux.

In addition, this invention provides a composition comprising a purified polypeptide, wherein the composition has the functional characteristics of binding calcium ions and permitting measureable energy, said energy depending of the quantity of calcium bound and of the quantity of polypeptides in said composition in absence of any light excitation.

In addition, this invention provides a purified polypeptide having the amino acid sequence of SEQ ID NO: 1; SEQ ID NO: 2; SEQ ID NO: 3; SEQ ID NO: 4; SEQ ID NO: 5; and SEQ ID NO: 6.

In other embodiments, this invention provides a polynucleotide having the sequence of SEQ ID NO: 7; SEQ ID NO: 8; SEQ ID NO: 9; SEQ ID NO: 10; SEQ ID NO: 11; and SEQ ID NO: 12.

This invention also provides a culture as deposited at the C.N.C.M. and containing the plasmid No. I-2507; the plasmid No. I-2508; the plasmid No. I-2509; the plasmid No. I-2510; the plasmid No. I-2511; the plasmid No. I-2512; or the plasmid No. I-2513.

Further, this invention provides a peptide linker having the function after translation to approach a donor site to an acceptor site in optimal conditions to permit a direct transfer of energy by chemiluminescence in a purified polypeptide according to the invention. The nucleotide linker can have, for example, the nucleotide sequence of SEQ ID No: 13; SEQ ID No: 14; SEQ ID No: 15; SEQ ID No: 16, or SEQ ID No: 17. The peptide linker can comprise at least 5 amino acids and comprising the amino acid sequence of SEQ ID No: 18; SEQ ID No: 19; SEQ ID No: 20; SEQ ID No: 21; or SEQ ID No: 22.

A kit for measuring the transfer of energy in vivo or in vitro contains at least one of the polypeptides according to the invention or the polynucleotide according to the invention and the reagents necessary for visualizing or detecting the said transfer in presence or in absence of a molecule of interest In another embodiment, the invention provides a fusion protein of the formula:

GFP-LIKER-AEQ;

wherein GFP is green fluorescent protein; AEQ is aequorin; and LINKER is a polypeptide of 4-63 amino acids, preferably 14-50 amino acids.

The LNE can comprise the following amino acids:
(Gly Gly Ser Gly Ser Gly Gly Gln Ser [SEQ ID NO: 25])$_n$, wherein n is 1-5. Preferably n is 1 or n is 5. LINKER can also include the amino acid sequence Ser Gly Leu Arg Ser [SEQ ID NO: 26].

Another fusion protein for energy transfer from aequorin to green fluorescent protein by Chemiluminescence Resonance Energy Transfer (CRET) following activation of the aequorin in the presence of Cam has the formula:

GFP-LER-AEQ;

wherein GFP is green fluorescent protein; AEQ is aequorin; and LINKER comprises the following amino acids:
(Gly Gly Ser Gly Ser Gly Gly Gln Ser [SEQ ID NO: 25])$_n$, wherein n is 1-5; and wherein the fusion protein has an affinity for Cam ions and a half-life of at least 24 hours. The LINKER can include the amino acid sequence Ser Gly Leu Arg Ser [SEQ ID NO: 26]. In addition, the fusion protein can further comprise a peptide signal sequence for targeting the fusion protein to a cell or to a subcellular compartment This invention also provides polynucleotides encoding fusion proteins as described above.

BRIEF DESCRIPTION OF THE DRAWINGS

This invention will be described with reference to the drawings in which:

FIG. 1 discloses the pGA nucleotide and amino acid sequences as SEQ ID NOS 50 and 18, respectively and the pG$_i$A nucleotide and amino acid sequences as SEQ ID NOS 51 and 52, respectively.

Emission spectra of aequorin and several GFP-Aequorin fusion proteins were calibrated as a percentage of maximum intensity. CRET measurements are expressed as the ratio of green (500nm) over blue (450nm) photons.

Figure 3:
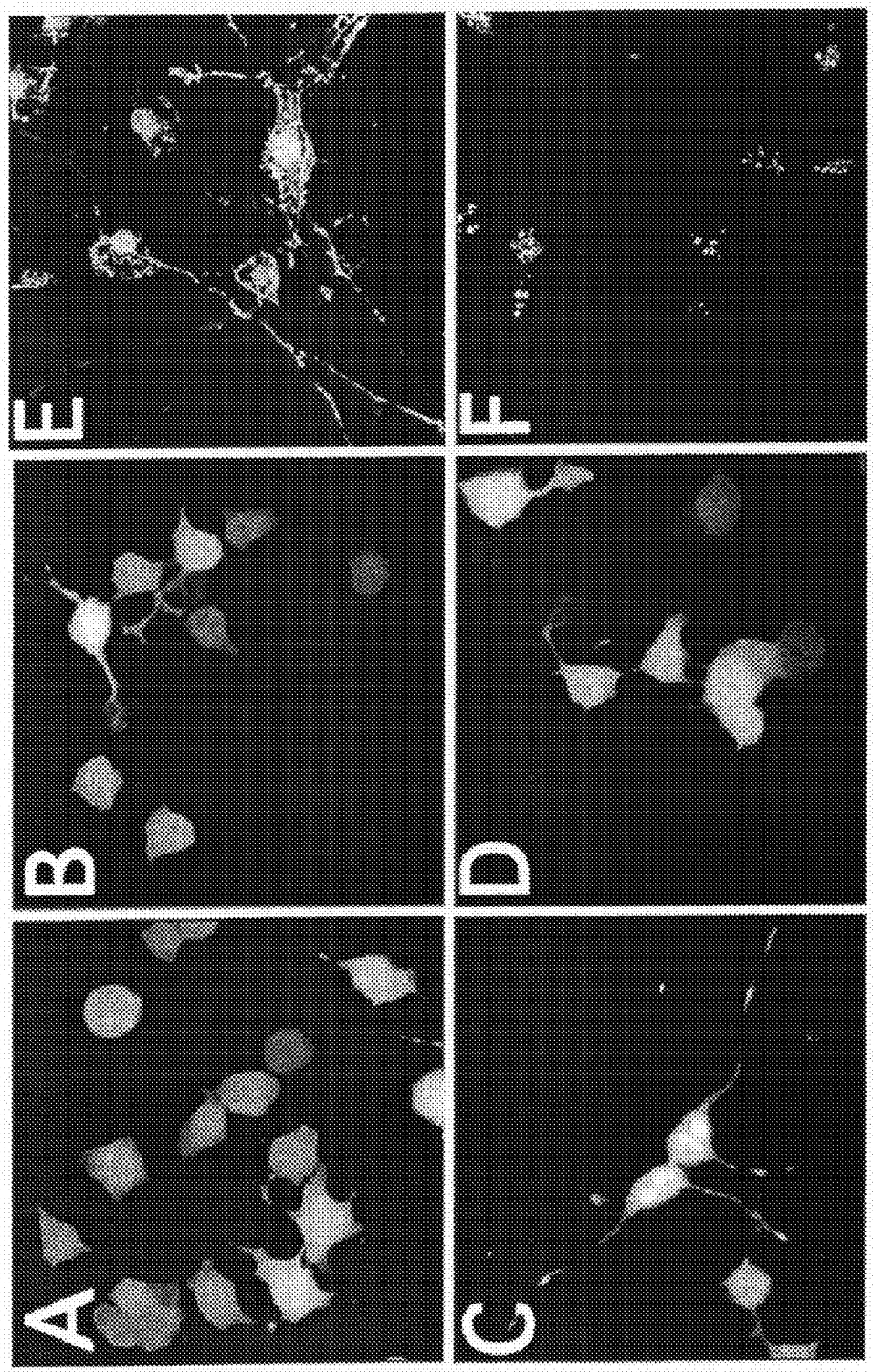
Figure 4A:
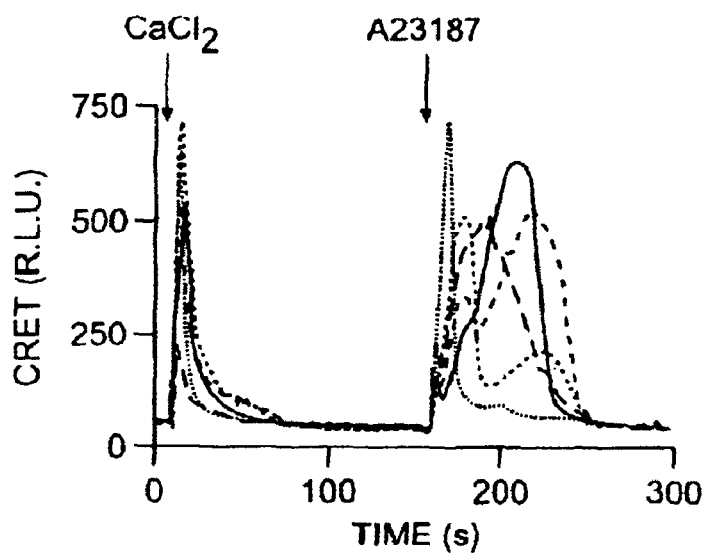
Figure 4B:
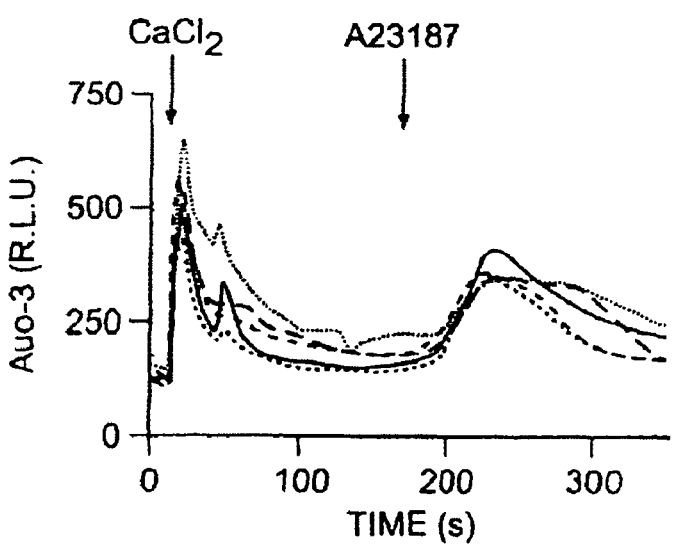
Figure 4C:
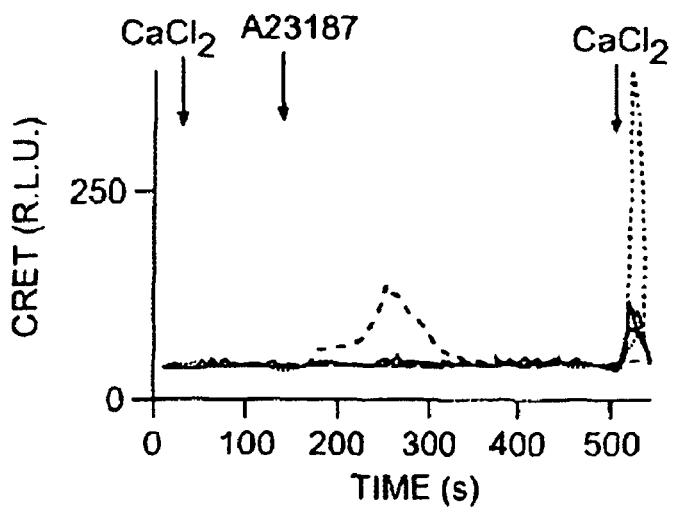

FIG. 3 depicts GFP fluorescence of GFP-Apoaequorin proteins in Neuro2A cells transfected with pGm (A), pGA (B), pG2A (C), and pG5A (D). Confocal superposition of GFP fluorescence and immunostaining of synaptotagmin in cells expressing either pSG5A (E) or pStG5A (F) is shown FIG. 4A.1, FIG. 4A.2, FIG. 4A.3, FIG. 4A, Fiq. 4B, and Fiq. 4C depict $Ca^{++}$-induced bioluminescence detected at the single cell level. Neuro2A cells transfected with pGA (FIG. 4A.1, FIG. 4A.2, FIG. 4A.3, and FIG. 4A) or pSG5A (FIG. 4B) were pre-incubated with 5μM coelenterazine in a $Ca^{++}$-free buffer. (FIG. 4A.3) GFP Fluorescence made it possible to choose transfected cells. The background recorded before $CaCl_2$ addition (panel A.2 of FIG. 4A.3) corresponds to the relative light unit (RLU) level at time 0 of the experiment (FIG. 4A, FIG. 4B, and FIG. 4C). Representative pictures of the chosen field are shown after addition of 5 mM $CaCl_2$ and 5 μM A23187 at 13 sec. and 159 sec, respectively, after the beginning of the acquisition (FIG.4A.1 and FIG.4A.2). (FIG.

4A, FIG.4B, and FIG.4C) Each profile indicates the intensity of light emitted by a single cell.

Five regions of interest were defined by encircling individual cell soma. With pGA (data not shown) or pSG5A (B) transfection, a high concentration of $CaCl_2$, (100 mM) was added at the end of the experiment (500 sec.) to check that the bioluminescent protein was still active. (C) Control experiments were made with Fluo-3 AM on mock-transfected Neuro2A cells.

Figure 5:
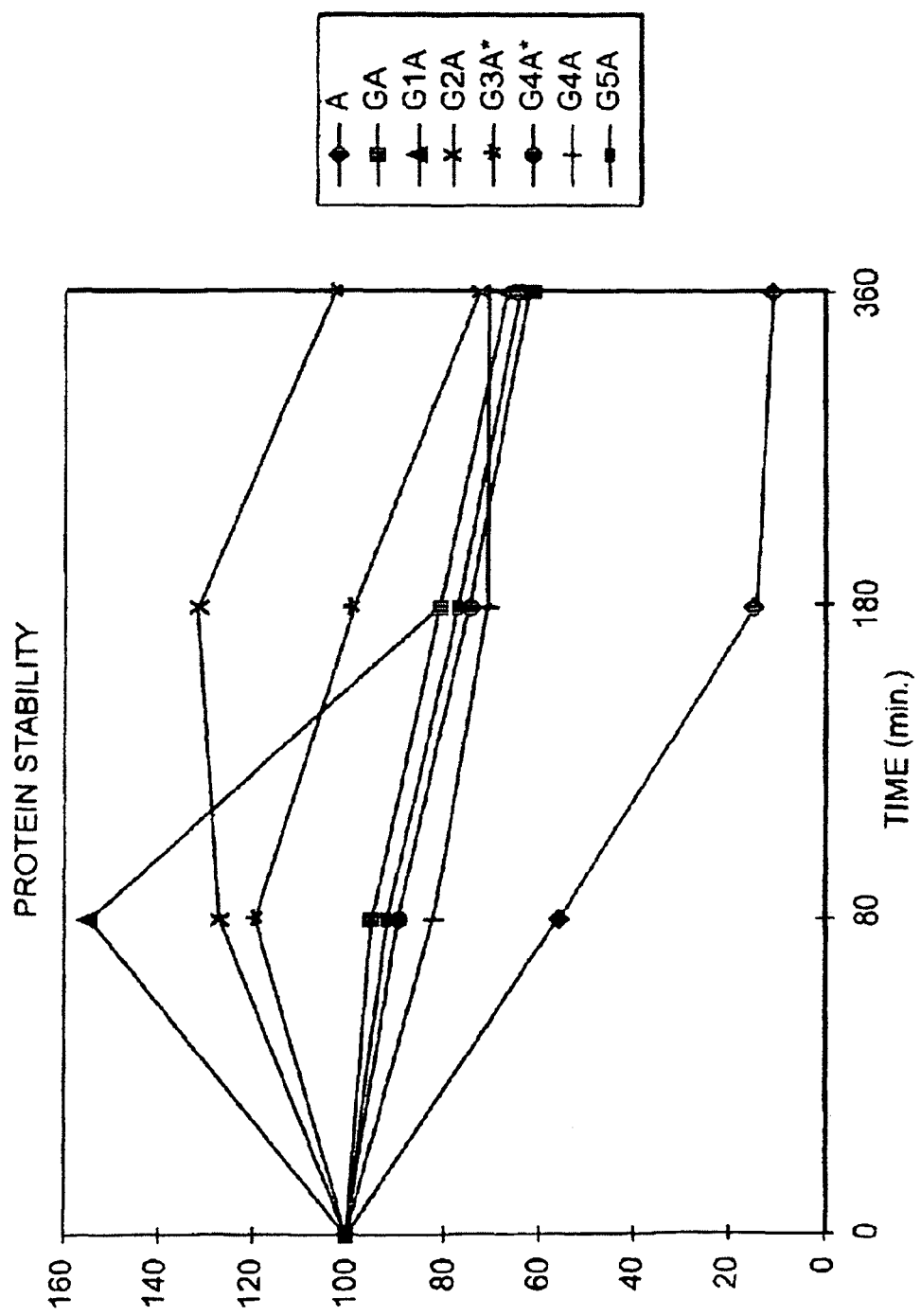

FIG. 5 depicts the results of analysis of protein stability for various fusion proteins.

Figure 6:
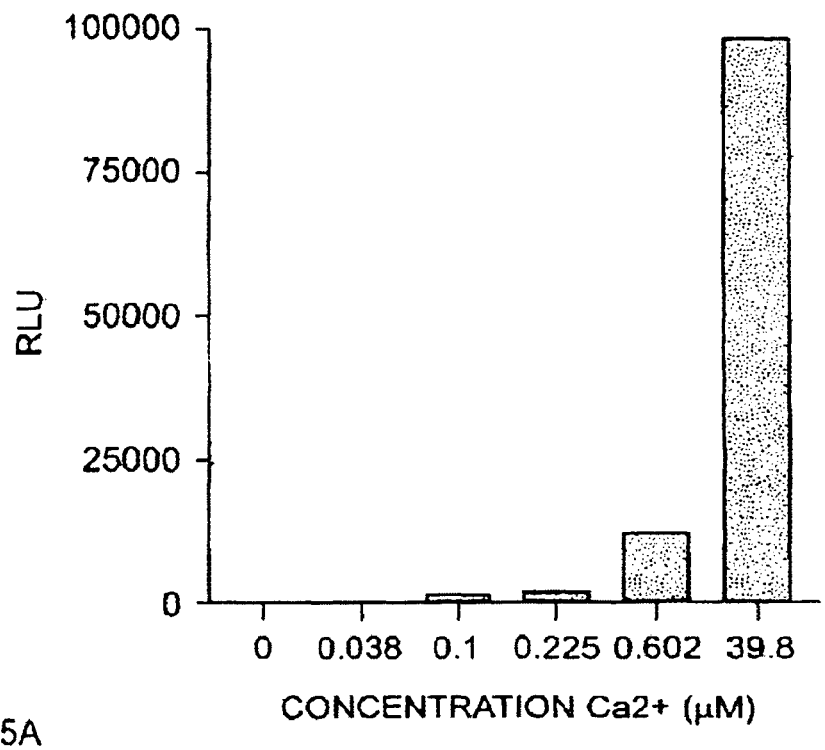
Figure 6:
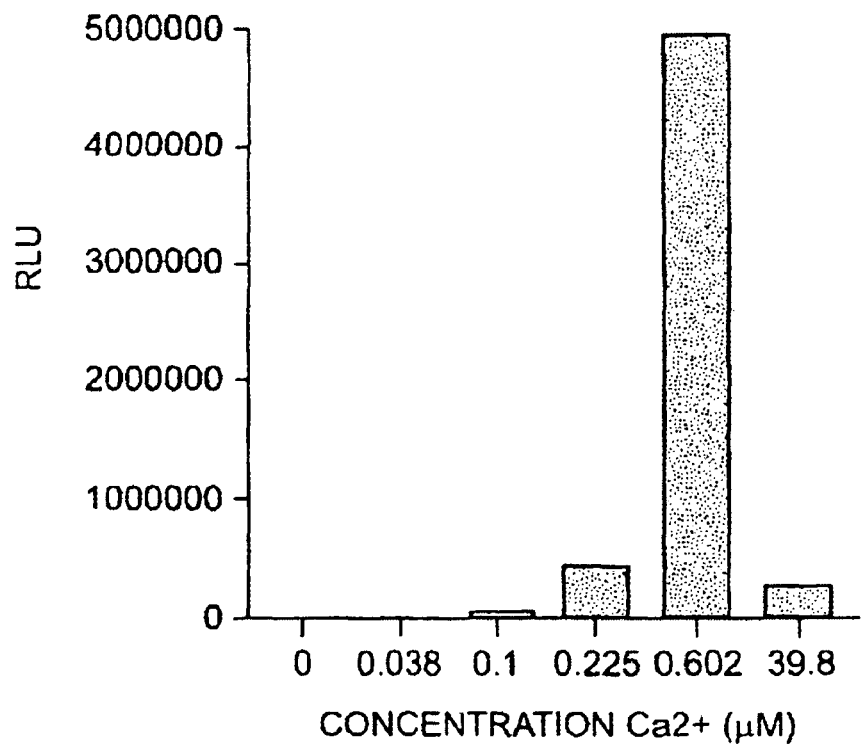
Figure 7:
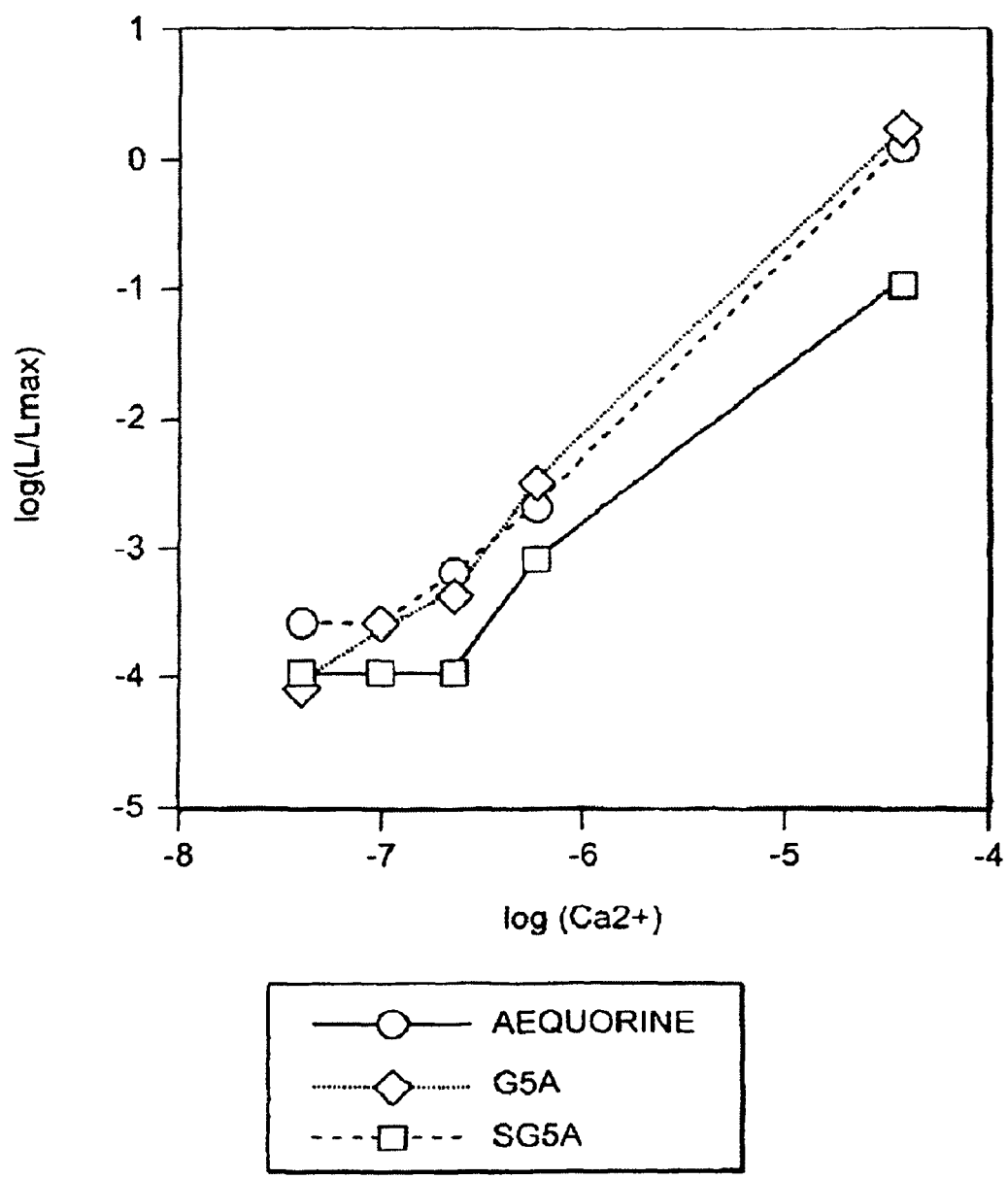

FIG. 6 depicts the results of the determination of the Ca affinity of aequorin and fusion protein G5A FIG. 7 depicts the calibration curves between the bioluminescent activity and Ca2+, for G5A, SG5A, and aequorin.

Figure 8:
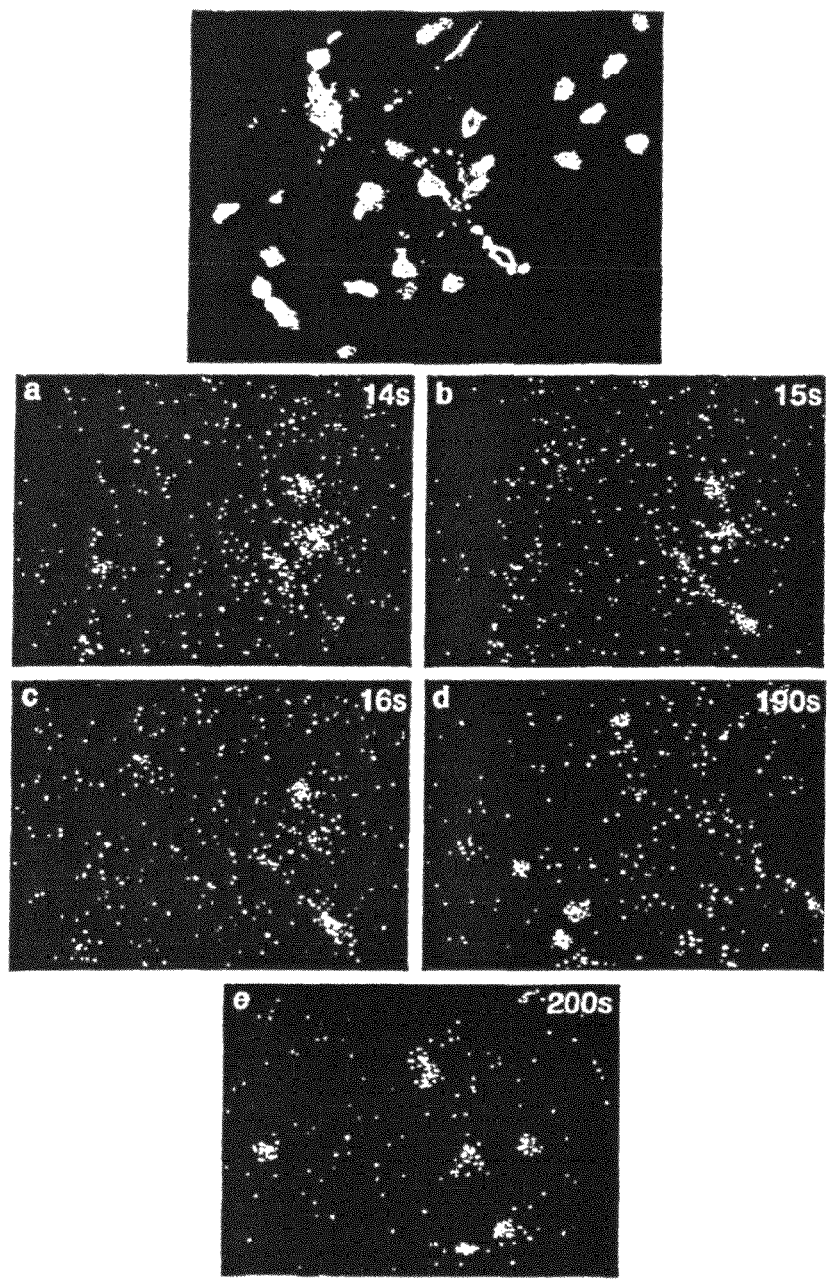

FIG. 8 shows fluorescence and Ca2+-induced bioluminescent activity in dissociated neurons in culture infected with adenoviral G5A vectors.

Figure 9:
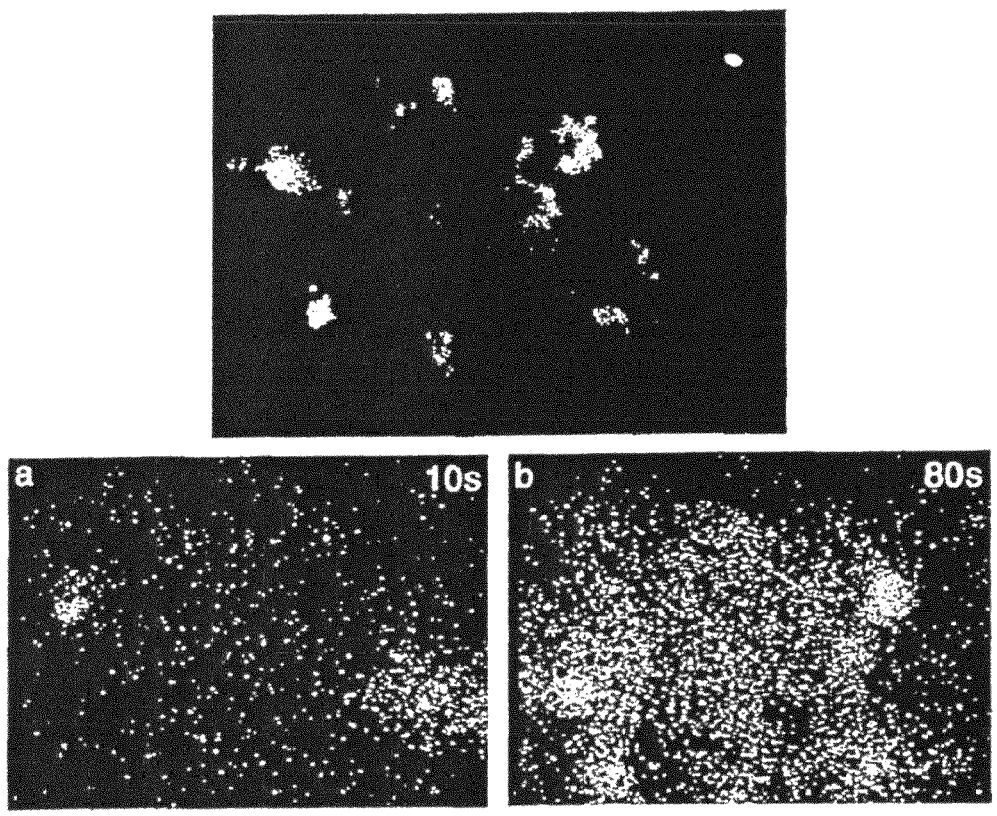

FIG. 9 shows fluorescence and Ca2+-induced bioluminescent activities in dissociated neurons in culture infected with adenoviral-SG5A vectors.

Figure 10B:
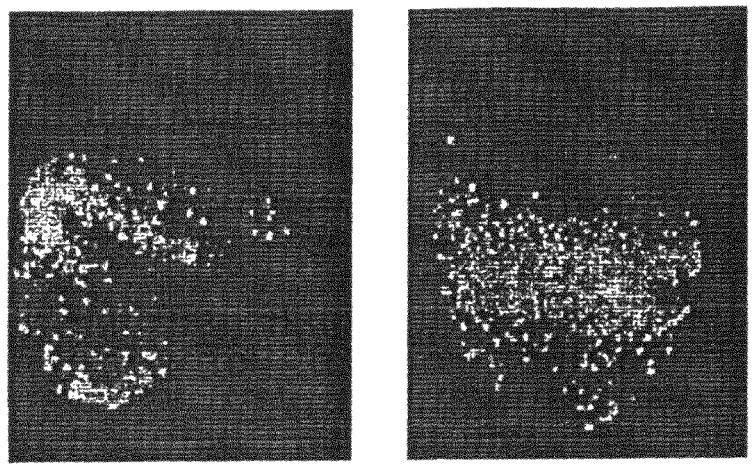
Figure 10A:
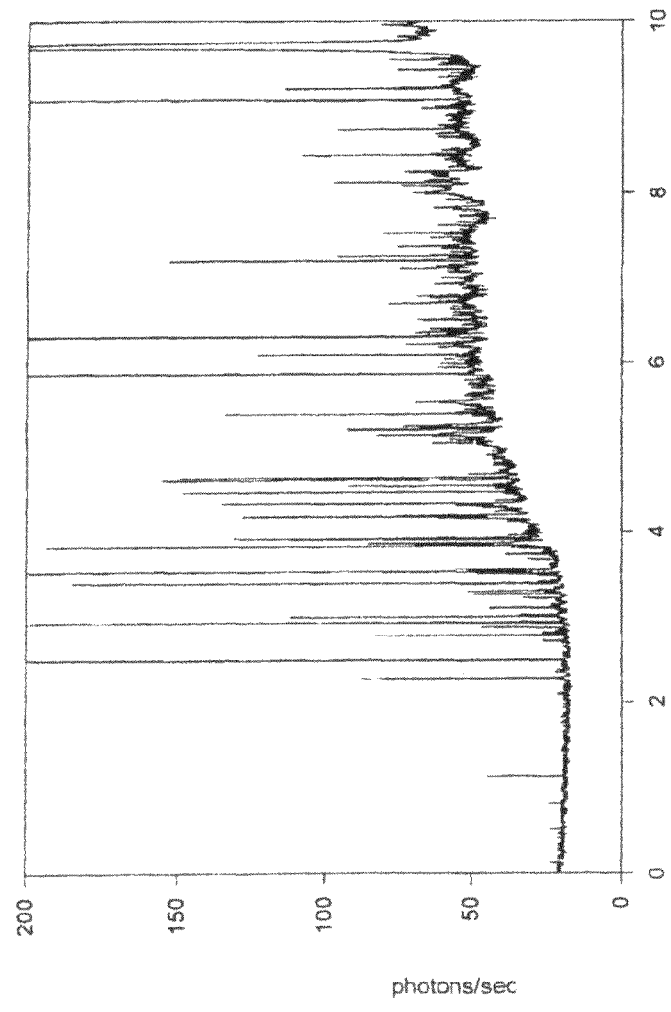

FIG. 10A and FIG. 10B show the representative pattern of luminescence activity after injection of GA plasmid at the one cell stage of *Xenopus* embryo.

Figure 11:
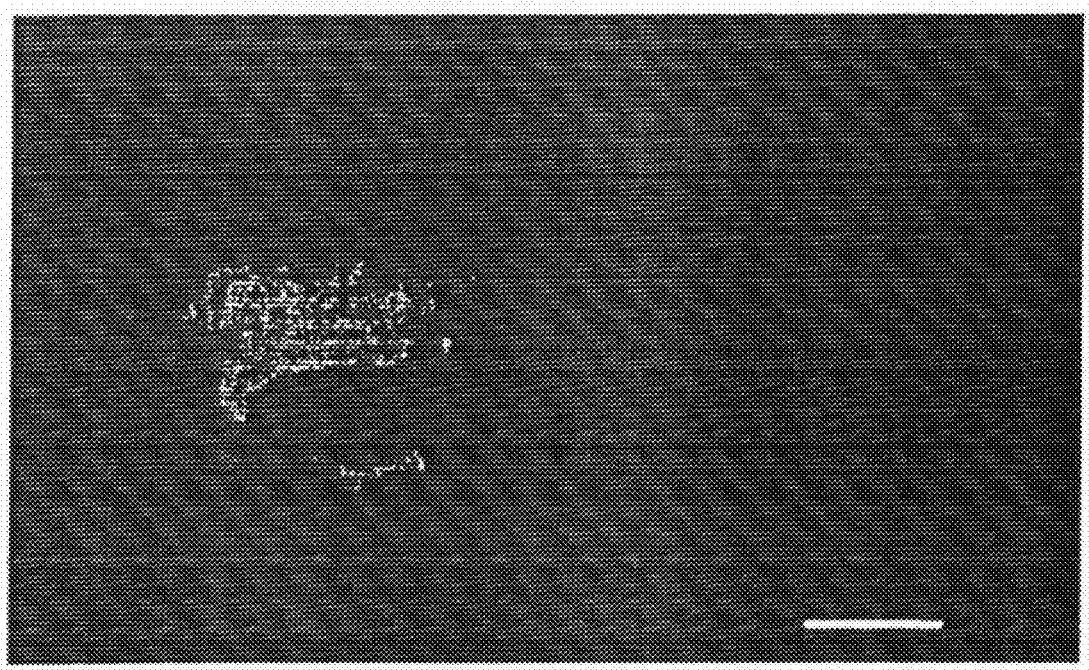

FIG. 11 shows a transgenic *Xenopus* larva with GFP-aequorin.

DETAILED DESCRIPTION OF THE INVENTION

Among the coelenterates, bioluminescent species exist. Numerous studies have shown that the bioluminescence is generated by photoproteins that are sensitive to calcium. These proteins emit a flash of light in response to an increase in the-concentration of calcium ions. Among these photoproteins, aequorin is one of the most well studied (Blinks et al., 1976).

Isolated in the jellyfish, *Aequoria Victoria* (Shimomura et al., 1962), aequorin, after binding with three calcium ions, emits a flash of blue light with a spectrum of maximum wavelength 470 mm. Contrary to a classical luciferase-luciferin reaction, the emission of light does not require oxygen, and the total amount of light is proportional to the amount of protein. Oxygen is necessary, however, to reconstitute the aequorin, by the action of apoaequorin, a protein with a molecular mass of 21 kDa, and coelenterazine. The emission of photons is caused by a peroxidation reaction in the coelenterazine, after binding with the three calcium ions on the aequorin. Two hypotheses have been suggested for this process: (i) the binding between aequorin and calcium ions induces the emission of light by a conformational change in the protein, allowing oxygen to react with coelenterazine, and (ii) oxygen plays a role in the binding between coelenterazine and apoaequorin (Shimomura and Johnson, 1978). Aequorin may be recreated in vitro and in vivo by eliminating oxyluciferin, adding luciferin (coelenterazine) in the presence of β-mercaptoethanol and oxygen (Shimomura and Johnson, 1978). The necessity of adding β-mercaptoethanol or a reducing agent to reconstitute aequorin is presumably due to the presence of at least one sulfhydryl group of cysteine 145 included in a negatively charged microenvironment (Charbonneau et al., 1985).

More than thirty semi-synthetic aequorins having different affinities for calcium ions have been characterized, based on the type of coelenterzine that binds to the protein (Shimomura, 1991; incorporated by reference herein). The dissociation constant between aequorin and the calcium ions is estimated to be between 0.1 mM (Allen et al., 1997) and 1 mM.(Prasher et al., 1985). Although the relationship between light emission and calcium ion concentration may not be linear, a logarithmic relationship between the emission of light and the calcium ion concentration has nonetheless been determined (Johnson and Shimomura, 1978). Indeed, a 200-fold increase in the signal to background noise ratio is measured when the $Ca^{++}$ concentration goes from $10^{-7}M$ to $10^{-6}M$, and by a factor of 1000, from $10^{-6}M$ to $10^{-5}M$ (Cobbold and Rink, 1987). Moreover, the kinetics of the signal emission is rapid enough to detect transitory increases in $Ca^{++}$ ion concentrations. An increase in light intensity with a time constant of 6 msec, under calcium saturation conditions, has been shown (Blinks et al., 1978). Aequorin is thus a photoprotein that is well adapted to measure rapid and elevated increases in $Ca^{++}$ ions. under physiological conditions.

The cloning of the apoaequorin gene by Prasher et al., (1985) and Inouye et al. (1985) has led to the creation of expression vectors, making possible its targeting in a specific cell compartment by fusion with nuclear, cytoplasmic, mitochondrial, endoplasmic reticulum, or plasma membrane signal peptides (Kendall el al., 1992; Di Giorgio et al., 1996). In addition, the in vivo expression of the protein makes possible its detection at low levels, leaving the intracellular physiology of calcium undisturbed.

In nature, photoprotein activity is very often linked to a second protein. The most common is the "green flourescent protein" or GFP. The light emitted in this case is in fact green. The hypothesis of an energy transfer between aequorin and GFP by a radiative mechanism was proposed in the 1960s by Johnson et al., (1962). The blue light emitted by aequorin in the presence of Cam is presumably absorbed by GFP and reemitted with a spectrum having a maximum wave length of 509 nm. Other studies have shown that this transfer of energy occurs through a non-radiative mechanism made possible through the formation of heterotetramer between GFP and aequorin. Morise et al. (1974) have succeeded in visualizing this energy transfer in vitro, and a co adsorption of the two molecules on a DEAE-cellulose membrane facilitates the process. Through this mechanism, it thus appears possible to increase the quantum efficiency of the system (Ward and Cormier, 1976).

GFP, also isolated in the jelly fish *Aequoria Victoria*, was recently cloned (Prasher et al., 1992). It has been used in different biological systems as a cellular expression and lineage marker (Cubitt et al., 1995). Detecting this protein using classical fluorescence microscopy is relatively easy to do in both living organisms and fixed tissue. In addition, fluorescent emission does not require the addition of a cofactor or coenzyme and depends on an autocatalytic post-translational process. The fluorophore, consisting of nine amino acids, is characterized by the formation of a cycle between serine 65 and glycine 67, which gives rise to an intermediate imidazolidine 5, followed by oxidation of tyrosine 66, transforming it into dehydrotyrosine (Heim et al., 1994). This group is found inside a cylinder composed of 11 β layers, which constitutes an environment that interacts directly with the chromophore (Yang et al., 1996).

Monitoring calcium fluxes in real time could help to understand the development, the plasticity, and the functioning of the central nervous system. In jellyfish, the chemiluminescent, calcium binding, aequorin protein is associated with the green fluorescent protein (GFP), and a green bioluminescent signal is emitted upon $Ca^{++}$ stimulation Aequorin alone is difficult to detect on the cellular and subcellular level owing to the weak emission of photons after excitation.

The development of a new marker sensitive to calcium with a higher quantum yield was therefore initiated This invention utilizes Chemiluminescence Resonance Energy Transfer (CREF) between the two molecules. Calcium sensitive bioluminescent reporter genes have been constructed by fusing GFP and aequorin resulting in much more light being emitter Chemiluminescent and fluorescent activities of these fusion proteins have been assessed in mammalian cells. Cystosolic $Ca^{++}$ increases were imaged at the single cell level with a cooled intensified CCD (coupled charge device) camera. This bifunctional reporter gene should allow the investigation of calcium activities in neuronal networks and in specific subcellular compartments in transgenic animals.

GFP-aequorin Fusion Proteins as $Ca^{++}$-Activated Reporter Genes.

According to this invention, a fusion protein has been constructed with aequorin and GFP to increase the quantum yield of $Ca^{++}$-induced bioluminescence. This activity can not be increased simply by co-expressing GFP with aequorin (data not shown). A thermoresistant GFP (Gm) was fused in frame with the $NH_2$ terminal region of apoaequorin (FIG. 1), since the C-terminal proline residue has been shown to be implicated in the $Ca^{++}$-activated bioluminescent process (20).

Figure 1:
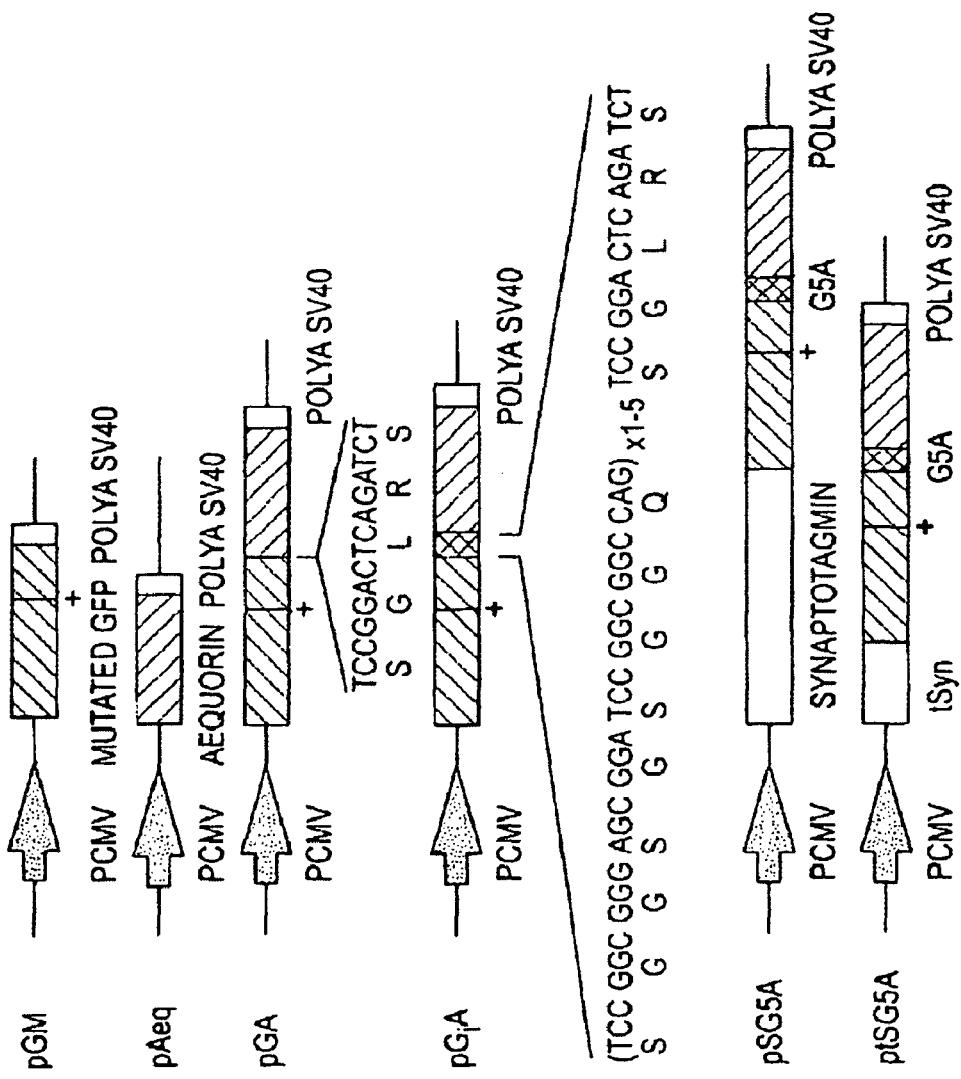
FIG. 1 is a schematic map of different constructions. All the constructs were under the control of the human cytomegalovirus promoter (PCMV). An asterisk indicates the position of a Val-163-Ala mutation. In pGA, the coding sequences of GFP and aequorin are separated by 5 codons. One to five linkers (in brackets) have been added in pG$_i$A where i is the number of linker. Linkers were oriented so as to encode a 9 amino acid repeat. Complete Synaptotagmin 1 or its transmembrane part (tSyn) were fused in frame with the G5A.

Different constructs have been made with increasing size of linker between GFP and apoaequorin. The shortest spacer is formed by 5 amino acids and the longest by 50 amino acids (FIG. 1). All the fusion proteins showed a better $Ca^{++}$-triggered bioluminescent activity than aequorin alone. The increases of light emitting activity ranged from 19 to 65 times (Table 1) possibly because of greater protein stability.

TABLE 1

CA++ INDUCED CHEMILUMINESCENCE ACTIVITIES

| Name | Mean ± SEM* $RLU \times 10^6/10\ U\beta gal$ |
|---|---|
| pA | 0.15 (0.10; 021) |
| pGa | 10.01 ± 4.4 |
| pG1A | 2.96 (3.39; 2.53) |
| pG2A | 8.39 (9.54; 7.23) |
| pG4A | 7.78 (12.02; 3.53) |
| pG5A | 8.15 ± 1.72 |

*SEM is indicated when more than two measures were made. Otherwise the two measures are given.

The plasmids identified in Table 1 are described in detail hereafter. The following sequence identifiers are used to describe the amino acid and nucleotide sequences of each plasmid insert

TABLE 2

SEQUENCE IDENTIFIERS

| Plasmid Insert | Amino Acid Sequence | Nucleotide Sequence |
|---|---|---|
| A | ★ | ★ |
| GA | SEQ ID NO: 1 | SEQ ID NO: 7 |
| G1A | SEQ ID NO: 2 | SEQ ID NO: 8 |
| G2A | SEQ ID NO: 3 | SEQ ID NO: 9 |
| G4A | SEQ ID NO: 4 | SEQ ID NO: 10 |
| G5A | SEQ ID NO: 5 | SEQ ID NO: 11 |
| SeG5A | SEQ ID NO: 6 | 12 |

★ The nucleotide sequence of apoaequorin is contained in U.S. Pat. No. 5,422,266.

The identity of the linker used in these constructs is as follows:

DNA sequence of GFP-aequorin linker
pGA (strain I-2507)

```
                                            [SEQ ID NO: 13]
TCC GGC CTC AGA TCT pG1A (strain I-2508)
                                            [SEQ ID NO: 14]
TCC GGC GGG AGC GGA TCC GGC GGC CAG TCC GGC CTC

AGA TCT pG2A (strain I-2509)
                                            [SEQ ID NO: 15]
TCC GGC GGG AGC GGA TCC GGC GGC CAG TCC GGC GGG

AGC GGA TCC GGC GGC CAG TCC GGC CTC CTC AGA TCT pG4A (strain I-2510)
                                            [SEQ ID NO: 16]
TCC GGC GGG AGC GGA TCC GGC GGC CAG TCC GGC GGG

AGC GGA TCC GGC GGC CAG TCC GGC GGG AGC GGA TCC

GGC GGC CAG TCC GGC GGG AGC GGA TCC GGC GGC GAG

TCC GGC CTC AGA TCT pG5A (strain I-2511)
                                            [SEQ ID NO: 17]
TCC GGC GGG AGC GGA TCC GGC GGC CAG TCC GGC GGG

AGC GGA TCC GGC GGC CAG TCC GGC GGG AGC GGA TCC

GGC GGC CAG TCC GGC GGG AGC GGA TCC GGC GGC CAG

TCC GGC GGG AGC GGA TCC GGC GGC CAG TCC GGC CTC

AGA TCT pSeG5A (strain I-2512) and pStG5A (strain I-2513)
same linker sequence as pG5A.

Peptide sequence of linker
pGA
                                            [SEQ ID NO: 18]
Ser Gly Leu Arg Ser pGLA
                                            [SEQ ID NO: 19]
Ser Gly Gly Ser Gly Ser Gly Gly Gln Ser Gly Leu Arg Ser pG2A
                                            [SEQ ID NO: 20]
Ser Gly Gly Ser Gly Ser Gly Gly Gln Ser Gly Gly Ser Gly Ser Gly Gly Gln Ser Gly Leu Arg Ser pG4A
                                            [SEQ ID NO: 21]
Ser Gly Gly Ser Gly Ser Gly Gly Gln Ser Gly Gly Ser Gly Ser Gly Gly Gln Ser Gly Gly Ser Gly Ser Gly Gly Gln Ser Gly Gly Ser Gly Ser Gly Gly Gln Ser Gly Leu Arg Ser pG5A
                                            [SEQ ID NO: 22]
Ser Gly Gly Ser Gly Ser Gly Gly Gln Ser Gly Gly Ser Gly Ser Gly Gly Gln Ser Gly Gly Ser Gly Ser Gly Gly Gln Ser Gly Gly Ser Gly Ser Gly Gly Gln Ser Gly Gly Ser Gly Ser Gly Gly Gln Ser Gly Leu Arg Ser pSeG5A and pStG5A idem than pGSA
```

Plasmids containing the foregoing polynucleotides have been deposited at the Collection Nationale de Cultures de Microorganismes ("C.N.C.M"), Institut Pasteur, 28, rue du Docteur Rowx, 75724 Paris Cedex 15, France, as follows:

| Insert | Plasmid | Accession No. | Deposit Date |
| --- | --- | --- | --- |
| A | pAeq+ | I-2506 | Jun. 22, 2000 |
| GA | pGa | I-2507 | Jun. 22, 2000 |
| G1A | pG1A | I-2508 | Jun. 22, 2000 |
| G2A | pG2A | I-2509 | Jun. 22, 2000 |
| G4A | pG4A | I-2510 | Jun. 22, 2000 |
| G5A | pG5A | I-2511 | Jun. 22, 2000 |
| SeG5A | pSeG5A | I-2512 | Jun. 22, 2000 |
| StG5A | pStG5A | I-2513 | Jun. 22, 2000 |

Recombinant apoaequorin is unstable within the cytosol with a half-life of approximately 20 minutes (21). In contrast, GFP is a very stable protein and probably stabilizes apoaequorin in the chimeric proteins. The turnover times of the different cytosolic proteins were estimated on transient expression in COS 7 cells by treatment with puromycin (50 µg/ml) for 6 hours. Over this period, most fusion proteins presented a 30% decrease of activity compared with the 80% loss of apoaequorin when alone (FIG. 5). It has been observed that, in vitro, the fusion proteins of the invention were more sensitive than aequorin alone. GSA gives a significant signal over background with $Ca^{++}$ concentration as low as 38 nM, whereas aequorin needs 28 times more calcium (1 µM) to yield a comparable signal (FIG. 6). Energy transfer may also improve the quantum yield of GFP-aequorin allowing a more efficient calcium ions detection. To discriminate among the factors contributing to the higher light emission, it will be necessary to study the relaxation mechanisms of the GFP fluorescent excited state on purified hybrid proteins.

More generally, one embodiment of this invention provides a chimeric protein starting with the genes for GFP and aequorin. Improved quantum yield will depend on the functional coupling of the proteins by a Chemiluminescence Resonance Energy Transfer (CRET) mechanism. Thus, after the reconstitution of aequorin and its binding with calcium ions, the activated aequorin transmits its energy to the GFP, which in turn emits a green light to return to its ground state. Optimizing the functional coupling between the two proteins has focused on three points:

1. Improving the induction of a conformational change in the GFP at 37° C., which leads to a higher emission of GFP in the mammalian cells;
2. Changing to the use of aequorin codons adapted to mammalian cells to enhance its expression; and
3. Adding a linkage peptide between the two proteins.

With respect to the third point, an initial molecular construct with five amino acids separating the two proteins was first completed. Then a sequence of nine amino acids was added in a sequence of one to five copies. These constructs were placed in a eukaryote expression vector under control of the CMV (cytomegalovirus) promoter allowing their functional ability to be confirmed. These fusion proteins may be identified: (i) by the GFP signal through excitation of the biological preparations with light of wavelength 470 nm, by fluorescence microscopy (FITC filter); (ii) by aequorin activity, through emission of blue light after binding with Ca++ ions.

The following terms have the following meanings when used herein:

Luminescence
Emission of an electromagnetic radiation from an atom or molecule in UV, in visible or IR. This emission results from the transition from an electronically excited state towards a state from weaker energy, generally the ground state.

Fluorescence
Fluorescence produced by a singlet, very short, excited electronically. This luminescence disappears at the same time as the source from excitation.

Chemiluminescence
Luminescence resulting from a chemical reaction.

Bioluminescence
Visible chemiluminescence, produced by living organisms. The invention mimics the system naturally present in the jellyfish, without fixation to a support Bioluminescent system
The bioluminescent system according to the invention is a chimeric tripartite molecule within the middle a peptide linker and a coenzyme (i.e., coelenterazine). The first molecule and the second molecule covalently attached with the linker can be everything if they have for the first a donor site and for the second an acceptor site attached on it (receptors-linker-ligand, antibody-linker antigen). The chimeric protein can be fused to a fragment of tetanus toxin for its retrograde and transynaptic transport on axon by Coen, L., Osta, R., Maury, M., and Brulet, P., Construction of hybrid proteins that migrate retrogradely and transyaptically into the central nervous system. Proc. Natl. Acad. Sci. (USA) 94 (1997) 9400-9405, or fused to a membrane receptor.

Non-Radiative
No emission of photon from aequorin to the GTP when aequorin is bounded by calcium ions (therefore there is no transmission of blue light by aequorin in the invention, the energy transfer is directly made between the two proteins).

FRET system
Transfer of energy by resonance by fluorescence (i.e., between two variants of GFP).

References
Fluorescent indicators for Ca2+ based on green fluorescent proteins and calmodulin.
Miyawalci, A., Llopis, J., Heim, R., McCaffery, J. M., Adams, J. A., Ikura, M. and Tsien, R. Y. Nature, (1997) Vol. 388 pp. 882-887.
Detection in living cells of Ca2+-dependent changes in the fluorescence emission of an indicator composed of two green fluorescent protein variants linked by a calmodulin-binding sequence. A new class of fluorescent indicators.
Romoser, V. A., Hinkle, P. M. and Persechini, A., J. Biol. Chem., (1997) Vol. 272, pp. 13270-13274.

CRET
Transfer of energy by resonance by chemiluminescence (i.e., fulsion protein with GFP-aequorin (jellyfish Aequorea) but without linker or GFP-obeline).
Reference:
Chemiluminescence energy transfer.
Campbell, A. K., in Chemiluminescence: Principles and application in Biology and Medicine, Eds Ellis Horwood, Chichester, UK 1988, pp. 475-534.

BRET
Transfer of energy by resonance by bioluminescence (i.e., interaction between GFP and luciferase (jellyfish Renilla).
Reference:
A bioluminescence resonance energy transfer (BRET) system: application to interacting circadian clock protein. Xu, Y., Piston, D. W. and Johnson, C. H. Proc. Natl. Acad. Sci., (USA) (1999) Vol. 96, pp. 151-156.

Application 1: Study of Calcium Signals from a Cell Population in a Eukaryotic Organism.

Targeting the bioluminiscent protein sensitive to calcium in a cell population or in a specific tissue may be achieved through homologous recombination or by transgenesis under the control of a specific promoter. Replacing genes by homologous recombination in embryonic cells in mice, such, as Hoxc-8 and Otxl, with this new marker will make it possible to obtain new lines of mutant mice. This approach will permit the detection of electrical activity in a group of neural cells, and will also make it possible to complete the phenotype study of mutants obtained by replacing the LacZ gene (Le Mouéllic et al., 1990, 1992; Acampora et al., 1996). For the Hoxc-8 locus, the expression of the marker should be located in the ventral horns of the spinal chord beginning at section C7 (Le Mouellic et al., 1990). Anomalies in the somatotopic organization of the motor neurons innervating these muscles have been brought to light (Tiret et al., 1998), and a study of the role of the flux of calcium in the establishment of these neural connections during development may thus be undertaken. In the Otxl model, the transgene should be expressed in specific regions of the forebrain, given that an expression localized at layers V and VI of the cerebral cortex, and in regions of the diencephalon, mesencephalon, and cerebellum have been shown (Frantz et al., 1994). Mutant mice obtained by the replacement of the gene by the LacZ gene show a reduction in the thickness of the cerebral cortex and anomalies in the hippocampus, mesencephalon, and cerebellum (Acampora et al., 1996). The loss of balance and rotatory movement observed in these mice can presumably be attributed to anomalies in the sensory organs, specifically in the eye and inner ear. These mice are also subject to generalized epileptic seizures. The establishment of faulty connections and/or abnormal electrical activity could be implicated in the genesis of these pathological processes (McNamara, 1992). The use of this new marker will, on the one hand, make it possible to verify these hypotheses through a functional and dynamic approach, and on the other, to address the development of epilepsy in the adult as well as during development Application 2: Study of the Role of Intracellular Calcium Calcium is involved in a large number of cellular mechanisms, such as cellular migration, membrane excitability, mitochondrial metabolism, secretion, mitosis, and synaptic plasticity (Berridge et al., 1998). Coding calcium information at the cellular and subcellular level is complex, involving spatial, temporal and quantitative factors. Targeting marker of the invention to different subcellular compartments is possible by fusion with a peptide signal, for example, synoptotagmine.

Example A: Targeting the nuclear compartment will make it possible to study the role of calcium in transcription activation mechanisms and during the mechanisms related to programmed cell death (apoptosis).

Example B: Targeting two fusion proteins with GFP produces different emission spectra in the two cell compartments, for example, cytoplasm and the endoplasmic reticulum will make it possible to study the regulation of the calcium flux during cell activations.

Example C: Targeting the fusion protein in the synapses will make it possible to study the calcium activity linked to electrical activity in neural cells during the release of neurotransmitters. The first possibility is the achievement of a triple fusion between a synaptic protein, such as synaptotagmine or SNAP25, GFP, and aequorin. The existence of protein-protein interactions during exocytosis makes it possible to consider a second possibility: A functional coupling between GFP and aequorin, the one in fusion with a vesicular protein and the other with a plasma protein A signal will be obtained only during the interaction of the different proteins in the presence of an increase in the calcium ion concentration.

Application 3: Study of calcium signals at the cell population level

Triple fusing of a protein having intercellular transport properties such as fragment C of the tetanus toxin (TTC) or the VP22 protein of the herpes virus with GFP and aequorin will make it possible to observe the calcium activity in a population of connected cells, for example in a neural network.

Description of the Construction of a Bioluminescent Marker Expression Vector Sensitive to Calcium Ions Stage 1: pEGFP-CldKS (KpnI-SmaI Deletion)

Double digestion of pEGFP-Cl plasmid (Clontech, see figure) with KpnI and SmaI enzymes. After blunt ending the KpnI extension with "Mung bean" nuclease, the two extremities are ligated.

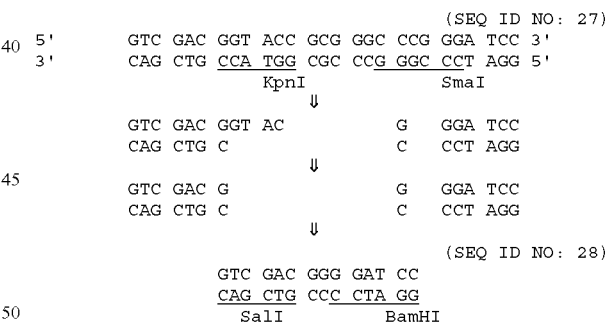

('GTCGACGGTAC' disclosed as SEQ ID NO: 49)

Stage 2: pEGFP-Clmut (GFP mutagenesis)

Four mutagenesis oligonucleotides were used on a single-strand molecule prepared using pEGFP-CldKS. Each oligonucleotide comprises one or several mismatches (identified below in lower case letters), causing the desired mutation. In the pEGFP-Clmut plasmid chosen, cut with the SacII enzyme but not the AgeI enzyme, all of the mutations were verified by sequencing Destruction of the AgeI site, introduction of a SacII site and deletion of a Valine codon normally absent in "wild-type" GFP (Prasher, D. C., Eckenrode, R.K., Ward, W.W., Prendergast, F.G., and Cormier, M.J., Primary structure of the *Aequorea* victoria green-fluorescent protein. Gene 111 (1992) 229-233.)

```
                 SacII          Met      Ser Lys Gly Glu
oGM1:        5' GCGCTACCGcggGCCACC ATG    AGC AAG GGC GAG 3' pEGFP-CldKS: 5' GCGCTACCGGTCGCCACC ATG GTG AGC AAG GGC GAG 3'
                    AgeI              Val
```

(SEQ ID NOS 30, 29 and 31-32, respectively, in order of appearance)

Replacement of the 163 Valine codon by an Alanine codon in order to increase the quantity of GFP assuming a correct conformation at 37° C. (Siemering, K.R., Golbik, R., Sever, R., and Haseloff, J., Mutations that suppress the thermosensitivity-of green fluorescent protein. Current Biol. 6 (1996) 1653-1663.)

```
                 Ile Lys Ala Asn Phe Lys
oGM2:        5' GC ATC AAG Gcc AAC TTC AAG 3' pEGFP-CldKS  5' GC ATC AAG GTG AAC TTC AAG 3'
                           Val
```

(SEQ ID NOS 34, 33 and 35-36, respectively, in order of appearance)

Replacement a 231 Leu codon by a Histidine codon normally present in "wild-type" GFP (Prasher, D.C., Eckenrode, V.K., Ward, W.W., Prendergast, F.G., and Cormier, M.J., Primary structure of the *Aequorea* victoria green-fluorescent protein. Gene 111 (1992) 229-233.)

```
                 Ile Thr His Gly Met
oGM3:        5' GG ATC ACT CaC GGC ATG GA 3' pEGFP-CldKS: 5' GG ATC ACT CTC GGC ATG GA 3'
                         Leu
```

(SEQ ID NOS 38, 37 and 39-40, respectively, in order of appearance)

Stage 3: pEGFPmut-Aeg (GFP-Aeguorin fusion protein)

Four PCRs (Polymerase Chain Reaction) done on a vector comprising the aequorin (Aeq) coding phase makes it possible to amplify the A, B, C, and D fragments with, respectively, the primers oAE5A and oAE3A, oAE5B and OAE3B, oAE5C and oAE3C, oAE5D and oAE3D. The overlapping regions are used to assemble the different parts during successive PCRs (Ho, S.N., Hunt, H.D., Horton, R.M., Pullen, J.K, and Pease, L. R. Site-directed mutagenesis by overlap extension using the polymerase chain reaction Gene 77 (1989) 51-59.) An A+B fragment is amplified starting with a mixture of A and B fragments, and the primers oAE5A and oAE3B. Similarly, a C+D fragment is amplified with a mixture of C and D fragments, using the primers oAESA and oAE3D. Finally, the complete coding phase, A+B+C+D is developed with the primers oAE5A and oAE3D.

Each oligonucleotide comprises one or several mismatches that are identified below in lower case. The "wild" sequence is represented opposite, in upper case. The primer oAE5A suppresses the original initiation translation code (ATG) and introduces a Bg1II site. The primer oAE3D introduces an XhoI site just behind the translation terminal codon (TAA). The final PCR product, digested with the Bg1II and XhoI enzymes, is cloned in the Bg1TI-SalI sites of the pEGFP-Clmut plasmid in such a way that the Valine codon (GTC), the first codon of aequorin, is in the same reading phase as the GFP (see figure). The other primers introduce "silent" mutations that do not change the protein sequence but modify six codons in the jellyfish, *Aequoria* victoria, to improve their expression in mammals (Wada, K-N., Aota, S.-I., Tsuchiya, R, Ishibashi, F., Gojobori T., and Ikemura, T. Codon usage tabulated from the GenBank genetic sequence data. Nucleic Acids Res. 18 suppl. (1990) 2367-2411.). The completeness of the entire sequence was verified by sequencing,

```
         oAE5A  CCATG
5'AGCTTCAgatct GTC AAA CTT ACA TCA GAC TTC GAC AAC CCA AGA TGG ATT GGA CGA
3'TCGAAGTctaga CAG TTT GAA TGT AGT CTG AAG CTG TTG GGT TCT ACC TAA CCT GCT
         BGlII CAC AAG CAT ATG TTC AAT TTC CTT GAT GTC AAC CAC AAT GGA AAA ATC TCT CTT GAC GAG
GTG TTC GTA TAC AAG TTA AAG GAA CTA CAG TTG GTG TTA CCT TTT TAG AGA GAA CTG CTC
ATG GTC TAC AAG GCA TCT GAT ATT GTC ATC AAT AAC CTT GGA GCA ACA CCT GAG CAA GCC
TAC CAG ATG TTC CGT AGA CTA TAA CAG TAG TTA TTG GAA CCT CCT TGT GGA CTC GTT CGG
              oAE5B   A AAA CGA CAC AAA GAT GCT GTg GAA GCC TTC TTC GGA GGA GCT GGA ATG AAA TAT GGT GTG
TTT GCT GTG TTT CTA CGA CAc CTT CGG AAG AAG CCT CCT CGA CCT TAC TTT ATA CCA CAC
                      T                oAE3A GAA ACT GAT TGG CCT GCA TAT ATT GAA GGA TGG AAA AAA TTG GCT ACT GAT GAA TTG GAG
CTT TGA CTA ACC GGA CGT ATA TAA CTT CCT ACC TTT TTT AAC CGA TGA CTA CTT AAC CTC
```

-continued

```
     oAE5C      G    T   A
AAA TAC GCC AAA AAC GAA CCA ACc CTC ATC CGc ATc TGG GGT GAT GCT TTG TTT GAT ATC
TTT ATG CGG TTT TTG CTT GGT TGg GAG TAG GCg TAg ACC CCA CTA CGA AAC AAA CTA TAG
                             C      A   T  oAE3B

GTT GAC AAA GAT CAA AAT GGA GCT ATT ACA CTG GAT GAA TGG AAA GCA TAC ACC AAA GCT
CAA CTG TTT CTA GTT TTA CCT CGA TAA TGT GAC CTA CTT ACC TTT CGT ATG TGG TTT CGA

GCT GGT ATC ATC CAA TCA TCA GAA GAT TGC GAG GAA ACA TTC AGA GTG TGC GAT ATT GAT
CGA CCA TAG TAG GTT ACT ACT CTT CTA ACG CTC CTT TGT AAG TCT CAC ACG CTA TAA CTA
                                          oAE5D     A    TA

GAA AGT GGA CAA CTC GAT GTT GAT GAG ATG ACA AGA CAg CAT cTg GGA TTT TGG TAC ACC
CTT TCA CCT GTT GAG CTA CAA CTA CTC TAC TGT TCT GTc GTA gAc CCT AAA ACC ATG TGG
                                             T       A T       oAE3C

XhoI
ATG GAT CCT GCT TGC GAA AAG CTC TAC GGT GGA GCT GTC CCC TAA TCTcGAGGATCTTT 3'
TAC CTA GGA CGA ACG CTT TTC GAG ATG CCA CCT CGA CAG GGG ATT AGAgCTCCTAGAAA 5'
                                                              T      oAE3D
```

(SEQ ID NO: 41)

Stage 4: pGCA (Insertion of an Intercalated sequence)

In the pEGFPmur-Aeq plasmid, a sequence of five amino acids exists between the coding phases of the GFP and aequorin. Observations led to the lengthening of this region by intercalating a sequence in the BspEL site. Two complementary oligonucleotides coding for a sequence of nine amino acids give the composition a good deal of flexibility, owing to the abundance of Glycine and Serine. After insertion, the BspEI site is preserved on only one side although new intercalated sequences may be added successively. At each stage, the orientation is controlled by the BspEI enzyme. Two copies of this sequence are needed to restore the normal fluorescence of GFP, but the energy transfer between aequorin and GFP is optimal with five copies. The entire intercalated sequence of pGCA plasmid (5×9 aa +the five initial amino acids=50 aa) was verified by sequencing:

```
    Lys Ser Gly Leu Arg Ser Val
5'  AAG TCC GGA CTC AGA TCT GTC 3'
3'  TTC AGG CCT GAG TCT AGA GAG 5'
    GFP BspEI       BGlII   Aeq
              ⇓
5'  AAG T    GC GGA CTC AGA TCT GTC 3'
3'  TTC AGG CC    T GAG TCT AGA GAG 5'
                   +
        Gly Gly Ser Gly Ser Gly Gly Gln Ser
5'  CC  GGC GGG AGC GGA TCC GGC GGC GAG    T 3'
3'      G   CCC TCG CCT AGG CCG CCG GTC AGG CC 5'
                    BamHI                 BspEI
```

(SEQ ID NOS 43, 42, 44-45, 44, 47, 46 and 48, respectively, in order of appearance)

Optimization of the energy transfer by inserting a spacer between GFP and Apoaequorin.

A non-radiative energy transfer between the excited oxyluciferin and the GFP chromophore will be strongly dependent upon their overall geometry and their respective motions. Therefore, a linker was designed principally composed of serine and glycine residues to intercalate a flexible element of variable length.

Figure 2A:
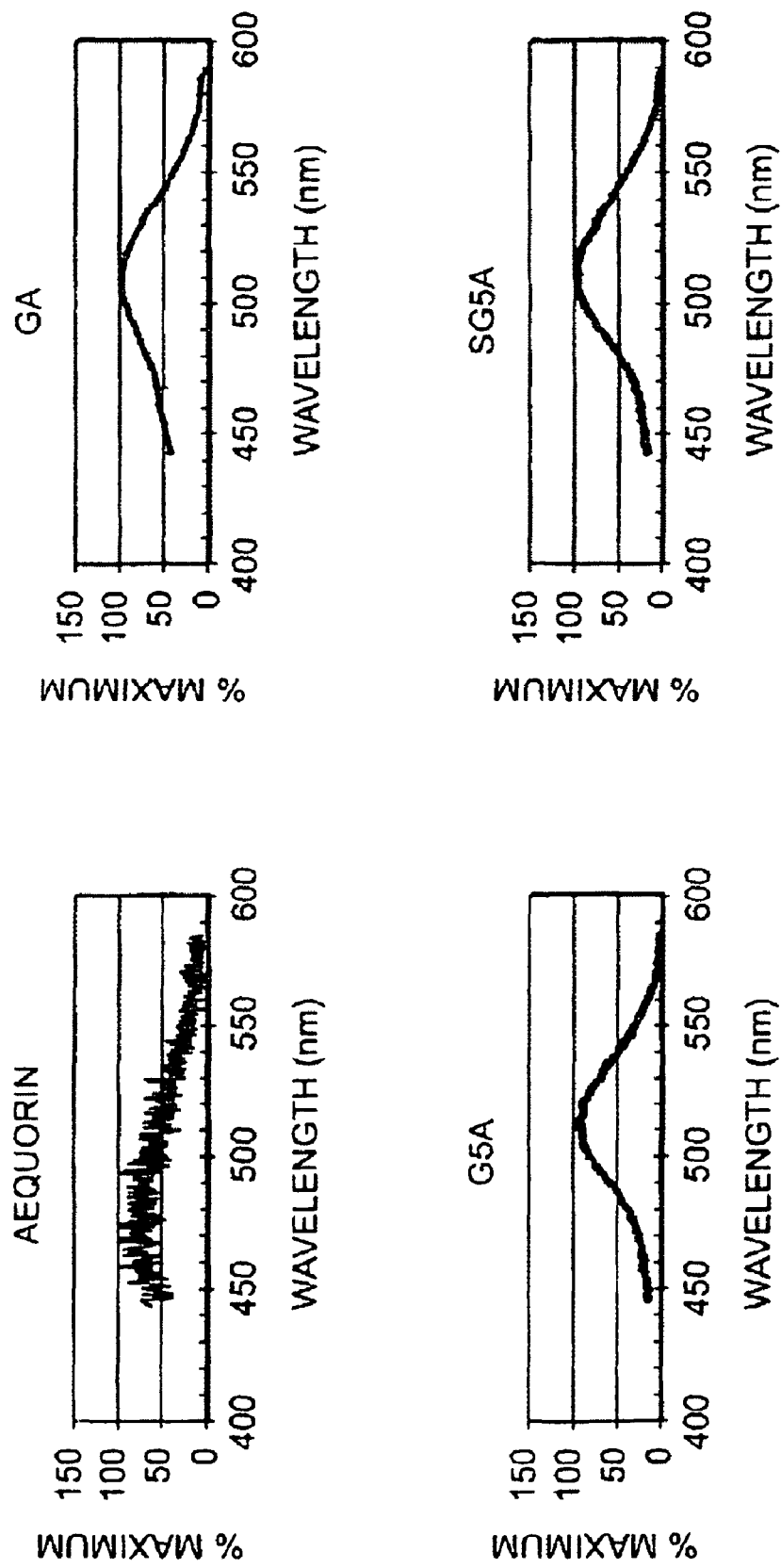
FIG. 2A and FIG. 2B depicts $Ca^{++}$ CRET activities on cellular extracts.
Figure 2B:
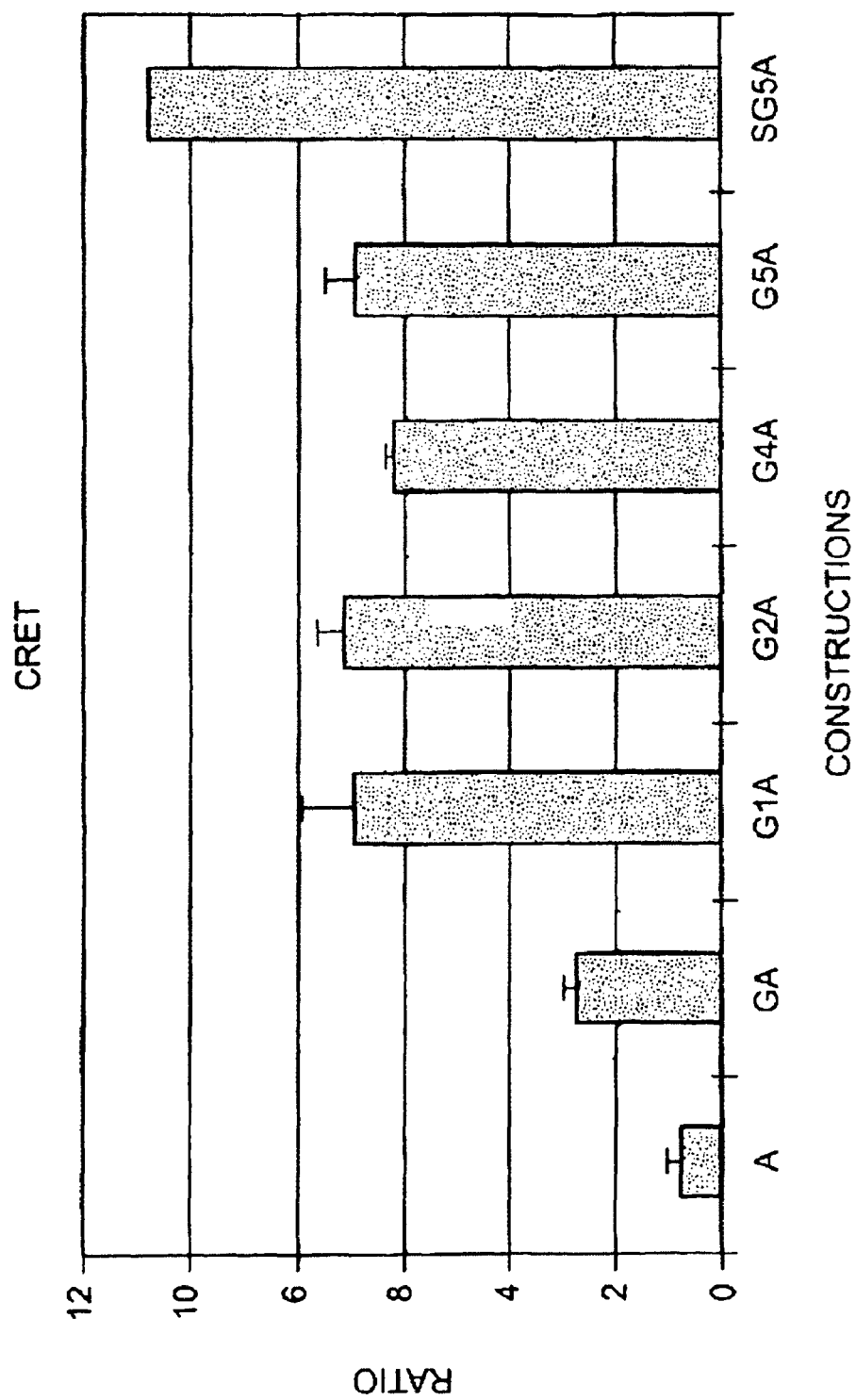

The ratio of green and blue photons emitted upon $Ca^{++}$ triggering has been measured on cellular extracts prepared 48 h after transient transfection of Neuro2A cells. The photons emitted through a beam-splitter were counted after passing appropriate filters. Covalent linking of GFP to aequorin (GA) significantly modified the wavelength of maximum light emission (FIG. 2), thereby demonstrating intramolecular energy transfer. The ratio of green over blue light (500/450 mm) was further raised from 3 to around 7 by adding 1 to 5 linkers (FIG. 2, CRET). Preliminary measurement indicates that this ratio can reach almost 11 with SG5A probably because of the accumulation of the fusion protein anchored to the membranes (see materials and methods).

Spectral emissions of the different constructs were also analyzed using a monochromator. Aequorin showed a broad spectrum with maximum wavelength at 474±6.9 nm and a bandwidth, corresponding to the distance between low and high wavelengths at 50% values of the maximum emission, at 108.3±20.1 nm (FIG. 2). There was a clear shift toward the green in the peak emission of the GFP-aequorin constructions ranging from 506.7±1.2 nm to 514.1+3.4 nm. Increasing the length of the linker further affected the sharpness of the spectrum as indicated by the narrower bandwidths, 88.4+9.4 nm and 56.0±3.3 nm, for pGA and pG5A respectively. There was no evidence of a bimodal spectrum with any of the pG1A-pG5A constructs indicating an optimal transfer which could be incomplete in the case of pGA When the spacer between GFP and aequorin is longer than 14 amino acids, the donor and the acceptor dipoles have probably more freedom to be in a configuration favourable for optimum intramolecular energy transfer. The system of the invention yields an efficiency comparable to the intermolecular CRET measured in vivo (22, 23) and provides a convenient model for the biophysical studies of radiationless energy transfer mechanisms.

Cellular localization and targeting of GFP-Apoaequorin.

The cellular localization of the GFP-apoaequorin constructs has been examined. FIG. 3 illustrates GFP activity 48 h after transient transfection in Neuro2A cells. Expression of the mutant GFP alone (Gm) showed homogenous fluorescence in the cytosol as well as in the nucleus as expected since GFP is a small protein that can diffuse into the nucleus. Mutation V163A improves remarkably the fluorescence signal and reduces photobleaching when compared to the original EGFP (data not shown) probably owing to a higher concentration of properly folded protein. An evenly distribution is also observed for all the GFP-apoaequorin constructions in Neuro2A cells (FIG. 3A-D) as well as in COS-7 cells. Bright spots often appeared in the cytosol with fusion proteins having the shortest linkers: GA, G1A and G2A. These spots were less frequent with G4A and never observed with Gm and G5A High concentrations of proteins expressed during transient transfections could induce the aggregation of GFP (24), which is also going to be influenced by the presence of the aequorin protein and the distance separating them.

The GFP-apoaequorin has also been targeted to the neurotransmitter vesicles with a complete or a partial synaptotagmin I molecule. Synaptotagmin I is a transmembrane protein of synaptic vesicles and is implicated in neurotransmitter exocytosis (25). For imaging calcium microdomains in presynaptic compartments, the signal should be more accurate than if evenly distributed in the cytoplasm of neurons. In a three part fusion protein, SG5A (FIG. 1), the complete coding sequence of synaptotagmin I has been put in frame upstream of G5A. In this case, GFP fluorescence is superimposable with synaptotagmin immunostaining but is also visible at the cellular surface (FIG. 3E). In neurons (26) and in Neuro2A cells, synaptotagmin I is localized in neuronal processes, but is undetectable in plasma membranes, probably because the dynamic mechanisms of exocytosis are followed by rapid endocytosis. When GFP-apoaequorin is fused with only the N-terminal part of synaptotagmin including the transmembrane domain but lacking the cytoplasmic domain (tSG5A, FIG. 1), a strong fluorescence is restricted to the cytosol (FIG. 3F). The punctate labeling suggests that this protein is locked into the trans-golgi system. The correct targeting of the three part fusion molecule of the invention does not occur with tSG5A and appears to be slowed down in the case of SG5A When fused to the complete synaptotagmin protein, the bioluminescent marker is held back in the plasma membrane, but nevertheless labels all neurite outgrowths present in Neuro2A cells.

$Ca^{++}$ detection in single cells.

Neuro2A cells were transiently transfected with pA, pGA, pG2A, pG5A or cotransfected with pA and pGm (FIG. 1). After aequorin reconstitution with native coelenterazine in $Ca^{++}$-free buffer, an emission of photons has been measured with a classical intensified CCD camera upon the addition of CaC12 solution (5 mM) (FIG. 4A.1 and 4A.4). With the negligible background (FIG. 4A.2), integration time of 1 second is enough to record the signal in single cells (FIG. 4A.1) expressing any of the fusion proteins. No signal could be visualized with aequorin alone or with co-expressed free GFP (data not shown). The presence of unbound GFP does not improve aequorin chemiluminescence as we observed in vitro. Because of the low level of light produced, aequorin expressed in situ has never been detected in single cells except when targeted in mitochondria With a cooled intensified CCD camera, Rutter et al. (1996) (27) have succeeded in detecting intramitochondrial $Ca^{++}$ signals when aequorin is fused to cytochrome c oxidate. Transgenes encoding cytoplasmic aequorin can report calcium activities in monolayers of cells only when photomultipliers (PMT) are used, which are more sensitive but lack the spatial resolution for single cell analysis. The stability of GFP-aequorin fusions of the invention and the improved light emission have made it possible to detect physiological $Ca^{++}$ signals at the level of single cells.

Calcium deficiency prior to measurements or the transfection conditions used may induce cellular depolarization, such that opening of the voltage dependent $Ca^{++}$ channels is likely to be responsible for the fast bioluminescent response to $CaCl_2$, addition (FIG. 4A). Light emission would then return to background level because of the desensitization of $Ca^{++}$ channels and the membrane depolarization by $Ca^{++}$-dependent K' channels (28). Fluo-3 showed a similar profile in mock transfections of Neuro2A cells (FIG. 4C). Subsequent addition of a $Ca^{++}$ ionophore (A233187) induced a second emission of photons with comparable intensity but with different kinetics. A lower light intensity is detectable in Neuro2A cells transfected with pSG5A (FIG. 4B). When a fluorescent calcium probe is anchored to the inner surface of the membrane, the response kinetics are much quicker than when the probe is not targeted (29). The use of the bioluminescent reporter SG5A probably requires a system with higher spatial and temporal resolutions. In any case, the responses observed are not due to the complete consumption of aequorin as more bioluminescence can still be observed when a concentrated Cam solution (100 mM) is applied to cells (see FIG. 4B for example). For each construction, measurements have been repeated at least 4 times. A variability of individual cells responses was observed, probably due to cell population heterogeneity. Further investigations are required to calibrate relative light unit (RLU) versus $Ca^{++}$ concentrations. Patch-clamp techniques will also allow the identification of the type of calcium channels implicated in these responses and the effect of cellular transfection on membrane potential.

The transgenes of the invention should permit imaging of electrical activity in neural networks in whole animals. In vitro, two approaches were used until recently. The first method is based on the coupling of exocytosis to emission of light from synaptolucins in nerve cells (30). Light emission occurs when the luciferase, targeted inside the synaptic vesicles, reacts with ATP in the extracellular space. With this system, the authors obtain signals correlated with the neurotransmitter release but the low light level requires very long acquisition times (over 30 sec). In the second approach, fluorescence Ca sensitive markers have been used for measurements of intracellular $[Ca^{++}]$ by FRET (3, 4, 31). For single cell detection, this technique requires a sufficient concentration of probe to discriminate the signal from the background which is generated by autofluorescence of biological compounds and the possibility of calcium-independent energy transfer between the two GFPs. The integration times are also relatively long, between 4 and 20 seconds.

This invention thus provides new bifunctional hybrids in which expression patterns can be followed by GFP fluorescence while the aequorin moiety is the reporter of Cam activity. Furthermore, the functional coupling of the two components, which follows the CRET principle, results in a higher amount of light emission and a greater $Ca^{++}$ sensitivity. Bioluminescent activities of these genetic markers have been assessed in single cells with a cooled intensified CCD camera in 1 second integration times. The recent development of low level light detection systems should allow detection of CRET signals with much shorter integration times and higher spatial resolution. Intracellular and intercellular $Ca^{++}$ signaling can be approached in vivo in transgenic animals in which the GFP-aequorin is targeted to a particular cell population and/or to specific subcellular compartments. Particularly, calcium oscillations can then be imaged simultaneously in cells of an integrated neural circuitry in real time.

This invention will be described in greater detail in the following Examples.

EXAMPLE 1

Construction of GFP-aequorin Fusion Proteins

All the constructs were made in the pEGFP-Cl vector (Clontech). The EGFP gene is codon-optimized for maximal expression in mammalian cells. It also contains 2 mutations in the chromophore, F64L and S65T, which modify the excitation spectra and enhance fluorescence intensity (17). Valine 163 of the EGFP was also substituted by alanine, using single strand mutagenesis, to improve the proper folding of the protein and increase the fluorescence at 371C (18, 19). The aequorin coding sequence, a generous gift by M.-T. Nicolas, has been fused in frame at the 3' end of the EGFP gene in the BglII/SalI sites of pEGFP-Cl. Seven codons were modified for a better expression in mammalian cells by means of site-directed mutagenesis using PCR (polymerase chain reaction) with overlap extension. Then, complementary oligonucleotides, 5'-CCGGCGGGAGCGGATCCGGCGGCCAGT-3' [SEQ ID NO: 23] and 5'-CCGGACTGGCCGCCGOATC-CGCTCCCG-3' [SEQ ID NO: 24] were inserted at the BspEI site in the 15 bp sequence between GFP and aequorin. Conservation of the BspEI site at only one end allowed sequential addition of one to five linker sequences (pG1A-pG5A).

Two additional fusion constructs were made in pG5A with a synaptic protein, synaptotagmin I of which the cDNA plasmid was generously gift by M Fukuda. Sequences encoding for either the entire open reading frame or the first 134 N-terminal amino acids, comprising the transmembrane domain of the protein, were fused in frame at the 5' end of the GFP-aequorin gene.

EXAMPLE 2

Cell Culture and Transfection

Neuroblastoma cells (Neuro2A, mouse) were grown in Dulbecco's Eagle medium (Life Technologies—Gibco, UK) supplement with 10% (V/V) heat-treated foetal calf serum, 2 mm glutamine (Life Technologies—Gibco, UK) and 100 units streptomycin-penicillin (Life Technologies—Gibco, UK). The culture were incubated at 37° C. in a humidified atmosphere containing 8% CO2 and transiently transfected using either the $CaPO_4$, technique or the FUGENE 6™ transfection reagent (Roche).

EXAMPLE 3

In vitro Ca++ Sensitive Chemiluminescence and CRET Activities

Cells were harvested 48 h after transfection in 250 gl of 10 mM β-mercaptoethanol, 4 mM EDTA, 5 µM coelenterazine in PBS at 4° C. during 2 to 4 hours. Cells were rinsed in 1 mM EDTA in PBS and harvested in 400 µl of hypo-osmotic buffer (20 mM Tris-HCl pH 7.5/5 mM EDTA/5 mM β-mercaptoethanol with a protease inhibitor cock-ail according to the manufacturer, Roche), for 30 min. to 1 h. at 4° C. The cell membranes were broken by passing through a 30 gauge needle and the cellular extract was obtained after microcentrifugation at 13000 rpm for 1 h at 40° C. The supernatant was harvested for all constructions but SG5A for which the membrane pellet was further resuspended Calcium sensitivity chemiluminescent activity was measured in a luminometer (Lumat LB95501 E&EG Berthold). Aliquots (10 µl) were placed in sample tube (with 90 µl of 10 mM Tris-HCl pH 7.5) in the luminometer and the light intensity expressed in relative light unit (R.L.U.) was measured after the injection of 100 µl of 50 mM $CaCl_2$/1 mM Tris-HCl pH 7.5 solution.

For CRET measurements, aliquots of extracts from transfected cells were placed in a reservoir chamber and brought into contact with an optic fibre bundle attached to a photon counting camera (Photek three-microchannel plate intensified CCD camera: Photek 216). Before capture of signals, light passes through a monochromator allowing the spectral analysis of emitted photons. The acquisition begins 20 seconds before injection of $CaCl_2$ and carries on during 40 seconds after injection of the $CaCl_2$ solution (50 mM). For green/ blue photons ratio determinations, the same procedure was followed but in this case the system measures the light emitted through blue (450 nm) and green (500 nm) filters after a beam splitter.

EXAMPLE 4

GFP Fluorescence and Immunolocalization

Neuro2A cells were fixed 48 h after transfection in 4% paraformaldehyde in PBS pH 7.4, rinsed in PBS, and mounted. GFP fluorescence is visualized under a confocal Laser Scanning microscope (Zeiss, Heidelberg, Germany) which uses an argon-krypton laser operating in multi-line mode or an AXIOPHOT® microscope with an epiluminescent system (Zeiss, Heidelberg, Germany). For immunolocalisation of the targeted GFP-aequorin, fixed cells were pretreated with 50 mM NH 4 Cl in PBS pH 7.4 for 5 min. at room temperature, permeabilised in 2% BSA/0.02% TRITON® (polyoxyethylene octyl phenyl ether)/goat serum solution in PBS during 1 h. Antibodies against synaptotagmin (STRESSGEN® SYA-130) were then applied during 24 hrs. Cells were then rinsed in PBS and incubated in 2% BSA/0.02% TRITON® in PBS with secondary antibody diluted at $^1/_{100}$ (RIOC conjugated antibody). Cells were then washed in PBS and mounted.

EXAMPLE 5

Single Cells Bioluminescence Detection

Forty-eight hours after transfection, cells were rinsed in 124 mM NaCl 5 mM KCl/15 mM Hepes pH 7.4/5 mM $NaHCO_3$/1 mM $NaH_2PO_4$/0.5 mM $MgSO_4$/1. 5 mM $CaCl_2$ / 5.5 mM Glucose and later incubated in the same buffer without $CaCl_2$ with 5 µM coelenterazine to reconstituted aequorin, for 2 to 4 h at 37° C. and then rinsed. Calcium signals were visualized with a modified Olympus upright microscope (BHS) fitted with an BH2-RFCA epifluorescence unit recorded through a plan x40 Olympus long working distance water-immersion lens (N.A. 0.7). GFP Fluorescence allowed to choose the recording area on transfected cells. The excitation lamp was shut off and the gain of the camera increased. Images were integrated every second with a cooled Photonic Science extended ISIS video camera. Each profile in FIG. 4 represents the amount of light emitted over the area that we defined around the soma of individual cells using the Axon Imaging Workbench 2214 software. Intensities of fluorescence and CRET activity are translated in scaled pseudocolors. Controls were made with Fluo-3 AM on mock-transfected Neuro2A cells to check the experimental conditions.

EXAMPLE 6

Protein Stability

The turnover times of the different cytosolic proteins were estimated on transient expression in COS7 cells by treatment with puromycin (50 µg/ml) for 6 h. $Ca^{2+}$-induced chemiluminescence activities were performed on cellular extra obtained after the reconstitution of aequorin in presence of 5 µM coelenterazine. Calcium sensitivity chemiluminescence activity was measured in a luminometer (Lumat LB95501 E&EG Berthold). Aliquots (10 µl) were placed in a sample tube (with 90 µl of 10 mM Tris-HCl, pH 7.5) in the luminometer and the light intensity expressed, in relative light units (RLUs), was measured after-the injection of 100 µl of 50 mM CaCl$_2$/10 mM Tris-Hcl pH 7.5 solution. Relative chemiluminescence activities are expressed as a percentage of the activity at the time zero (100%). The results are shown in FIG. 5. As seen in FIG. 5, over this period, most fusion proteins presented 30% decrease of activity compared with the 80% loss of apoaequorin when alone.

EXAMPLE 7

Determination of the Ca++ Affinity of Aaequorin and G5A

Ca$^{2+-}$ induced chemiluminescence activities were performed on cellular extract obtained after the reconstitution of aequorin in presence of 5 µM coelenterazine. Calcium sensitivity chemiluminescence activity was measured in a luminometer (Lumat LP95501 E&EG Berthold). Aliquots (10 µl) were placed in a-sample tube (with 90 µl of 10 mM TricHCl, pH 7.5) in the luminometer and the light intensity expressed, in relative light units.(RLUs), was measured after the injection of 100 µl of different Ca/EGTA solutions. The results are shown in FIG. 6. As seen in FIG. 6, G5A gives a significant signal over background with Ca$^{2+}$ concentrations as low as 38 nM, whereas aequorin needs 28 times more calcium (1 M) to yield a comparable signal.

For Chimeric GFP-Aequorin as Bioluminescent Ca$^{2+}$ Reporters at the Single Cell Level Concerning the invention of chimeric GFP-aequorin calcium sensitive bioluminescent reporters, new applications have been developed and some preliminary datas have been obtained about sensitivity of GFP-aequorin proteins to Ca$^{2+}$ ions.

EXAMPLE 8

Ca$^{2+}$ Sensitivity of G5A and SG5A: Calibration Curves Between Bioluminescent Signals and Ca$^{2+}$ Concentrations Measurements of Ca$^{2+}$ sensitivity of two constructs G5A and SG5A were performed on cellular extracts obtained after the reconstitution of aequorin in presence of 5 µM colenterazine. Calcium chemiluminescence activity was measured in a luminometer (Lumat LB95501 E&EG Berthold). Aliquots (10 µl) were placed in a sample tube with 90 µl of 10 mM Tris.HCl pH 7.5 in the luminometer and the light intensity expressed, in relative light units (RLUs), was measured after the injection of 100 ml of different Ca/EGTA solutions (Molecular Probes Calcium Calibration Buffer Kit). FIG. 7 shows the Ca$^{2+}$ response curve of G5A, SG5A and aequorin. The curves represent the relationship between the ratio L/Lmax and [Ca2+]. L is the rate of RLUs at any given [Ca2+] and Lmax is the rate of RLUs at saturating [Ca2+]. These results show a much higher affinity for Ca$^{2+}$ of the various forms of GFP-aequorin than aequorin.

EXAMPLE 9

New Applications of GFP-Aequorin Reporters

Adenoviral vectors with GFP-aequorin were developed. Using these new constructs, dissociated neurons from rat spinal cord in culture can be transfected with higher efficiency. FIGS. 8 and 9 depict Ca 2+-induced bioluminescent signals detected at the single cell level in dissociated neuronal cells. Neuronal cells infected by adenoviral vectors with GSA (FIG. 8) or SG5A (FIG. 9) were pre-incubated with 5 µM coelenterazine in a Ca 2+-free buffer. Intensities of fluorescence and bioluminescence activity are translated in pseudocolors. Representative pictures of the chosen fields are shown after the addition of 5 mM and 2.5 mM of CaCl 2, respectively, for FIGS. 8*a-c* & 9*a* at 12 and 9 seconds. FIGS. 8*d-e* and 9*b*were obtained after addition of ionomycin and high concentration of CaCl 2 (100 mM).

EXAMPLE 10

Expression of GFP-Aequorin Reporters in vivo in *Xenopus* Embryos and Measurement of Calcium Activities Calcium signalling during early and late embryogenesis in *Xenopus* was studied FIG. 10 shows representative pattern of luminescence activity illustrating the changes in intracellular calcium during the neural induction after the injection of the GA plasmid at the one cell stage in *Xenopus* embryo. FIG. 11 shows a transgenic *Xenopus* larva with GFP-aequorin These techniques can also be employed with zebrafish and mouse transgenics. These results show that these calcium reporters can be used in a great variety of organisms or tissues to visualize calcium activity and to measure calcium concentrations.

In summary, the new linker useful for energy transfer by CRET system in a bioluminescent system has the following properties:

Forms:
Different amino acid sequences and peptide sequences of the linker are described. Its length comprises a minimal size of 4 to 9 amino acids, which can be extended by a group of 7 to 12 amino acids (in a preferred embodiment 9 amino acids). The said group is extendable to 63 amino acids, i.e., 9×6 times. The experiment was done, for example, with a peptide linker comprising 5 amino acids followed by 1 to 5 times of 9 amino acids.

Functions:
Its first function is to approach donor sites and acceptor sites of two molecules for a direct transmission of energy. This linker confers an optimal environment for energy transmission by CRET.

The second function is the stabilization of the described system by increasing the half life of aequorin because of the fusion of GFP. The aequorin is linked to the GFP, which has a half life of more than 24 hours.

Applications:
In a bioluminescent system, aptitude for protein-protein interaction.

Application of the bioluminescent system with the linker: epileptogenesis, SNC disease (visualization of the neuronal cell activities during development and in the adult), neuromuscular connection with the implication of homeogene HOX-C8 in the spinal cord.

Application in apoptosis with a chimeric protein comprising the linker according to the invention by the visualization of the modifications of the intracellular calcium pools.

Visualization and precision of the role of calcium waves in living organs like the spleen (intra and intercellular calcium waves).

Results:
Chimeric protein is more stable by augmentation of the half-life of the molecule. Augmentation of the sensitivity for calcium ions is important The linker of the invention has surprising properties. The sensitivity of calcium ions of the chimeric molecule containing the aequorin and the linker is different from that for aequorin alone. The invention provides a better sensitivity.

This linker makes it possible to attach together an aequorin molecule-with a GFP. The following reference demonstrates that the both molecules do not interact together without a linker: Morise, H. Shimomura, O., Johonson, F. R and Winant, J. (1974) Intermolecular Energy Transfer in the bioluminescent system of Aequori& Biochemistry 13, 2656-2662.

It is the first time that one can obtain visulization of aequorin signal in a live single cell system (or in an alive animal).

In summary, monitoring calcium fluxes in real time could help to understand the development, the plasticity and the functioning of the central nervous system. In jellyfish, the chemiluminescent calcium binding aequorin protein is associated with the green fluorescent protein (GFP) and a green bioluminescent signal is emitted upon $Ca^{++}$ stimulation. We decided to use this Chemiluminescence Resonance Energy Transfer (CRET) between the two molecules. Calcium sensitive bioluminescent reporter genes have been constructed by fusing GFP and aequorin resulting in much more light being emitted Chemiluminescent and fluorescent activities of these fusion proteins have been assessed in mammalian cells. Cystosolic $Ca^{++}$ increases were imaged at the single cell level with a cooled intensified CCD camera. This bifunctional reporter gene should allow the investigation of calcium activities in neuronal networks and in specific subcellular compartments in transgenic animals.

Following are sequences and the corresponding sequence identifiers referred to herein:

Peptide sequences:

GA

[SEQ ID NO: 1]
M S K G E E L F T G V V P I L V E L D G D V N G H
K F S V S G E G E G D A T Y G K L T L K F I C T T
G K L P V P W P T L V T T L T Y G V Q C F S R Y P
D H M K Q H D F F K S A M P E G Y V Q E R T I F F
K D D G N Y K T R A E V K F E G D T L V N R I E L
K G I D F K E D G N I L G H K L E Y N Y N S H N V
Y I M A D K Q K N G I K A N F K I R H N I E D G S
V Q L A D H Y Q Q N T P I G D G P V L L P D N H Y
L S T Q S A L S K D P N E K R D H M V L L E F V T
A A G I T H G M D E L Y K S G L R S V K L T S D F
D N P R W I G R H K H M F N F L D V N H N G K I S
L D E M V Y K A S D I V I N N L G A T P E Q A K R
H K D A V E k F F G G A G M K Y G V E T D W P A Y
I E G W K K L A T D E L E K Y A K N E P T L I R I
W G D A L F D I V D K D Q N G A I T L D E W K A Y
T K A A G I I Q S S E D C E E T F R V C D I D E S
G Q L D V D E M T R Q H L G F W Y T M D P A C E K
L Y G G A V P

G1A

[SEQ ID NO: 2]
M S K G E E L F T G V V P I L V E L D G D V N G H
K F S V S G E G E G D A T Y G K L T L K F I C T T
G K L P V P W P T L V T T L T Y G V Q C F S R Y P
D H M K Q H D F F K S A M P E G Y V Q E R T I F F
K D D G N Y K T R A E V K F E G D T L V N R I E L
K G I D F K E D G N I L G H K L E Y N Y N S H N V
Y I M A D K Q K N G I K A N F K I R H N I E D G S
V Q L A D H Y Q Q N T P I G D G P V L L P D N H Y
L S T Q S A L S K D P N E K R D H M V L L E F V T
A A G I T H G M D E L Y K S G G S G S G G Q S G L
R S V K L T S D F D N P R W I G R H K H M F N F L
D V N H N G K I S L D E M V Y K A S D I V I N N L
G A T P E Q A K R H K D A V E A F F G G A G M K Y
G V E T D W P A Y I E G W K K L A T D E L E K Y A
K N E P T L I R I W G D A L F D I V D K D Q N G A
I T L D E W K A Y T K A A G I I Q S S E D C E E T
F R V C D I D E S G Q L D V D E M T R Q H L G F W
Y T M D P A C E K L Y G G A V P

G2A

[SEQ ID NO: 3]
M S K G E E L F T G V V P I L V E L D G D V N G H
K F S V S G E G E G D A T Y G K L T L K F I C T T
G K L P V P W P T L V T T L T Y G V Q C F S R Y P
D H M K Q H D F F K S A M P E G Y V Q E R T I F F
K D D G N Y K T R A E V K F E G D T L V N R I E L
K G I D F K E D G N I L G H K L E Y N Y N S H N V
Y I N A D K Q K N G I K A N F K I R H N I E D G S
V Q L A D H Y Q Q N T P I G D G P V L L P D N H Y
L S T Q S A L S K D P N E K R D H M V L L E F V T
A A G I T H G H D E L Y K S G G S G S G G Q S G G
S G S G G Q S G L R S V K L T S D F D N P R W I G
R H K H M F N F L D V N H N G K I S L D E N V Y K
A S D I V I N N L G A T P E Q A K R R K D A V E A
F F G G A G M K Y G V E T D W P A Y I E G W K K L
A T D E L E K Y A K N E P T L I R I W G D A L F D
I V D K D Q N G A I T L D E W K A Y T K A A G I I
Q S S E D C E E T F R V C D I D E S G Q L D V D E
M T R Q H L G F W Y T M D P A C E K L Y G G A V P

-continued

G4A

[SEQ ID NO: 4]

NSKGEELFTGVVPILVELDGDVNGH
KFSVSGEGEGDATYGKLTLKFICTT
GKLPVPWPTLVTTLTYGVQCFSRYP
DHMKQHDFFKSAMPEGYVQERTIFF
KDDGNYKTRAEVKFGDTLVNRIELK
GIDFKEDGNILGHKLEYNYNSHNVY
IMADKQKNGIKANFKIRHNIEDGSV
QLADHYQQNTPIGDGPVLLPDNHYL
STQSALSKDPNEKRDHMVLLEFVTA
AGITHGMDELYKSGGSGSGGQSGGS
GSGGQSGGSGSGGQSGGSGSGGQSG
LRSVKLTSDFDNPRWIGRHKHMFNF
LDVNHNGKISLDEMVYKASDIVINN
LGATPEQAKRHKDAVEAFFGGAGMK
YGVETDWPAYIEGWKKLATDELEKY
AKNEPTLIRIWGDALFDIVDKDQNG
AITLDEWKAYTKAAGIIQSSEDCEE
TFRVCDIDESGQLDVDEMTRQHLGF
WYTMDPACEKLYGGAVP

G5A

[SEQ ID NO: 5]

MSKGEELFTGVVPILVELDGDVNGH
KFSVSGEGEGDATYGKLTLKFICTT
GKLPVPWPTLVTTLTYGVQCFSRYP
DHMKQHDFFKSAMPEGYVQERTIFF
KDDGNYKTRAEVKFGDTLVNRIEL
KGIDFKEDGNILGHKLEYNYNSHNV
YIMADKQKNGIKANFKIRHNIEDGS
VQLADHYQQNTPIGDGPVLLPDNHY
LSTQSALSKDPNEKRDHMVLLEFVT
AAGITHGMDELYKSGGSGSGGQSGG
SGSGGQSGGSGSGGQSGGSGSGGQS
GGSGSGGQSGLRSVKLTSDFDNPRW
IGRHKHMFNFLDVNHNGKISLDEMV
YKASDIVINNLGATPEQAKRHKDAV
EAFFGGAGMKYGVETDWPAYIEGWK
KLATDELEKYAKNEPTLIRIWGDAL
FDIVDKDQNGAITLDEWKAYTKAAG
IIQSSEDCEETFRVCDIDESGQLDV
DEMTRQHLGFWYTMDPACEKLYGGA
VP

SeG5A

[SEQ ID NO: 6]

MVSASRPEALAAPVTTVATLVPHNA
TEPASPGEGREDAFSKLQKFMNEL
EKIPLPPWALIAIAIVAVLLVVTCC
FCVCKKCLFKKKNKKKGEKGGKNA
INMKDVKDLGKTNKDQALKDDDAET
GLTDGEEKEEPREEEKLGKLQYSLD
YDFQNNQLLVGIIQAAELPALDMGG
TSDPYVKVFLLPDKKKKFETKVHRK
TLNPVFNEQFTFKVPYSELGGKTLV
NAVYDFDRFSKHDIIGEFKVPMNTV
DFGHVTEEWRDLQSAEKEEQEKLGD
ICFSLRYVPTAGKLTVVILEAKNLK
KMDVGGLSDPYVKIHLMQNGKRLKK
KKTTIKKNTLNPYYNESFSFEVPFE
QIQKVQVVVTVLDYDKIGKNDAIGK
VFVGYNSTGAELRHWSDNLANPRRP
IAQWHTLQVEEEVDAMLAVKRSGNS
GRATMSKGEELFTGVVPILVELDGD
VNGHKFSVSGEGEGDATYGKLTLKF
ICTTGKLPVPWPTLVTTLTYGVQCF
SRYPDHMKQHDFFKSAMPEGYVQER
TIFFKDDGNYKTRAEVKFGDTLVN
RIELKGIDFKEDGNILGRKLEYNYN
SHNVYIMADKQKNGIKANFKIRHNI
EDGSVQLADHYQQNTPIGDGPVLLP
DNHYLSTQSALSKDPNEKRDHMVLL
EFVTAAGITHGMDELYKSGGSGSGG
QSGGSGSGGQSGGSGSGGQSGGSGS
GGQSGGSGSGGQSGLRSVKLTSDFD
NPRWIGRHKHIIFNFLDVNHNGKIS
LDEMVYKASDIVINNLGATPEQAKR
HKDAVEAFFGGAGMKYGVETDWPAY
IEGWKKLATDELEKYAKNEPTLIRI
WGDALFDIVDKDQNGAITLDEWKAY
TKAAGIIQSSEDCEETFRVCDIDES
GQLDVDEMTRQELGFWYTMDPACEK
LYGGAVP

GA

[SEQ ID NO: 7]

Atg agc aag ggc gag gag ctg ttc acc ggg gtg gtg
ccc atc ctg gtc gag ctg gac ggc gac gta aac ggc
cac aag ttc agc gtg tcc ggc gag ggc gag ggc gat
gcc acc tac ggc aag ctg acc ctg aag ttc atc tgc
acc acc ggc aag ctg ccc gtg ccc tgg ccc acc ctc
gtg acc acc ctg acc tac ggc gtg cag tgc ttc agc
cgc tac ccc gac cac atg aag cag cac gac ttc ttc
aag tcc gcc atg ccc gaa ggc tac gtc cag gag cgc
acc atc ttc ttc aag gac gac ggc aac tac aag acc
cgc gcc gag gtg aag ttc gag ggc gac acc ctg gtg
aac cgc atc gag ctg aag ggc atc gac ttc aag gag
gac ggc aac atc ctg ggg cac aag ctg gag tac aac
tac aac agc cac aac gtc tat atc atg gcc gac aag
cag aag aac ggc atc aag gCC aac ttc aag atc cgc
cac aac atc gag gac ggc agc gtg cag ctc gcc gac
cac tac cag cag aac acc ccc atc ggc gac ggc ccc
gtg ctg ctg ccc gac aac cac tac ctg agc acc cag
tcc gcc ctg agc aaa gac ccc aac gag aag cgc gat
cac atg gtc ctg ctg gag ttc gtg acc gcc gcc ggg
atc act cAc ggc atg gac gag ctg tac aag tcc gga
ctc aCA TCT gtc aaa ctt aca tca gac ttc gac aac
cca aga tgg att gga cga cac aag cat atg ttc aat
ttc ctt gat gtc aac cac aat gga aaa atc tct ctt
gac gag atg gtc tac aag gca tct gat att gtc atc
aat aac ctt gga gca aca act gag caa gcc aaa cga
cac aaa gat gct gtG gaa gcc ttc ttc gga gga gct
gga atg aaa tat ggt gtg gaa act gat tgg cct gca
tat att gaa gga tgg aaa aaa ttg gct act gat gaa
ttg gag aaa tac gcc aaa aac gaa cca acC ctc atc
cgC ata tgg ggt gat gct ttg ttt gat atc gtt gac
aaa gat caa aat gga gct att aca ctg gat gaa tgg
aaa gca tac acc aaa gct gct ggt atc atc caa tca
tca gaa gat tgc gag gaa aca ttc aga gtg tgc gat
att gat gaa agt gga caa ctc gat gtt gat gag atg
aca aga caG cat CtG gga ttt tgg tac acc atg gat
cct gct tgc gaa aag ctc tac ggt gga gct gtc ccc

G1A

[SEQ ID NO: 8]

Atg agc aag ggc gag gag ctg ttc acc ggg gtg gtg
ccc atc ctg gtc gag ctg gac ggc gac gta aac ggc
cac aag ttc agc gtg tcc ggc gag ggc gag ggc gat
gcc acc tac ggc aag ctg acc ctg aag ttc atc tgc
acc acc ggc aag ctg ccc gtg ccc tgg ccc acc ctc
gtg acc acc ctg acc tac ggc gtg cag tgc ttc agc
cgc tac ccc gac cac atg aag cag cac gac ttc ttc
aag tcc gcc atg ccc gaa ggc tac gtc cag gag cgc
acc atc ttc ttc aag gac gac ggc aac tac aag acc
cgc gcc gag gtg aag ttc gag ggc gac acc ctg gtg
aac cgc atc gag ctg aag ggc atc gac ttc aag gag
gac ggc aac atc ctg ggg cac aag ctg gag tac aac
tac aac agc cac aac gtc tat atc atg gcc gac aag
cag aag aac ggc atc aag gCC aac ttc aag atc cgc
cac aac atc gag gac ggc agc gtg cag ctc gcc gac
cac tac cag cag aac acc ccc atc ggc gac ggc ccc
gtg ctg ctg ccc gac aac cac tac ctg agc acc cag
tcc gcc ctg agc aaa gac ccc aac gag aag cgc gat
cac atg gtc ctg ctg gag ttc gtg acc gcc gcc ggg
atc act cAc ggc atg gac gag ctg tac aag tcc ggc
ggg agc gga tcc ggc ggc cag tcc ggc ctc aGA TCT
gtc aaa ctt aca tca gac ttc gac aac cca aga tgg
att gga cga cac aag cat atg ttc aat ttc ctt gat
gtc aac cac aat gga aaa atc tct ctt gac gag atg
gtc tac aag gca tct gat att gtc atc aat aac ctt
gga gca aca cct gag caa gcc aaa cga cac aaa gat
gct gtG gaa gcc ttc ttc gga gga gct gga atg aaa
tat ggt gtg gaa act gat tgg cct gca tat att gaa
gga tgg aaa aaa ttg gCt act gat gaa ttg gag aaa
tac gcc aaa aac gaa cca acC ctc atc cgC ata tgg
ggt gat gct ttg ttt gat atc gtt gac aaa gat caa
aat gga gct att aca ctg gat gaa tgg aaa gca tac
acc aaa gct gct ggt atc atc caa tca tca gaa gat
tgc gag gaa aca ttc aga gtg tgc gat att gat gaa
agt gga caa ctc gat gtt gat gag atg aca aga caG
cat CtG gga ttt tgg tac acc atg gat cct gct tgc
gaa aag ctc tac ggt gga gct gtc ccc

G2A

[SEQ ID NO: 9]

Atg agc aag ggc gag gag ctg ttc acc ggg gtg gtg
ccc atc ctg gtc gag ctg gac ggc gac gta aac ggc
cac aag ttc agc gtg tcc ggc gag ggc gag ggc gat
gcc acc tac ggc aag ctg acc ctg aag ttc atc tgc
acc acc ggc aag ctg ccc gtg ccc tgg ccc acc ctc

```
gtg acc acc ctg acc tac ggc gtg cag tgc ttc agc
cgc tac ccc gac cac atg aag cag cac gac ttc ttc
aag tcc gcc atg ccc gaa ggc tac gtc cag gag cgc
acc atc ttc ttc aag gac gac ggc aac tac aag acc
cgc gcc gag gtg aag ttc gag ggc gac acc ctg gtg
aac cgc atc gag ctg aag ggc atc gac ttc aag gag
gac ggc aac atc ctg ggg cac aag ctg gag tac aac
tac aac agc cac aac gtc tat atc atg gcc gac aag
cag aag aac ggc atc aag gCC aac ttc aag atc cgc
cac aac atc gag gac ggc agc gtg cag ctc gcc gac
cac tac cag cag aac acc ccc atc ggc gac ggc ccc
gtg ctg ctg ccc gac aac cac tac ctg agc acc cag
tcc gcc ctg agc aaa gac ccc aac gag aag cgc gat
cac atg gtc ctg ctg gag ttc gtg acc gcc gcc ggg
atc act cAc ggc atg gac gag ctg tac aag tcc ggc
ggg agc gga tcc ggc ggc cag tcc ggc ggg agc gga
tcc ggc ggc cag tcc ggc ctc aGA TCT gtc aaa ctt
aca tca gac ttc gac aac cca aga tgg att gga cga
cac aag cat atg ttc aat ttc ctt gat gtc aac cac
aat gga aaa atc tct ctt gac gag atg gtc tac aag
gca tct gat att gtc atc aat aac ctt gga gca aca
cct gag caa gcc aaa cga cac aaa gat gct gtG gaa
gcc ttc ttc gga gga gct gga atg aaa tat ggt gtg
gaa act gat tgg cct gca tat att gaa gga tgg aaa
aaa ttg gct act gat gaa ttg gag aaa tac gcc aaa
aac gaa cca acC ctc atc cgC ata tgg ggt gat gct
ttg ttt gat atc gtt gac aaa gat caa aat gga gct
att aca ctg gat gaa tgg aaa gca tac acc aaa gct
gct ggt atc atc caa tca tca gaa gat tgc gag gaa
aca ttc aga gtg tgc gat att gat gaa agt gga caa
ctc gat gtt gat gag atg aca aga caG cat CtG gga
ttt tgg tac acc atg gat cct gct tgc gaa aag ctc
tac ggt gga gct gtc ccc
G4A
                                          [SEQ ID NO: 10]
Atg agc aag ggc gag gag ctg ttc acc ggg gtg gtg
ccc atc ctg gtc gag ctg gac ggc gac gta aac ggc
cac aag ttc agc gtg tcc ggc gag ggc gag ggc gat
gcc acc tac ggc aag ctg acc ctg aag ttc atc tgc
acc acc ggc aag ctg ccc gtg ccc tgg ccc acc ctc
gtg acc acc ctg acc tac ggc gtg cag tgc ttc agc
cgc tac ccc gac cac atg aag cag cac gac ttc ttc
aag tcc gcc atg ccc gaa ggc tac gtc cag gag cgc
acc atc ttc ttc aag gac gac ggc aac tac aag acc
cgc gcc gag gtg aag ttc gag ggc gac acc ctg gtg
aac cgc atc gag ctg aag ggc atc gac ttc aag gag
gac ggc aac atc ctg ggg cac aag ctg gag tac aac
tac aac agc cac aac gtc tat atc atg gcc gac aag
cag aag aac ggc atc aag gCC aac ttc aag atc cgc
cac aac atc gag gac ggc agc gtg cag ctc gcc gac
cac tac cag cag aac acc ccc atc ggc gac ggc ccc
gtg ctg ctg ccc gac aac cac tac ctg agc acc cag
tcc gcc ctg agc aaa gac ccc aac gag aag cgc gat
cac atg gtc ctg ctg gag ttc gtg acc gcc gcc ggg
atc act cAc ggc atg gac gag ctg tac aag tcc ggc
ggg agc gga tcc ggc ggc cag tcc ggc ggg agc gga
tcc ggc ggc cag tcc ggc ggg agc gga tcc ggc ggc
cag tcc ggc ggg aga gga tcc ggc ggc cag tcc ggc
ctc aGA TCT gtc aaa ctt aca tca gac ttc gac aac
cca aga tgg att gga cga cac aag cat atg ttc aat
ttc ctt gat gtc aac cac aat gga aaa atc tct ctt
gac gag atg gtc tac aag gca tct gat att gtc atc
aat aac ctt gga gca aca cct gag caa gcc aaa
cga cac aaa gat gct gtG gaa gcc ttc ttc gga gga
gct gga atg aaa tat ggt gtg gaa act gat tgg cct
gca tat att gaa gga tgg aaa aaa ttg gct act gat
gaa ttg gag aaa tac gcc aaa aac gaa cca acC ctc
atc cgC ata tgg ggt gat gct ttg ttt gat atc gtt
gac aaa gat caa aat qga gct att aca ctg gat gaa
tgg aaa gca tac acc aaa gct gct ggt atc atc caa
tca tca gaa gat tgc gag gaa aca ttc aga gtg tgc
gat att gat gaa agt gga caa ctc gat gtt gat gag
atg aca aga caG cat CtG gga ttt tgg tac acc atg
gat cct gct tgc gaa aag ctc tac ggt gga gct gtc
ccc
G5A
                                          [SEQ ID NO: 11]
Atg agc aag ggc gag gag ctg ttc acc ggg gtg gtg
ccc atc ctg gtc gag ctg gac ggc gac gta aac ggc
cac aag ttc agc gtg tcc ggc gag ggc gag ggc gat
gcc acc tac ggc aag ctg acc ctg aag ttc atc tgc
acc acc ggc aag ctg ccc gtg ccc tgg ccc acc ctc
```

-continued gtg acc acc ctg acc tac ggc gtg cag tgc ttc agc
cgc tac ccc gac cac atg aag cag cac gac ttc ttc
aag tcc gcc atg ccc gaa ggc tac gtc cag gag cgc
acc atc ttc ttc aag gac gac ggc aac tac aag acc
cgc gcc gag gtg aag ttc gag ggc gac acc ctg gtg
aac cgc atc gag ctg aag ggc atc gac ttc aag gag
gac ggc aac atC ctg ggg cac aag ctg gag tac aac
tac aac agc cac aac gtc tat atc atg gcc gac aag
cag aag aac ggc atc aag gCC aac ttc aag atc cgc
cac aac atc gag gac ggc agc gtg cag ctc gcc gac
cac tac cag cag aac acc ccc atc ggc gac ggc ccc
gtg ctg ctg ccc gac aac cac tac ctg agc acc cag
tcc gcc ctg agc aaa gac ccc aac gag aag cgc gat
cac atg gtc ctg ctg gag ttc gtg acc gcc gcc ggc
atc act cAc ggc atg gac gag ctg tac aag tcc ggc
ggg agc gga tcc ggc ggc cag tcc ggc ggg agc gga
tcc ggc ggc cag tcc ggg agc gga tcc ggc ggc
cag tcc ggc ggg agc gga tcc ggc ggc cag tcc ggc
ggg agc gga tcc ggc ggc cag tcc ggc ctc aGA TCT
gtc aaa ctt aca tca gac ttc gac aac cca aga tgg
att gga cga cac aag cat atg ttc aat ttc ctt gat
gtc aac cac aat gga aaa atc tct ctt gac gac atg
gtc tac aag gca tct gat att gtc atc aat aac ctt
gga gca aca cct gag cac gcc aaa cga cac aaa gat
gct gtG gaa gcc ttc ttc gga gga gct gga atg aaa
tat ggt gtg gaa act gat tgg cct gca tat att gaa
gga tgg aaa aaa ttg gct act gat gaa ttg gag aaa
tac gcc aaa aac gaa cca acC ctc atc cgC ata tgg
ggt gat gct ttg ttt gat atc gtt gac aaa gat caa
aat gga gct att aca ctg gat gaa tgg aaa gca tac
acc aaa gct gct ggt atc atc caa tca tca gaa gat
tgc gag gaa aca ttc aga gtg tgc gat att gat gaa
aqt gga caa ctc gat gtt gat gag atg aca aga caG
cat CtG gga ttt tgg tac acc atg gat cct gct tgc
gaa aag ctc tac ggt gga gct gtc ccc SeG5A
[SEQ ID NO: 12]
Atg gtg agt gcc agt cgt cct gag gcc ctg gct gcc
cct gtc acc act gtt gcg acc ctt gtc cca cac aac
gcc act gag cca gcc agt cct ggg gaa ggg aag gaa
gat gcc ttt tcc aag ctg aag cag aag ttt atg aat -continued gaa ctg cat aaa atc cca ttg cca ccg tgg gcc tta
att gcc ata gcc ata gtt gcg gtc ctt cta gtc gtg
acc tgc tgc ttc tgt gtc tgt aag aaa tgt ttg ttc
aaa aag aaa aac aag aag aag gga aag gaa aag gga
ggg aag aac gcc att aac atg aaa gac gtg aaa gac
tta ggg aag acc atg aag gat cag gcc ctt aag gat
gac gat gct gaa act gga ctg act gat gga gaa gaa
aag gag gag ccc aag gaa gag gag aaa ctg gga aag
ctt caa tat tca ctg gac tat gac ttc cag aat aac
cag ctg ctg gtg gga atc atc cag gct gct gaa ctg
ccc gcc ctg gac atg gga ggc aca tct gat cca tac
gtc aaa gtc ttc ctg ctg ccc gac aaa aag aag aag
ttt gag aca aaa gtc cac cgg aaa acc ctc aat cca
gtc ttc aat gaa cag ttt act ttc aag gtg cca tac
tcg gaa tta ggt ggc aag aca ctg gtg atg gct gtg
tat gat ttt gac cgc ttc tcc aag cac gac atc att
gga gag ttc aaa gtt cct atg aac acc gtg gat ttt
ggc cac gtc acc gag gag tgg cgc gat ctc cag agt
gct gag aaa gaa gag caa gag aaa ctg ggt gac atc
tgc ttc tcc ctc cgc tac gtc Cct act gcc ggc aag
ctg act gtt gtc att ctg gaa gcc aag aac ctg aag
aag atg gat gtg qgt ggc tta tct gat ccc tat gta
aag att cac ctg atg cag aac ggc aag aga ctg aag
aag aaa aag aca acg att aag aag aac aca ctt aac
ccc tac tac aat gag tcc ttc agc ttt gaa gtt ccg
ttc gag caa atc cag aaa gtg caa gtg gtg gta act
gtt ttg gac tat gac aag att ggc aag aac gac gcc
atc ggc aaa gtc ttt gtg ggc tac aac agc acc ggc
gca gag ctg cga cac tgg tca gac atg ctg gcc aac
ccc cgg cgc ccc atc gcc cag tgg cac act ctg cag
gta gag gag gag gtt gat gcc atg ctg gct gtc aag
aGA tCC GGG AAT TCC GGG CGG gcc acc atg agc aag
ggc gag gag ctg ttc acc ggg gtg gtg ccc atc ctg
gtc gag ctg gac ggc gac gta aac ggc cac aag ttc
agc gtg tcc ggc gag ggc gag ggc gat gcc acc tac
ggc aag Ctg acc ctg aag ttc atc tgc acc acc ggc
aag ctg ccc gtg ccc tgg ccc acc ctc gtg acc acc
ctg acc tac ggc gtg cag tgc ttc agc cgc tac ccc
gac cac atg aag cag cac gac ttc ttc aag tcc gcc
atg ccc gaa ggc tac gtc cag gag cgc acc atc ttc

```
ttc aag gac gac ggc aac tac aag acc cgc gcc gag gtg aag ttc gag ggc gac acc ctg gtg aac cgc atc gag ctg aag ggc atc gac ttc aag gag gac ggc aac atc ctg ggg cac aag ctg gag tac aac tac aac agc cac aac gtc tat atc atg gcc gac aag cag aag aac ggc atc aag gCC aac ttc aag atc cgc cac aac atc gag gac ggc agc gtg cag ctc gcc gac cac tac cag cag aac acc ccc atc ggc gac ggc ccc gtg ctg ctg ccc gac aac cac tac ctg agc acc cag tcc gcc ctg agc aaa gac ccc aac gag aag cgc gat cac atg gtc ctg ctg gag ttc gtg acc gcc gcc ggg atc act cAc ggc atg gac gag ctg tac aag tcc ggc ggg agc gga tcc ggc ggc cag tcc ggc ggg agc gga tcc ggc ggc cag tcc ggc ggg agc gga tcc ggc ggc cag tcc ggc ggg agc gga tcc ggc ggc cag tcc ggc ggg agc gga tcc ggc ggc cag tcc ggc ctc aGA TCT gtc aaa ctt aca tca gac ttc gac aac cca aga tgg att gga cga cac aag cat atg ttc aat ttc ctt gat gtc aac cac aat gga aaa atc tct ctt gac gag atg gtc tac aag gca tct gat att gtc atc aat aac ctt gga gca aca cct gag caa gcc aaa cga cac aaa gat gct gtG gaa gcc ttc ttc gga gga gct gga atg aaa tat ggt gtg gaa act gat tgg cct gca tat att gaa gga tgg aaa aaa ttg gct act gat gaa ttg gag aaa tac gcc aaa aac gaa cca acC ctc atc cgc ata tgg ggt gat gct ttg ttt gat atc gtt gac aaa gat caa aat gga gct att aca ctg gat gaa tgg aaa gca tac acc aaa gct gct ggt atc atc caa tca tca gaa gat tgc gag gaa aca ttc aga gtg tgc gat att gat gaa agt gga caa ctc gat gtt gat gag atg aca aga caG cat CtG gga ttt tgg tac acc atg gat cct gct tgc gaa aag ctc tac ggt gga gct gtc ccc DNA scquence of GFP-aeguorin linkers
pGA (strain I2507)
                                              [SEQ ID NO: 13]
TCC GGC CC AGA TCT pG1A (strain I2508)
                                              [SEQ ID NO: 14]
TCC GGC GGG AGC GGA TCC GGC GGC CAG TCC GGC CTC

AGA TCT pG2A (strain I2509)
                                              [SEQ ID NO: 15]
TCC GGC GGG AGC GGA TCC GGC GGC CAG TCC GGC GGG

AGC GGA TCC GGC GGC CAG TCC GGC CTC AGA TCT pG4A (strain I2510)
                                              [SEQ ID NO: 16]
TCC GGC GGG AGC GGA TCC GGC GGC CAG TCC GGC GGG

AGC GGA TCC GGC GGC CAG TCC GGC GGG AGC GGA TCC

GGC GGC CAG TCC GGC GGG AGC GGA TCC GGC GGC CAG

TCC GGC CTC AGA TCT pG5A (strain I2511)
                                              [SEQ ID NO: 1]
TCC GGC GGG AGC GGA TCC GGC GGC CAG TCC GGC GGG

AGC GGA TCC GGC GGC CAG TCC GGC GGG AGC GGA TCC

GGC GGC GAG TCC GGC GGG AGC GGA TCC GGC GGC CAG

TCC GGC GGG AGC GGA TCC GGC GGC CAG TCC GGC CTC

AGA TCT pScG5A.(strain I2512) and pStG5A (strain I2513)
same linker sequence than pG5A.

Peptide sequence of linkers
PGA
                                              [SEQ ID NO: 18 ]
Ser Gly Leu Arg Ser
Pg1a
                                              [SEQ ID NO: 19]
Ser Gly Gly Ser Gly Ser Gly Gly Gln Ser Gly Leu Arg Ser pG2A
                                              [SEQ ID NO: 20]
Ser Gly Gly Ser Gly Ser Gly Gly Gln Ser Gly Gly Ser Gly Ser Gly Gly Gln Ser Gly Leu Arg Ser pG4A
                                              [SEQ ID NO: 21]
Ser Gly Gly Ser Gly Ser Gly Gly Gln Ser Gly Gly Ser Gly Ser Gly Gly Gln Ser Gly Gly Ser Gly Ser Gly Gly Gln Ser Gly Gly Ser Gly Ser Gly Gly Gln Ser Gly Leu Arg Ser pG5A
                                              [SEQ ID NO: 22]
Ser Gly Gly Ser Gly Ser Gly Gly Gln Ser Gly Gly Ser Gly Ser Gly Gly Gln Ser Gly Gly Ser Gly Ser
```

-continued

```
Gly Gly Gln Ser Gly Gly Ser Gly Ser Gly Gly Gln

Ser Gly Gly Ser Gly Ser Gly Gly Gln Ser Gly Leu

Arg Ser pSeG5A and pStGSA idem than pG5A.
```

REFERENCES

The following publications have been cited herein. The entire disclosure of each publication is relied upon and incorporated by reference herein.

1. Beaidge, M. J. (1998) *Neuron* 21, 13-26.
2. Cobbold, P. H., & Rink, T. J. (1987) *Biochem. J.* 248, 313-323.
3. Miyawaki, A., Griesbeck, O., Heim, R., & Tsien, R. Y. (1999) *Proc. Natl. Acad. Sci. USA* 96,2135-2140.
4. Romoser, V. A., Hinkle, P. M., & Persechini, A. (1997) *J. Biol. Chem.* 272, 13270-13274.
5. Inui, S., Noguchi, M., Sack, Y., Takagi, Y., Miyata, T., Awing, S., Miyata, T., & Tsuji, F. I. (1985) *Proc. Natl. Acad. Sci. USA* 82, 3154-3158.
6. Prasher, D., McCann, R. O., & Cormier, M. J. (1985) *Biochem. Biophys. Res. Comm* 126, 1259-1268.
7. Tsuji, F. I., Inouye, S., Goto, T., & Sakaki, Y. (1986) *Proc. Natl. Acad. Sci. USA* 83, 8107-8111.
8. Shimomura, O., & Johnson, F. H. (1978) *Proc. Natl. Acad. Sci. USA* 75, 2611-2615.
9. Sala-Newby, G. B., Badminton, M. N., Evans, W. H., Georges, C. H., Jones, H. E., Kendal, J. M., Ribeiro, A. R. & Campbell, A. K. (2000) *Method Enzymol.* 305, 479-498.
10. Shimomura, O., Johnson, F. H., & Saiga, Y. (1962) *J. Cell Comp. Physiol.* 59, 223-239.
11. Johnson, F. H., Shimomura, O., Saiga, Y., Gershman, L. C., Reynolds, G. T., & Waters, J. R. (1962) *J. Cell Comp. Physiol* 60, 85-103.
12. Cubitt, A. B., Heim, R., Adams, S. R., Boyd, A. E., Gross, L. A., & Tsien, R. Y. (1995) *Trends Biochem. Sci.,* 20, 448-455.
13. Ward, W. W., & Cormier, M. J. (1976) *J. Phys. Chem.* 80,2289-2291.
14. Ward, W. W. I & Cormier, M. J. (1978) *Pholochem. Photobiol.* 27, 389-396.
15. Morise, H., Shimomura, O., Johnson, F. H., & WinNT, J. (1974) *Biochemistry* 13, 2656-2662.
16. Campbell, A. K. (1988) in Chemiluminescence, *Principles and Application in Biology and Medecin*, eds.Ellis Horwood Ltd. (Chichester), pp 474-534.
17. Cormack, B. P., Valdivia, R. H., & Falkow, S. (1996) *Gene* 173, 33-38.
18. Crameri A., Whitehor, E. A., Tate, E., Stemmer, W. P. C. (1996) *Nature Biotech.* 14, 315-319.
19. Siemering, K. R., Golbik, R., Sever, R., & Haseloff, J. (1996) *Curr. Biol.* 6, 1653-1663.
20. Watkins, N. J., & Campbell, A. K. (1993) *Biochem. J.,* 293, 181-185.
21. Badminton, M. N., Sala-Newby, G. B., Kendall, J. M., & Campbell, A. K. (1995) *Biochem. Biophys. Res. Comm.* 217, 950-957.
22. Morin, J. G., & Hastings, J. W. (1970) *J. Cell. Physiol.* 77, 313-318.
23. Campbell, A. K., & Hallett, M. B. (1978) *Proc. Physiol. Soc.,* 287, 45.
24. Yang, F., Moss, L. G., & Phillips, Jr., G. N. (1996) *Nature Biotech.* 14, 1246-1251.
25. Brose, N., Petrenko, A. G., Sladhof T, C., & Jahn, R. (1992) *Science* 256, 1021-1025.
26. Coco, S., Verderio, C., De Camilli, P., & Matteoli, M. (1998) *J. Neurochem.* 71, 1987-1992.
27. Rutter, G. A., Burnett, P., Rizzuto, R., Brini, M., Murgia, M., Pozzan, T., Tavaré J. M. & Denton, R. M. (1996) *Proc. Natl. Acad. Sci. USA* 93, 5489-5494.
28. Sah, P. (1996) *Trends Neurosci.* 19, 150-154.
29. Etter, E. F., Minta, A., Poenie, M., & Fay, F. S. (1996) *Proc. Natl. Acad. Sci. USA* 93, 5368-5373.
30. Miesenböck, G., & Rothman, J. E. (1997) *Prod. Natl. Acad. Sci. USA* 94, 3402-3407.
31. Miyawaki, A., Llopis, J., Heim, R., McCaffery, J. M., Adams, J. A., Ikura, M., & Tsien, R. Y, (1997) *Nature* 388, 882-887.

Also incorporated by reference herein in its entirety is U.S. Pat. No. 5,683,888.

What is claimed is:

1. An isolated or purified polynucleotide encoding a peptide linker of at least 5 amino acids comprising the amino acid sequence of SEQ ID NO: 18, SEQ ID NO: 19, SEQ ID NO: 20, SEQ ID NO: 21, or SEQ ID NO: 22, wherein:

(A) the peptide linker links a donor site to an acceptor site to transmit a direct transfer of energy by chemiluminescence;

(B) the peptide linker links a donor site to an acceptor site to transmit a direct transfer of energy in the presence of a purified polypeptide;

(C) the polynucleotide encodes a fluorescent protein and a photoprotein; or (D) the polynucleotide comprises the nucleic acid sequence SEQ ID NO: 14, SEQ ID NO: 15, SEQ ID NO: 16, or SEQ ID NO: 17.

2. The isolated or purified polynucleotide of claim 1, wherein the peptide linker links a donor site to an acceptor site to transmit a direct transfer of energy by chemiluminescence.

3. The isolated or purified polynucleotide of claim 1, wherein the peptide linker links a donor site to an acceptor site to transmit a direct transfer of energy in the presence of a purified polypeptide.

4. The isolated or purified polynucleotide of claim 3, wherein the peptide linker stabilizes a modified bioluminescent system in vivo or in vitro or both in vivo and in vitro.

5. The isolated or purified polynucleotide of claim 1, wherein the polynucleotide encodes a fluorescent protein and a photoprotein.

6. The isolated or purified polynucleotide of claim 5, wherein the polynucleotide encodes aequorin.

7. The isolated or purified polynucleotide of claim 6, wherein the polynucleotide encodes green fluorescent protein.

8. The isolated or purified polynucleotide of claim 1, wherein said polynucleotide comprises the nucleic acid sequence SEQ ID NO: 14, SEQ ID NO: 15, SEQ ID NO: 16, or SEQ ID NO: 17.

9. An isolated or purified polynucleotide encoding a fusion protein for energy transfer from aequorin to green fluorescent protein by Chemiluminescence Resonance Energy Transfer (CRET) following activation of the aequorin in the presence of $Ca^{++}$, wherein the fusion protein has the formula:

GFP–LINKER–AEQ;

wherein GFP is green fluorescent protein; AEQ is aequorin; and LINKER comprises the following amino acids: (Gly Gly Ser Gly Ser Gly Gly Gln Ser [SEQ ID NO: 25])$_n$, wherein n is 1-5; and wherein the fusion protein has an affinity for $Ca^{++}$ ions and a half-life of at least 24 hours.

10. An isolated or purified polynucleotide encoding a fusion protein of the formula:

GFP–LINKER–AEQ;

wherein GFP is green fluorescent protein; AEQ is aequorin; and LINKER is a polypeptide of 5-63 amino acids;

wherein the linker includes the amino acid sequence Ser Gly Leu Arg Ser [SEQ ID NO: 26].

11. An isolated or purified polynucleotide encoding a fusion protein of the formula:

GFP–LINKER–AEQ;

wherein GFP is green fluorescent protein; AEQ is aequorin; and LINKER is a polypeptide of 9-63 amino acids;

wherein the linker comprises the following amino acids: (Gly Gly Ser Gly Ser Gly Gly Gln Ser [SEQ ID NO: 25])$_n$, wherein n is 1-5.

12. The isolated or purified polynucleotide of claim 11, wherein n is 1.

13. The isolated or purified polynucleotide of claim 11, wherein n is 5.

14. The isolated or purified polynucleotide of claim 1, wherein the polynucleotide encodes a fusion protein comprising any one of SEQ ID NOS: 1-6.

15. The isolated or purified polynucleotide of claim 14, wherein the polynucleotide comprises any one of SEQ ID NOS: 7-12.

16. An isolated or purified polynucleotide encoding a fusion protein comprising two bioluminescent proteins and a peptide linker, wherein said peptide linker comprises the amino acid sequence of SEQ ID NO: 18.

17. A kit for detecting the transfer of energy in vivo or in vitro comprising the isolated or purified polynucleotide of claims 8, 9, 10, 13, or 15, and reagents necessary for visualizing or detecting transfer of energy by Chemiluminesce Resonance Energy Transfer in the encoded fusion protein in the presence or in the absence of a molecule of interest.

18. The isolated or purified polynucleotide of claims 1, 8, 9, 10, or 11, wherein the polynucleotide further encodes a peptide signal sequence for targeting the fusion protein to a cell or a subcellular compartment.

19. A vector comprising the isolated or purified polynucleotide of any one of claim 1, 8, 9, 10, or 11.

20. An isolated or purified cell comprising the vector of claim 19.

21. An isolated or purified cell comprising a plasmid selected from: I-2507, I-2508, I-2509, I-2510, I-2511, I-2512, and I-2513.

22. An isolated or purified polynucleotide encoding a peptide linker comprising the amino acid sequence of SEQ ID NO: 19, SEQ ID NO: 20, SEQ ID NO: 21, or SEQ ID NO: 22.

* * * * *

UNITED STATES PATENT AND TRADEMARK OFFICE
CERTIFICATE OF CORRECTION

PATENT NO. : 7,763,443 B2
APPLICATION NO. : 11/149177
DATED : July 27, 2010
INVENTOR(S) : Valérie Baubet et al.

It is certified that error appears in the above-identified patent and that said Letters Patent is hereby corrected as shown below:

On the Title Page, Item (57), Abstract, lines 5-6, "Transfer(CRET)." should read --Transfer (CRET).--.

In claim 9, column 83, line 10, "$Ca^{++}$ions" should read --$Ca^{++}$ ions--.

In claim 19, column 84, line 22, "any one of claim" should read --any one of claims--.

Signed and Sealed this

Sixteenth Day of November, 2010

David J. Kappos
*Director of the United States Patent and Trademark Office*

SEQUENCE LISTING

```
<160> NUMBER OF SEQ ID NOS: 52

<210> SEQ ID NO 1
<211> LENGTH: 432
<212> TYPE: PRT
<213> ORGANISM: Aequorea victoria

<400> SEQUENCE: 1

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60
```

-continued

```
Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys Ser Gly
225                 230                 235                 240

Leu Arg Ser Val Lys Leu Thr Ser Asp Phe Asp Asn Pro Arg Trp Ile
                245                 250                 255

Gly Arg His Lys His Met Phe Asn Phe Leu Asp Val Asn His Asn Gly
            260                 265                 270

Lys Ile Ser Leu Asp Glu Met Val Tyr Lys Ala Ser Asp Ile Val Ile
        275                 280                 285

Asn Asn Leu Gly Ala Thr Pro Glu Gln Ala Lys Arg His Lys Asp Ala
290                 295                 300

Val Glu Ala Phe Phe Gly Gly Ala Gly Met Lys Tyr Gly Val Glu Thr
305                 310                 315                 320

Asp Trp Pro Ala Tyr Ile Glu Gly Trp Lys Lys Leu Ala Thr Asp Glu
                325                 330                 335

Leu Glu Lys Tyr Ala Lys Asn Glu Pro Thr Leu Ile Arg Ile Trp Gly
            340                 345                 350

Asp Ala Leu Phe Asp Ile Val Asp Lys Asp Gln Asn Gly Ala Ile Thr
        355                 360                 365

Leu Asp Glu Trp Lys Ala Tyr Thr Lys Ala Ala Gly Ile Ile Gln Ser
370                 375                 380

Ser Glu Asp Cys Glu Glu Thr Phe Arg Val Cys Asp Ile Asp Glu Ser
385                 390                 395                 400

Gly Gln Leu Asp Val Asp Glu Met Thr Arg Gln His Leu Gly Phe Trp
                405                 410                 415

Tyr Thr Met Asp Pro Ala Cys Glu Lys Leu Tyr Gly Gly Ala Val Pro
            420                 425                 430
```

<210> SEQ ID NO 2
<211> LENGTH: 441
<212> TYPE: PRT
<213> ORGANISM: Aequorea victoria

<400> SEQUENCE: 2

```
Met Ser Lys Gly Glu Glu Leu Phe Thr Gly Val Val Pro Ile Leu Val
 1               5                  10                  15
```

```
Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Leu
     50                  55                  60

Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Ser Gly
225                 230                 235                 240

Gly Ser Gly Ser Gly Gly Gln Ser Gly Leu Arg Ser Val Lys Leu Thr
                245                 250                 255

Ser Asp Phe Asp Asn Pro Arg Trp Ile Gly Arg His Lys His Met Phe
        260                 265                 270

Asn Phe Leu Asp Val Asn His Asn Gly Lys Ile Ser Leu Asp Glu Met
    275                 280                 285

Val Tyr Lys Ala Ser Asp Ile Val Ile Asn Asn Leu Gly Ala Thr Pro
290                 295                 300

Glu Gln Ala Lys Arg His Lys Asp Ala Val Glu Ala Phe Phe Gly Gly
305                 310                 315                 320

Ala Gly Met Lys Tyr Gly Val Glu Thr Asp Trp Pro Ala Tyr Ile Glu
                325                 330                 335

Gly Trp Lys Lys Leu Ala Thr Asp Glu Leu Glu Lys Tyr Ala Lys Asn
            340                 345                 350

Glu Pro Thr Leu Ile Arg Ile Trp Gly Asp Ala Leu Phe Asp Ile Val
        355                 360                 365

Asp Lys Asp Gln Asn Gly Ala Ile Thr Leu Asp Glu Trp Lys Ala Tyr
    370                 375                 380

Thr Lys Ala Ala Gly Ile Ile Gln Ser Ser Glu Asp Cys Glu Glu Thr
385                 390                 395                 400

Phe Arg Val Cys Asp Ile Asp Glu Ser Gly Gln Leu Asp Val Asp Glu
                405                 410                 415

Met Thr Arg Gln His Leu Gly Phe Trp Tyr Thr Met Asp Pro Ala Cys
            420                 425                 430
```

-continued

```
Glu Lys Leu Tyr Gly Gly Ala Val Pro
        435             440

<210> SEQ ID NO 3
<211> LENGTH: 450
<212> TYPE: PRT
<213> ORGANISM: Aequorea victoria

<400> SEQUENCE: 3

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Ser Gly
225                 230                 235                 240

Gly Ser Gly Ser Gly Gly Gln Ser Gly Gly Ser Gly Gly Gly Gln
                245                 250                 255

Ser Gly Leu Arg Ser Val Lys Leu Thr Ser Asp Phe Asp Asn Pro Arg
            260                 265                 270

Trp Ile Gly Arg His Lys His Met Phe Asn Phe Leu Asp Val Asn His
        275                 280                 285

Asn Gly Lys Ile Ser Leu Asp Glu Met Val Tyr Lys Ala Ser Asp Ile
    290                 295                 300

Val Ile Asn Asn Leu Gly Ala Thr Pro Glu Gln Ala Lys Arg His Lys
305                 310                 315                 320

Asp Ala Val Glu Ala Phe Phe Gly Gly Ala Gly Met Lys Tyr Gly Val
                325                 330                 335

Glu Thr Asp Trp Pro Ala Tyr Ile Glu Gly Trp Lys Lys Leu Ala Thr
            340                 345                 350

Asp Glu Leu Glu Lys Tyr Ala Lys Asn Glu Pro Thr Leu Ile Arg Ile
        355                 360                 365
```

-continued

```
Trp Gly Asp Ala Leu Phe Asp Ile Val Asp Lys Asp Gln Asn Gly Ala
    370                 375                 380

Ile Thr Leu Asp Glu Trp Lys Ala Tyr Thr Lys Ala Ala Gly Ile Ile
385                 390                 395                 400

Gln Ser Ser Glu Asp Cys Glu Glu Thr Phe Arg Val Cys Asp Ile Asp
                405                 410                 415

Glu Ser Gly Gln Leu Asp Val Asp Glu Met Thr Arg Gln His Leu Gly
                420                 425                 430

Phe Trp Tyr Thr Met Asp Pro Ala Cys Glu Lys Leu Tyr Gly Gly Ala
            435                 440                 445

Val Pro
    450

<210> SEQ ID NO 4
<211> LENGTH: 468
<212> TYPE: PRT
<213> ORGANISM: Aequorea victoria

<400> SEQUENCE: 4

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Ser Gly
225                 230                 235                 240

Gly Ser Gly Ser Gly Gly Gln Ser Gly Gly Ser Gly Gly Gln
                245                 250                 255

Ser Gly Gly Ser Gly Ser Gly Gly Gln Ser Gly Gly Ser Gly Ser Gly
            260                 265                 270

Gly Gln Ser Gly Leu Arg Ser Val Lys Leu Thr Ser Asp Phe Asp Asn
```

-continued

```
                275                 280                 285
Pro Arg Trp Ile Gly Arg His Lys His Met Phe Asn Phe Leu Asp Val
    290                 295                 300
Asn His Asn Gly Lys Ile Ser Leu Asp Glu Met Val Tyr Lys Ala Ser
305                 310                 315                 320
Asp Ile Val Ile Asn Asn Leu Gly Ala Thr Pro Glu Gln Ala Lys Arg
                325                 330                 335
His Lys Asp Ala Val Glu Ala Phe Phe Gly Ala Gly Met Lys Tyr
            340                 345                 350
Gly Val Glu Thr Asp Trp Pro Ala Tyr Ile Glu Gly Trp Lys Lys Leu
            355                 360                 365
Ala Thr Asp Glu Leu Glu Lys Tyr Ala Lys Asn Glu Pro Thr Leu Ile
    370                 375                 380
Arg Ile Trp Gly Asp Ala Leu Phe Asp Ile Val Asp Lys Asp Gln Asn
385                 390                 395                 400
Gly Ala Ile Thr Leu Asp Glu Trp Lys Ala Tyr Thr Lys Ala Ala Gly
                405                 410                 415
Ile Ile Gln Ser Ser Glu Asp Cys Glu Glu Thr Phe Arg Val Cys Asp
            420                 425                 430
Ile Asp Glu Ser Gly Gln Leu Asp Val Asp Glu Met Thr Arg Gln His
            435                 440                 445
Leu Gly Phe Trp Tyr Thr Met Asp Pro Ala Cys Glu Lys Leu Tyr Gly
    450                 455                 460
Gly Ala Val Pro
465

<210> SEQ ID NO 5
<211> LENGTH: 477
<212> TYPE: PRT
<213> ORGANISM: Aequorea victoria

<400> SEQUENCE: 5

Met Ser Lys Gly Glu Glu Leu Phe Thr Gly Val Val Pro Ile Leu Val
1               5                   10                  15
Glu Leu Asp Gly Asp Val Asn Gly His Lys Phe Ser Val Ser Gly Glu
            20                  25                  30
Gly Glu Gly Asp Ala Thr Tyr Gly Lys Leu Thr Leu Lys Phe Ile Cys
        35                  40                  45
Thr Thr Gly Lys Leu Pro Val Pro Trp Pro Thr Leu Val Thr Thr Leu
    50                  55                  60
Thr Tyr Gly Val Gln Cys Phe Ser Arg Tyr Pro Asp His Met Lys Gln
65                  70                  75                  80
His Asp Phe Phe Lys Ser Ala Met Pro Glu Gly Tyr Val Gln Glu Arg
                85                  90                  95
Thr Ile Phe Phe Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
        115                 120                 125
Asp Phe Lys Glu Asp Gly Asn Ile Leu Gly His Lys Leu Glu Tyr Asn
    130                 135                 140
Tyr Asn Ser His Asn Val Tyr Ile Met Ala Asp Lys Gln Lys Asn Gly
145                 150                 155                 160
Ile Lys Ala Asn Phe Lys Ile Arg His Asn Ile Glu Asp Gly Ser Val
                165                 170                 175
```

```
Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys Ser Gly
225                 230                 235                 240

Gly Ser Gly Ser Gly Gly Gln Ser Gly Gly Ser Gly Gly Gln
                245                 250                 255

Ser Gly Gly Ser Gly Ser Gly Gly Gln Ser Gly Gly Ser Gly Ser Gly
                260                 265                 270

Gly Gln Ser Gly Gly Ser Gly Ser Gly Gly Gln Ser Gly Leu Arg Ser
                275                 280                 285

Val Lys Leu Thr Ser Asp Phe Asp Asn Pro Arg Trp Ile Gly Arg His
        290                 295                 300

Lys His Met Phe Asn Phe Leu Asp Val Asn His Asn Gly Lys Ile Ser
305                 310                 315                 320

Leu Asp Glu Met Val Tyr Lys Ala Ser Asp Ile Val Ile Asn Asn Leu
                325                 330                 335

Gly Ala Thr Pro Glu Gln Ala Lys Arg His Lys Asp Ala Val Glu Ala
                340                 345                 350

Phe Phe Gly Gly Ala Gly Met Lys Tyr Gly Val Glu Thr Asp Trp Pro
            355                 360                 365

Ala Tyr Ile Glu Gly Trp Lys Lys Leu Ala Thr Asp Glu Leu Glu Lys
        370                 375                 380

Tyr Ala Lys Asn Glu Pro Thr Leu Ile Arg Ile Trp Gly Asp Ala Leu
385                 390                 395                 400

Phe Asp Ile Val Asp Lys Asp Gln Asn Gly Ala Ile Thr Leu Asp Glu
                405                 410                 415

Trp Lys Ala Tyr Thr Lys Ala Ala Gly Ile Ile Gln Ser Ser Glu Asp
                420                 425                 430

Cys Glu Glu Thr Phe Arg Val Cys Asp Ile Asp Glu Ser Gly Gln Leu
            435                 440                 445

Asp Val Asp Glu Met Thr Arg Gln His Leu Gly Phe Trp Tyr Thr Met
        450                 455                 460

Asp Pro Ala Cys Glu Lys Leu Tyr Gly Gly Ala Val Pro
465                 470                 475

<210> SEQ ID NO 6
<211> LENGTH: 906
<212> TYPE: PRT
<213> ORGANISM: Aequorea victoria

<400> SEQUENCE: 6

Met Val Ser Ala Ser Arg Pro Glu Ala Leu Ala Ala Pro Val Thr Thr
1               5                   10                  15

Val Ala Thr Leu Val Pro His Asn Ala Thr Glu Pro Ala Ser Pro Gly
            20                  25                  30

Glu Gly Lys Glu Asp Ala Phe Ser Lys Leu Lys Gln Lys Phe Met Asn
        35                  40                  45

Glu Leu His Lys Ile Pro Leu Pro Pro Trp Ala Leu Ile Ala Ile Ala
    50                  55                  60

Ile Val Ala Val Leu Leu Val Val Thr Cys Cys Phe Cys Val Cys Lys
65                  70                  75                  80
```

```
Lys Cys Leu Phe Lys Lys Asn Lys Lys Gly Lys Glu Lys Gly
            85                  90                  95

Gly Lys Asn Ala Ile Asn Met Lys Asp Val Lys Asp Leu Gly Lys Thr
                100                 105                 110

Met Lys Asp Gln Ala Leu Lys Asp Asp Ala Glu Thr Gly Leu Thr
        115                 120                 125

Asp Gly Glu Glu Lys Glu Pro Lys Glu Glu Lys Leu Gly Lys
    130                 135                 140

Leu Gln Tyr Ser Leu Asp Tyr Asp Phe Gln Asn Asn Gln Leu Leu Val
145                 150                 155                 160

Gly Ile Ile Gln Ala Ala Glu Leu Pro Ala Leu Asp Met Gly Gly Thr
                165                 170                 175

Ser Asp Pro Tyr Val Lys Val Phe Leu Leu Pro Asp Lys Lys Lys
            180                 185                 190

Phe Glu Thr Lys Val His Arg Lys Thr Leu Asn Pro Val Phe Asn Glu
        195                 200                 205

Gln Phe Thr Phe Lys Val Pro Tyr Ser Glu Leu Gly Gly Lys Thr Leu
    210                 215                 220

Val Met Ala Val Tyr Asp Phe Asp Arg Phe Ser Lys His Asp Ile Ile
225                 230                 235                 240

Gly Glu Phe Lys Val Pro Met Asn Thr Val Asp Phe Gly His Val Thr
                245                 250                 255

Glu Glu Trp Arg Asp Leu Gln Ser Ala Glu Lys Glu Gln Glu Lys
            260                 265                 270

Leu Gly Asp Ile Cys Phe Ser Leu Arg Tyr Val Pro Thr Ala Gly Lys
        275                 280                 285

Leu Thr Val Val Ile Leu Glu Ala Lys Asn Leu Lys Lys Met Asp Val
    290                 295                 300

Gly Gly Leu Ser Asp Pro Tyr Val Lys Ile His Leu Met Gln Asn Gly
305                 310                 315                 320

Lys Arg Leu Lys Lys Lys Lys Thr Thr Ile Lys Lys Asn Thr Leu Asn
                325                 330                 335

Pro Tyr Tyr Asn Glu Ser Phe Ser Phe Glu Val Pro Phe Glu Gln Ile
            340                 345                 350

Gln Lys Val Gln Val Val Thr Val Leu Asp Tyr Asp Lys Ile Gly
        355                 360                 365

Lys Asn Asp Ala Ile Gly Lys Val Phe Val Gly Tyr Asn Ser Thr Gly
    370                 375                 380

Ala Glu Leu Arg His Trp Ser Asp Met Leu Ala Asn Pro Arg Arg Pro
385                 390                 395                 400

Ile Ala Gln Trp His Thr Leu Gln Val Glu Glu Val Asp Ala Met
                405                 410                 415

Leu Ala Val Lys Arg Ser Gly Asn Ser Gly Arg Ala Thr Met Ser Lys
            420                 425                 430

Gly Glu Glu Leu Phe Thr Gly Val Val Pro Ile Leu Val Glu Leu Asp
        435                 440                 445

Gly Asp Val Asn Gly His Lys Phe Ser Val Ser Gly Glu Gly Glu Gly
    450                 455                 460

Asp Ala Thr Tyr Gly Lys Leu Thr Leu Lys Phe Ile Cys Thr Thr Gly
465                 470                 475                 480

Lys Leu Pro Val Pro Trp Pro Thr Leu Val Thr Thr Leu Thr Tyr Gly
                485                 490                 495
```

-continued

```
Val Gln Cys Phe Ser Arg Tyr Pro Asp His Met Lys Gln His Asp Phe
            500                 505                 510

Phe Lys Ser Ala Met Pro Glu Gly Tyr Val Gln Glu Arg Thr Ile Phe
            515                 520                 525

Phe Lys Asp Asp Gly Asn Tyr Lys Thr Arg Ala Glu Val Lys Phe Glu
            530                 535                 540

Gly Asp Thr Leu Val Asn Arg Ile Glu Leu Lys Gly Ile Asp Phe Lys
545                 550                 555                 560

Glu Asp Gly Asn Ile Leu Gly His Lys Leu Glu Tyr Asn Tyr Asn Ser
                565                 570                 575

His Asn Val Tyr Ile Met Ala Asp Lys Gln Lys Asn Gly Ile Lys Ala
            580                 585                 590

Asn Phe Lys Ile Arg His Asn Ile Glu Asp Gly Ser Val Gln Leu Ala
            595                 600                 605

Asp His Tyr Gln Gln Asn Thr Pro Ile Gly Asp Gly Pro Val Leu Leu
            610                 615                 620

Pro Asp Asn His Tyr Leu Ser Thr Gln Ser Ala Leu Ser Lys Asp Pro
625                 630                 635                 640

Asn Glu Lys Arg Asp His Met Val Leu Leu Glu Phe Val Thr Ala Ala
                645                 650                 655

Gly Ile Thr His Gly Met Asp Glu Leu Tyr Lys Ser Gly Gly Ser Gly
            660                 665                 670

Ser Gly Gly Gln Ser Gly Gly Ser Gly Gly Gln Ser Gly Gly
            675                 680                 685

Ser Gly Ser Gly Gly Gln Ser Gly Gly Ser Gly Ser Gly Gly Gln Ser
            690                 695                 700

Gly Gly Ser Gly Ser Gly Gly Gln Ser Gly Leu Arg Ser Val Lys Leu
705                 710                 715                 720

Thr Ser Asp Phe Asp Asn Pro Arg Trp Ile Gly Arg His Lys His Met
                725                 730                 735

Phe Asn Phe Leu Asp Val Asn His Asn Gly Lys Ile Ser Leu Asp Glu
            740                 745                 750

Met Val Tyr Lys Ala Ser Asp Ile Val Ile Asn Asn Leu Gly Ala Thr
            755                 760                 765

Pro Glu Gln Ala Lys Arg His Lys Asp Ala Val Glu Ala Phe Phe Gly
            770                 775                 780

Gly Ala Gly Met Lys Tyr Gly Val Glu Thr Asp Trp Pro Ala Tyr Ile
785                 790                 795                 800

Glu Gly Trp Lys Lys Leu Ala Thr Asp Glu Leu Glu Lys Tyr Ala Lys
                805                 810                 815

Asn Glu Pro Thr Leu Ile Arg Ile Trp Gly Asp Ala Leu Phe Asp Ile
            820                 825                 830

Val Asp Lys Asp Gln Asn Gly Ala Ile Thr Leu Asp Glu Trp Lys Ala
            835                 840                 845

Tyr Thr Lys Ala Ala Gly Ile Ile Gln Ser Ser Glu Asp Cys Glu Glu
            850                 855                 860

Thr Phe Arg Val Cys Asp Ile Asp Glu Ser Gly Gln Leu Asp Val Asp
865                 870                 875                 880

Glu Met Thr Arg Gln His Leu Gly Phe Trp Tyr Thr Met Asp Pro Ala
                885                 890                 895

Cys Glu Lys Leu Tyr Gly Gly Ala Val Pro
            900                 905
```

<210> SEQ ID NO 7
<211> LENGTH: 3973
<212> TYPE: DNA
<213> ORGANISM: Aequorea victoria

<400> SEQUENCE: 7

| | | | | | |
|---|---|---|---|---|---|
| atgagcaagg | gcgaggagct | gttcaccggg | gtggtgccca | tcctggtcga | gctggacggc | 60 |
| gacgtaaacg | gccacaagtt | cagcgtgtcc | ggcgagggcg | agggcgatgc | cacctacggc | 120 |
| aagctgaccc | tgaagttcat | ctgcaccacc | ggcaagctgc | ccgtgccctg | gcccaccctc | 180 |
| gtgaccaccc | tgacctacgg | cgtgcagtgc | ttcagccgct | accccgacca | catgaagcag | 240 |
| cacgacttct | tcaagtccgc | catgcccgaa | ggctacgtcc | aggagcgcac | catcttcttc | 300 |
| aaggacgacg | gcaactacaa | gacccgcgcc | gaggtgaagt | tcgagggcga | caccctggtg | 360 |
| aaccgcatcg | agctgaaggg | catcgacttc | aaggaggacg | gcaacatcct | ggggcacaag | 420 |
| ctggagtaca | actacaacag | ccacaacgtc | tatatcatgg | ccgacaagca | gaagaacggc | 480 |
| atcaaggcca | acttcaagat | ccgccacaac | atcgaggacg | gcagcgtgca | gctcgccgac | 540 |
| cactaccagc | agaacacccc | catcggcgac | ggccccgtgc | tgctgcccga | caaccactac | 600 |
| ctgagcaccc | agtccgccct | gagcaaagac | cccaacgaga | agcgcgatca | catggtcctg | 660 |
| ctggagttcg | tgaccgccgc | cgggatcact | cacggcatgg | acgagctgta | caagtccgga | 720 |
| ctcagatctg | tcaaacttac | atcagacttc | gacaacccaa | gatggattgg | acgacacaag | 780 |
| catatgttca | atttccttga | tgtcaaccac | aatggaaaaa | tctctcttga | cgagatggtc | 840 |
| tacaaggcat | ctgatattgt | catcaataac | cttggagcaa | cacctgagca | agccaaacga | 900 |
| cacaaagatg | ctgtggaagc | cttcttcgga | ggagctggaa | tgaaatatgg | tgtggaaact | 960 |
| gattggcctg | catatattga | aggatggaaa | aaattggcta | ctgatgaatt | ggagaaatac | 1020 |
| gccaaaaacg | aaccaaccct | catccgcata | tggggtgatg | ctttgtttga | tatcgttgac | 1080 |
| aaagatcaaa | atggagctat | tacactggat | gaatggaaag | catacaccaa | agctgctggt | 1140 |
| atcatccaat | catcagaaga | ttgcgaggaa | acattcagag | tgtgcgatat | tgatgaaagt | 1200 |
| ggacaactcg | atgttgatga | gatgacaaga | cagcatctgg | gattttggta | caccatggat | 1260 |
| cctgcttgcg | aaaagctcta | cggtggagct | gtccccgaat | gagcaagggc | gaggagctgt | 1320 |
| tcaccggggt | ggtgcccatc | ctggtcgagc | tggacggcga | cgtaaacggc | cacaagttca | 1380 |
| gcgtgtccgg | cgagggcgag | ggcgatgcca | cctacggcaa | gctgaccctg | aagttcatct | 1440 |
| gcaccaccgg | caagctgccc | gtgccctggc | ccacccctcgt | gaccaccctg | acctacggcg | 1500 |
| tgcagtgctt | cagccgctac | cccgaccaca | tgaagcagca | cgacttcttc | aagtccgcca | 1560 |
| tgcccgaagg | ctacgtccag | gagcgcacca | tcttcttcaa | ggacgacggc | aactacaaga | 1620 |
| cccgcgccga | ggtgaagttc | gagggcgaca | ccctggtgaa | ccgcatcgag | ctgaagggca | 1680 |
| tcgacttcaa | ggaggacggc | aacatcctgg | ggcacaagct | ggagtacaac | tacaacagcc | 1740 |
| acaacgtcta | tatcatggcc | gacaagcaga | agaacggcat | caaggccaac | ttcaagatcc | 1800 |
| gccacaacat | cgaggacggc | agcgtgcagc | tcgccgacca | ctaccagcag | aacaccccca | 1860 |
| tcggcgacgg | ccccgtgctg | ctgcccgaca | accactacct | gagcacccag | tccgccctga | 1920 |
| gcaaagaccc | caacgagaag | cgcgatcaca | tggtcctgct | ggagttcgtg | accgccgccg | 1980 |
| ggatcactca | cggcatggac | gagctgtaca | agtccgcgcg | gagcggatcc | ggcggccagt | 2040 |
| ccggcctcag | atctgtcaaa | cttacatcag | acttcgacaa | cccaagatgg | attggacgac | 2100 |
| acaagcatat | gttcaatttc | cttgatgtca | accacaatgg | aaaaatctct | cttgacgaga | 2160 |

| | |
|---|---|
| tggtctacaa ggcatctgat attgtcatca ataaccttgg agcaacacct gagcaagcca | 2220 |
| aacgacacaa agatgctgtg aagccttct tcggaggagc tggaatgaaa tatggtgtgg | 2280 |
| aaactgattg gcctgcatat attgaaggat ggaaaaaatt ggctactgat gaattggaga | 2340 |
| aatacgccaa aaacgaacca accctcatcc gcatatgggg tgatgctttg tttgatatcg | 2400 |
| ttgacaaaga tcaaaatgga gctattacac tggatgaatg gaaagcatac accaaagctg | 2460 |
| ctggtatcat ccaatcatca gaagattgcg aggaaacatt cagagtgtgc gatattgatg | 2520 |
| aaagtggaca actcgatgtt gatgagatga agacagca tctgggattt tggtacacca | 2580 |
| tggatcctgc ttgcgaaaag ctctacggtg agctgtccc cgaatgagca agggcgagga | 2640 |
| gctgttcacc ggggtggtgc ccatcctggt cgagctggac ggcgacgtaa acggccacaa | 2700 |
| gttcagcgtg tccggcgagg gcgagggcga tgccacctac ggcaagctga ccctgaagtt | 2760 |
| catctgcacc accggcaagc tgcccgtgcc ctggcccacc ctcgtgacca ccctgaccta | 2820 |
| cggcgtgcag tgcttcagcc gctaccccga ccacatgaag cagcacgact tcttcaagtc | 2880 |
| cgccatgccc gaaggctacg tccaggagcg caccatcttc ttcaaggacg acggcaacta | 2940 |
| caagacccgc gccgaggtga agttcgaggg cgacaccctg gtgaaccgca tcgagctgaa | 3000 |
| gggcatcgac ttcaaggagg acggcaacat cctggggcac aagctggagt acaactacaa | 3060 |
| cagccacaac gtctatatca tggccgacaa gcagaagaac ggcatcaagg ccaacttcaa | 3120 |
| gatccgccac aacatcgagg acggcagcgt gcagctcgcc gaccactacc agcagaacac | 3180 |
| ccccatcggc gacggccccg tgctgctgcc cgacaaccac tacctgagca cccagtccgc | 3240 |
| cctgagcaaa gaccccaacg agaagcgcga tcacatggtc ctgctggagt tcgtgaccgc | 3300 |
| cgccgggatc actcacggca tggacgagct gtacaagtcc ggcgggagcg gatccggcgg | 3360 |
| ccagtccggc gggagcggat ccggcggcca gtccggcctc agatctgtca aacttacatc | 3420 |
| agacttcgac aacccaagat ggattggacg acacaagcat atgttcaatt tccttgatgt | 3480 |
| caaccacaat ggaaaaatct ctcttgacga gatggtctac aaggcatctg atattgtcat | 3540 |
| caataacctt ggagcaacac ctgagcaagc caaacgacac aaagatgctg tggaagcctt | 3600 |
| cttcggagga gctggaatga aatatggtgt ggaaactgat tggcctgcat atattgaagg | 3660 |
| atggaaaaaa ttggctactg atgaattgga gaaatacgcc aaaaacgaac caaccctcat | 3720 |
| ccgcatatgg ggtgatgctt tgtttgatat cgttgacaaa gatcaaaatg gagctattac | 3780 |
| actggatgaa tggaaagcat acaccaaagc tgctggtatc atccaatcat cagaagattg | 3840 |
| cgaggaaaca ttcagagtgt gcgatattga tgaaagtgga caactcgatg ttgatgagat | 3900 |
| gacaagacag catctgggat tttggtacac catggatcct gcttgcgaaa agctctacgg | 3960 |
| tgagctgtc ccc | 3973 |

<210> SEQ ID NO 8
<211> LENGTH: 2673
<212> TYPE: DNA
<213> ORGANISM: Aequorea victoria
<400> SEQUENCE: 8

| | |
|---|---|
| atgagcaagg gcgaggagct gttcaccggg gtggtgccca tcctggtcga gctggacggc | 60 |
| gacgtaaacg gccacaagtt cagcgtgtcc ggcgagggcg agggcgatgc cacctacggc | 120 |
| aagctgaccc tgaagttcat ctgcaccacc ggcaagctgc ccgtgccctg gcccaccctc | 180 |
| gtgaccaccc tgacctacgg cgtgcagtgc ttcagccgct accccgacca catgaagcag | 240 |
| cacgacttct tcaagtccgc catgcccgaa ggctacgtcc aggagcgcac catcttcttc | 300 |

-continued

```
aaggacgacg gcaactacaa gacccgcgcc gaggtgaagt tcgagggcga cccctggtg      360
aaccgcatcg agctgaaggg catcgacttc aaggaggacg gcaacatcct ggggcacaag      420
ctggagtaca actacaacag ccacaacgtc tatatcatgg ccgacaagca gaagaacggc      480
atcaaggcca acttcaagat ccgccacaac atcgaggacg gcagcgtgca gctcgccgac      540
cactaccagc agaacacccc catcggcgac ggccccgtgc tgctgcccga caaccactac      600
ctgagcaccc agtccgccct gagcaaagac cccaacgaga gcgcgatca catggtcctg      660
ctggagttcg tgaccgccgc cgggatcact cacggcatgg acgagctgta caagtccggc      720
gggagcggat ccggcggcca gtccggcctc agatctgtca acttacatc agacttcgac      780
aacccaagat ggattggacg acacaagcat atgttcaatt ccttgatgt caaccacaat      840
ggaaaaatct ctcttgacga gatggtctac aaggcatctg atattgtcat caataacctt      900
ggagcaacac ctgagcaagc caaacgacac aaagatgctg tggaagcctt cttcggagga      960
gctggaatga aatatggtgt ggaaactgat tggcctgcat atattgaagg atggaaaaaa     1020
ttggctactg atgaattgga gaaatacgcc aaaaacgaac caaccctcat ccgcatatgg     1080
ggtgatgctt tgtttgatat cgttgacaaa gatcaaaatg gagctattac actggatgaa     1140
tggaaagcat acaccaaagc tgctggtatc atccaatcat cagaagattg cgaggaaaca     1200
ttcagagtgt gcgatattga tgaaagtgga caactcgatg ttgatgagat gacaagacag     1260
catctgggat tttggtacac catggatcct gcttgcgaaa agctctacgg tggagctgtc     1320
cccatgagca agggcgagga gctgttcacc ggggtggtgc ccatcctggt cgagctggac     1380
ggcgacgtaa acggccacaa gttcagcgtg tccggcgagg gcgagggcga tgccacctac     1440
ggcaagctga ccctgaagtt catctgcacc accggcaagc tgcccgtgcc ctggcccacc     1500
ctcgtgacca cctgaccta cggcgtgcag tgcttcagcc gctaccccga ccacatgaag     1560
cagcacgact tcttcaagtc cgccatgccc gaaggctacg tccaggagcg caccatcttc     1620
ttcaaggacg acggcaacta caagacccgc gccgaggtga agttcgaggg cgacaccctg     1680
gtgaaccgca tcgagctgaa gggcatcgac ttcaaggagg acggcaacat cctggggcac     1740
aagctggagt acaactacaa cagccacaac gtctatatca tggccgacaa gcagaagaac     1800
ggcatcaagg ccaacttcaa gatccgccac aacatcgagg acggcagcgt gcagctcgcc     1860
gaccactacc agcagaacac ccccatcggc gacggccccg tgctgctgcc cgacaaccac     1920
tacctgagca cccagtccgc cctgagcaaa gaccccaacg agaagcgcga tcacatggtc     1980
ctgctggagt tcgtgaccgc cgccgggatc actcacggca tggacgagct gtacaagtcc     2040
ggcgggagcg gatccggcgg ccagtccggc gggagcggat ccggcggcca gtccggcctc     2100
agatctgtca acttacatc agacttcgac aacccaagat ggattggacg acacaagcat     2160
atgttcaatt ccttgatgt caaccacaat ggaaaaatct ctcttgacga gatggtctac     2220
aaggcatctg atattgtcat caataacctt ggagcaacac ctgagcaagc caaacgacac     2280
aaagatgctg tggaagcctt cttcggagga gctggaatga aatatggtgt ggaaactgat     2340
tggcctgcat atattgaagg atggaaaaaa ttggctactg atgaattgga gaaatacgcc     2400
aaaaacgaac caaccctcat ccgcatatgg ggtgatgctt tgtttgatat cgttgacaaa     2460
gatcaaaatg gagctattac actggatgaa tggaaagcat acaccaaagc tgctggtatc     2520
atccaatcat cagaagattg cgaggaaaca ttcagagtgt gcgatattga tgaaagtgga     2580
caactcgatg ttgatgagat gacaagacag catctgggat tttggtacac catggatcct     2640
```
gcttgcgaaa agctctacgg tggagctgtc ccc                                    2673

<210> SEQ ID NO 9
<211> LENGTH: 1350
<212> TYPE: DNA
<213> ORGANISM: Aequorea victoria

<400> SEQUENCE: 9
atgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg cccaccctc    180
gtgaccaccc tgacctacgg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacaacag ccacaacgtc tatatcatgg ccgacaagca gaagaacggc   480
atcaaggcca acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca catggtcctg   660
ctggagttcg tgaccgccgc cgggatcact cacggcatgg acgagctgta caagtccggc   720
gggagcggat ccggcggcca gtccggcggg agcggatccg gcggccagtc cggcctcaga   780
tctgtcaaac ttacatcaga cttcgacaac ccaagatgga ttggacgaca caagcatatg   840
ttcaatttcc ttgatgtcaa ccacaatgga aaaatctctc ttgacgagat ggtctacaag   900
gcatctgata ttgtcatcaa taaccttgga gcaacacctg agcaagccaa acgacacaaa   960
gatgctgtgg aagccttctt cggaggagct ggaatgaaat atggtgtgga aactgattgg  1020
cctgcatata ttgaaggatg gaaaaaattg gctactgatg aattggagaa atacgccaaa  1080
aacgaaccaa ccctcatccg catatggggt gatgctttgt ttgatatcgt tgacaaagat  1140
caaaatggag ctattacact ggatgaatgg aaagcataca ccaaagctgc tggtatcatc  1200
caatcatcag aagattgcga ggaaacattc agagtgtgcg atattgatga agtggacaa   1260
ctcgatgttg atgagatgac aagacagcat ctgggatttt ggtacaccat ggatcctgct  1320
tgcgaaaagc tctacggtgg agctgtcccc                                   1350

<210> SEQ ID NO 10
<211> LENGTH: 1404
<212> TYPE: DNA
<213> ORGANISM: Aequorea victoria

<400> SEQUENCE: 10
atgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg cccaccctc    180
gtgaccaccc tgacctacgg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacaacag ccacaacgtc tatatcatgg ccgacaagca gaagaacggc   480

```
atcaaggcca acttcaagat ccgccacaac atcgaggacg gcagcgtgca gctcgccgac      540
cactaccagc agaacacccc catcggcgac ggccccgtgc tgctgcccga caaccactac      600
ctgagcaccc agtccgccct gagcaaagac cccaacgaga agcgcgatca catggtcctg      660
ctggagttcg tgaccgccgc cgggatcact cacggcatgg acgagctgta caagtccggc      720
gggagcggat ccggcggcca gtccggcggg agcggatccg gcggccagtc cggcgggagc      780
ggatccggcg gccagtccgg cgggagcgga tccggcggcc agtccggcct cagatctgtc      840
aaacttacat cagacttcga caacccaaga tggattggac gacacaagca tatgttcaat      900
ttccttgatg tcaaccacaa tggaaaaatc tctcttgacg agatggtcta caaggcatct      960
gatattgtca tcaataacct tggagcaaca cctgagcaag ccaaacgaca caaagatgct     1020
gtggaagcct tcttcggagg agctggaatg aaatatggtg tggaaactga ttggcctgca     1080
tatattgaag gatggaaaaa attggctact gatgaattgg agaaatacgc caaaaacgaa     1140
ccaaccctca tccgcatatg gggtgatgct tgtttgata tcgttgacaa agatcaaaat     1200
ggagctatta cactgatga atggaaagca tacaccaaag ctgctggtat catccaatca     1260
tcagaagatt gcgaggaaac attcagagtg tgcgatattg atgaaagtgg acaactcgat     1320
gttgatgaga tgacaagaca gcatctggga ttttggtaca ccatggatcc tgcttgcgaa     1380
aagctctacg gtggagctgt cccc                                            1404
```

<210> SEQ ID NO 11
<211> LENGTH: 1431
<212> TYPE: DNA
<213> ORGANISM: Aequorea victoria

<400> SEQUENCE: 11

```
atgagcaagg gcgaggagct gttcaccggg gtggtgccca tcctggtcga gctggacggc       60
gacgtaaacg gccacaagtt cagcgtgtcc ggcgagggcg agggcgatgc cacctacggc      120
aagctgaccc tgaagttcat ctgcaccacc ggcaagctgc ccgtgccctg gcccaccctc      180
gtgaccaccc tgacctacgg cgtgcagtgc ttcagccgct accccgacca catgaagcag      240
cacgacttct tcaagtccgc catgcccgaa ggctacgtcc aggagcgcac catcttcttc      300
aaggacgacg gcaactacaa gacccgcgcc gaggtgaagt tcgagggcga caccctggtg      360
aaccgcatcg agctgaaggg catcgacttc aaggaggacg gcaacatcct ggggcacaag      420
ctggagtaca actacaacag ccacaacgtc tatatcatgg ccgacaagca gaagaacggc      480
atcaaggcca acttcaagat ccgccacaac atcgaggacg gcagcgtgca gctcgccgac      540
cactaccagc agaacacccc catcggcgac ggccccgtgc tgctgcccga caaccactac      600
ctgagcaccc agtccgccct gagcaaagac cccaacgaga agcgcgatca catggtcctg      660
ctggagttcg tgaccgccgc cgggatcact cacggcatgg acgagctgta caagtccggc      720
gggagcggat ccggcggcca gtccggcggg agcggatccg gcggccagtc cggcgggagc      780
ggatccggcg gccagtccgg cgggagcgga tccggcggcc agtccggcgg gagcggatcc      840
ggcggccagt ccggcctcag atctgtcaaa cttacatcag acttcgacaa cccaagatgg      900
attggacgac acaagcatat gttcaatttc cttgatgtca accacaatgg aaaaatctct     960
cttgacgaga tggtctacaa ggcatctgat attgtcatca ataaccttgg agcaacacct     1020
gagcaagcca aacgacacaa agatgctgtg gaagccttct tcggaggagc tggaatgaaa     1080
tatggtgtgg aaactgattg gcctgcatat attgaaggat ggaaaaaatt ggctactgat     1140
```

```
gaattggaga aatacgccaa aaacgaacca accctcatcc gcatatgggg tgatgctttg   1200
tttgatatcg ttgacaaaga tcaaaatgga gctattacac tggatgaatg gaaagcatac   1260
accaaagctg ctggtatcat ccaatcatca gaagattgcg aggaaacatt cagagtgtgc   1320
gatattgatg aaagtggaca actcgatgtt gatgagatga caagacagca tctgggattt   1380
tggtacacca tggatcctgc ttgcgaaaag ctctacggtg agctgtccc c              1431
```

<210> SEQ ID NO 12
<211> LENGTH: 2718
<212> TYPE: DNA
<213> ORGANISM: Aequorea victoria

<400> SEQUENCE: 12

```
atggtgagtg ccagtcgtcc tgaggccctg gctgcccctg tcaccactgt tgcgacccct     60
gtcccacaca acgccactga gccagccagt cctggggaag ggaaggaaga tgcctttttcc   120 aagctgaagc agaagtttat gaatgaactg cataaaatcc cattgccacc gtgggcctta    180
attgccatag ccatagttgc ggtccttcta gtcgtgacct gctgcttctg tgtctgtaag    240
aaatgtttgt tcaaaagaa aaacaagaag aagggaaagg aaaagggagg aagaacgcc      300 attaacatga aagacgtgaa agacttaggg aagaccatga aggatcaggc ccttaaggat    360
gacgatgctg aaactggact gactgatgga gaagaaaagg aggagcccaa ggaagaggag    420
aaactgggaa agcttcaata ttcactggac tatgacttcc agaataacca gctgctggtg    480
ggaatcatcc aggctgctga actgcccgcc ctggacatgg gaggcacatc tgatccatac    540
gtcaaagtct tcctgctgcc cgacaaaaag aagaagtttg agacaaaagt ccaccggaaa    600
accctcaatc agtcttcaa tgaacagttt actttcaagg tgccatactc ggaattaggt     660
ggcaagacac tggtgatggc tgtgtatgat tttgaccgct ctccaagca cgacatcatt     720 ggagagttca agttcctat gaacaccgtg gattttggcc acgtcaccga ggagtggcgc     780
gatctccaga gtgctgagaa agaagagcaa gagaaactgg gtgacatctg cttctccctc    840
cgctacgtcc ctactgccgg caagctgact gttgtcattc tggaagccaa gaacctgaag    900
aagatggatg tgggtggctt atctgatccc tatgtaaaga ttcacctgat gcagaacggc    960
aagagactga agaagaaaaa gacaacgatt aagaagaaca cacttaaccc ctactacaat   1020
gagtccttca gctttgaagt tccgttcgag caaatccaga aagtgcaagt ggtggtaact   1080
gttttggact atgacaagat tggcaagaac gacgccatcg gcaaagtctt tgtgggctac   1140
aacagcaccg gcgcagagct gcgacactgg tcagacatgc tggccaaccc ccggcgaccc   1200
atcgcccagt ggcacactct gcaggtagag gaggaggttg atgccatgct ggctgtcaag   1260
agatccggga attccgggcg ggccaccatg agcaagggcg aggagctgtt caccggggtg   1320
gtgcccatcc tggtcgagct ggacggcgac gtaaacggcc acaagttcag cgtgtccggc   1380
gagggcgagg gcgatgccac ctacggcaag ctgaccctga gttcatctg caccaccggc   1440 aagctgcccg tgccctggcc caccctcgtg accaccctga cctacggcgt gcagtgcttc   1500
agccgctacc ccgaccacat gaagcagcac gacttcttca gtccgccat gcccgaaggc    1560 tacgtccagg agcgcaccat cttcttcaag gacgacggca actacaagac ccgcgccgag   1620
gtgaagttcg agggcgacac cctggtgaac cgcatcgagc tgaagggcat cgacttcaag   1680
gaggacggca acatcctggg gcacaagctg gagtacaact acaacagcca caacgtctat   1740
atcatggccg acaagcagaa gaacggcatc aaggccaact tcaagatccg ccacaacatc   1800
gaggacggca gcgtgcagct cgccgaccac taccagcaga cacccccat cggcgacggc    1860
```

```
cccgtgctgc tgcccgacaa ccactacctg agcacccagt ccgccctgag caaagacccc    1920
aacgagaagc gcgatcacat ggtcctgctg gagttcgtga ccgccgccgg gatcactcac    1980
ggcatggacg agctgtacaa gtccggcggg agcggatccg gcggccagtc cggcgggagc    2040
ggatccggcg gccagtccgg cgggagcgga tccgcggcc agtccggcgg gagcggatcc    2100
ggcggccagt ccggcgggag cggatccggc ggccagtccg gcctcagatc tgtcaaactt    2160
acatcagact tcgacaaccc aagatggatt ggacgacaca agcatatgtt caatttcctt    2220
gatgtcaacc acaatggaaa aatctctctt gacgagatgg tctacaaggc atctgatatt    2280
gtcatcaata accttggagc aacacctgag caagccaaac gacacaaaga tgctgtggaa    2340
gccttcttcg gaggagctgg aatgaaatat ggtgtggaaa ctgattggcc tgcatatatt    2400
gaaggatgga aaaaattggc tactgatgaa ttggagaaat acgccaaaaa cgaaccaacc    2460
ctcatccgca tatggggtga tgctttgttt gatatcgttg acaaagatca aaatggagct    2520
attacactgg atgaatggaa agcatacacc aaagctgctg gtatcatcca atcatcagaa    2580
gattgcgagg aaacattcag agtgtgcgat attgatgaaa gtggacaact cgatgttgat    2640
gagatgacaa gacagcatct gggattttgg tacaccatgg atcctgcttg cgaaaagctc    2700
tacggtggag ctgtccccc                                                2718
```

```
<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tccggcctca gatct                                                      15

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tccggcggga gcggatccgg cggccagtcc ggcctcagat ct                        42

<210> SEQ ID NO 15
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tccggcggga gcggatccgg cggccagtcc ggcgggagcg gatccggcgg ccagtccggc    60
ctcagatct                                                             69

<210> SEQ ID NO 16
<211> LENGTH: 123
<212> TYPE: DNA
<213> ORGANISM: Artificial Sequence
<220> FEATURE:
<223> OTHER INFORMATION: Description of Artificial Sequence: Synthetic
```

```
                                    polynucleotide

<400> SEQUENCE: 16
tccggcggga gcggatccgg cggccagtcc ggcgggagcg gatccggcgg ccagtccggc    60
gggagcggat ccggcggcca gtccggcggg agcggatccg gcggccagtc cggcctcaga   120
tct                                                                 123

<210> SEQ ID NO 17
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
tccggcggga gcggatccgg cggccagtcc ggcgggagcg gatccggcgg ccagtccggc    60
gggagcggat ccggcggcca gtccggcggg agcggatccg gcggccagtc cggcgggagc   120
ggatccggcg gccagtccgg cctcagatct                                    150

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Gly Leu Arg Ser
1               5

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Gly Gly Ser Gly Ser Gly Gly Gln Ser Gly Leu Arg Ser
1               5                   10

<210> SEQ ID NO 20
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Gly Gly Ser Gly Ser Gly Gly Gln Ser Gly Gly Ser Gly Ser Gly
1               5                   10                  15

Gly Gln Ser Gly Leu Arg Ser
            20

<210> SEQ ID NO 21
<211> LENGTH: 41
<212> TYPE: PRT
<213> ORGANISM: Artificial Sequence
<220> FEATURE:
<223> OTHER INFORMATION: Description of Artificial Sequence: Synthetic
```

```
                                    polypeptide

<400> SEQUENCE: 21

Ser Gly Gly Ser Gly Ser Gly Gly Gln Ser Gly Gly Ser Gly Ser Gly
1               5                   10                  15

Gly Gln Ser Gly Gly Ser Gly Ser Gly Gly Gln Ser Gly Gly Ser Gly
            20                  25                  30

Ser Gly Gly Gln Ser Gly Leu Arg Ser
        35                  40

<210> SEQ ID NO 22
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser Gly Gly Ser Gly Ser Gly Gly Gln Ser Gly Gly Ser Gly Ser Gly
1               5                   10                  15

Gly Gln Ser Gly Gly Ser Gly Ser Gly Gly Gln Ser Gly Gly Ser Gly
            20                  25                  30

Ser Gly Gly Gln Ser Gly Gly Ser Gly Ser Gly Gly Gln Ser Gly Leu
        35                  40                  45

Arg Ser
    50

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ccggcgggag cggatccggc ggccagt                                        27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ccggactggc cgccggatcc gctcccg                                        27

<210> SEQ ID NO 25
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 1 to 5
      'Gly-Gly-Ser-Gly-Ser-Gly-Gly-Gln-Ser' repeating units
<220> FEATURE:
<223> OTHER INFORMATION: see specification as filed for detailed
      description of substitutions and preferred embodiments

<400> SEQUENCE: 25
```

```
Gly Gly Ser Gly Ser Gly Gly Gln Ser Gly Gly Ser Gly Ser Gly Gly
1               5                   10                  15

Gln Ser Gly Gly Ser Gly Ser Gly Gly Gln Ser Gly Gly Ser Gly Ser
            20                  25                  30

Gly Gly Gln Ser Gly Gly Ser Gly Ser Gly Gly Gln Ser
        35                  40                  45
```

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Ser Gly Leu Arg Ser
1               5
```

<210> SEQ ID NO 27
<211> LENGTH: 27
<212> TYPE: DNA
<213> ORGANISM: Unknown
<220> FEATURE:
<223> OTHER INFORMATION: Description of Unknown: pEGFP-C1 plasmid
      oligonucleotide

<400> SEQUENCE: 27
gtcgacggta ccgcgggccc gggatcc                                           27

<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtcgacgggg atcc                                                         14

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (19)..(33)

<400> SEQUENCE: 29

```
gcgctaccgc gggccacc atg agc aag ggc gag                                 33
                    Met Ser Lys Gly Glu
                     1               5
```

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Ser Lys Gly Glu

```
<210> SEQ ID NO 31
<211> LENGTH: 36
<212> TYPE: DNA
<213> ORGANISM: Aequorea victoria
<220> FEATURE:
<221> NAME/KEY: CDS
<222> LOCATION: (19)..(36)

<400> SEQUENCE: 31
gcgctaccgg tcgccacc atg gtg agc aag ggc gag                    36
                    Met Val Ser Lys Gly Glu
                     1               5

<210> SEQ ID NO 32
<211> LENGTH: 6
<212> TYPE: PRT
<213> ORGANISM: Aequorea victoria

<400> SEQUENCE: 32

Met Val Ser Lys Gly Glu
 1               5

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (3)..(20)

<400> SEQUENCE: 33 gc atc aag gcc aac ttc aag                                      20
   Ile Lys Ala Asn Phe Lys
    1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Lys Ala Asn Phe Lys
 1               5

<210> SEQ ID NO 35
<211> LENGTH: 20
<212> TYPE: DNA
<213> ORGANISM: Aequorea victoria
<220> FEATURE:
<221> NAME/KEY: CDS
<222> LOCATION: (3)..(20)

<400> SEQUENCE: 35 gc atc aag gtg aac ttc aag                                      20
   Ile Lys Val Asn Phe Lys
    1               5

<210> SEQ ID NO 36
<211> LENGTH: 6
<212> TYPE: PRT
```

<213> ORGANISM: Aequorea victoria

<400> SEQUENCE: 36

Ile Lys Val Asn Phe Lys
1               5

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (3)..(17)

<400> SEQUENCE: 37 gg atc act cac ggc atg ga                                          19
   Ile Thr His Gly Met
   1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Thr His Gly Met
1               5

<210> SEQ ID NO 39
<211> LENGTH: 19
<212> TYPE: DNA
<213> ORGANISM: Aequorea victoria
<220> FEATURE:
<221> NAME/KEY: CDS
<222> LOCATION: (3)..(17)

<400> SEQUENCE: 39 gg atc act ctc ggc atg ga                                          19
   Ile Thr Leu Gly Met
   1               5

<210> SEQ ID NO 40
<211> LENGTH: 5
<212> TYPE: PRT
<213> ORGANISM: Aequorea victoria

<400> SEQUENCE: 40

Ile Thr Leu Gly Met
1               5

<210> SEQ ID NO 41
<211> LENGTH: 596
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
agcttcagat ctgtcaaact tacatcagac ttcgacaacc caagatggat tggacgacac      60
aagcatatgt tcaatttcct tgatgtcaac cacaatggaa aaatctctct tgacgagatg     120

```
gtctacaagg catctgatat tgtcatcaat aaccttggag caacacctga gcaagccaaa      180
cgacacaaag atgctgtgga agccttcttc ggaggagctg gaatgaaata tggtgtggaa      240
actgattggc ctgcatatat tgaaggatgg aaaaaattgg ctactgatga attggagaaa      300
tacgccaaaa acgaaccaac cctcatccgc atctggggtg atgctttgtt tgatatcgtt      360
gacaaagatc aaaatggagc tattacactg gatgaatgga agcatacac caaagctgct       420 ggtatcatcc aatcatcaga agattgcgag gaaacattca gagtgtgcga tattgatgaa      480
agtggacaac tcgatgttga tgagatgaca agacagcatc tgggattttg gtacaccatg      540
gatcctgctt gcgaaaagct ctacggtgga gctgtcccct aatctcgagg atcttt         596
```

```
<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(21)

<400> SEQUENCE: 42 aag tcc gga ctc aga tct gtc                                            21
Lys Ser Gly Leu Arg Ser Val
1               5
```

```
<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Ser Gly Leu Arg Ser Val
1               5
```

```
<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gacagatctg agtccggact t                                                21
```

```
<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aagtgcggac tcagatctgt c                                                21
```

```
<210> SEQ ID NO 46
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 46
ccggcgggag cggatccggc ggccagt                                        27

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly Ser Gly Ser Gly Gly Gln Ser
1               5

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccggactggc cgccggatcc gctcccg                                        27

<210> SEQ ID NO 49
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gtcgacggta c                                                         11

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 50 tcc gga ctc aga tct                                                  15
Ser Gly Leu Arg Ser
1               5

<210> SEQ ID NO 51
<211> LENGTH: 150
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(150)
<220> FEATURE:
```

```
-continued

<221> NAME/KEY: MISC_FEATURE
<222> LOCATION: (1)..(135)
<223> OTHER INFORMATION: This region may encompass 1 to 5 repeating
      units

<400> SEQUENCE: 51 tcc ggc ggg agc gga tcc ggc ggc cag tcc ggc ggg agc gga tcc ggc        48
Ser Gly Gly Ser Gly Ser Gly Gly Gln Ser Gly Gly Ser Gly Ser Gly
1               5                   10                  15 ggc cag tcc ggc ggg agc gga tcc ggc ggc cag tcc ggc ggg agc gga        96
Gly Gln Ser Gly Gly Ser Gly Ser Gly Gly Gln Ser Gly Gly Ser Gly
            20                  25                  30 tcc ggc ggc cag tcc ggc ggg agc gga tcc ggc ggc cag tcc gga ctc        144
Ser Gly Gly Gln Ser Gly Gly Ser Gly Ser Gly Gly Gln Ser Gly Leu
        35                  40                  45 aga tct                                                                 150
Arg Ser
    50

<210> SEQ ID NO 52
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(45)
<223> OTHER INFORMATION: This region may encompass 1 to 5 repeating
      units

<400> SEQUENCE: 52

Ser Gly Gly Ser Gly Ser Gly Gly Gln Ser Gly Gly Ser Gly Ser Gly
1               5                   10                  15

Gly Gln Ser Gly Gly Ser Gly Ser Gly Gly Gln Ser Gly Gly Ser Gly
            20                  25                  30

Ser Gly Gly Gln Ser Gly Gly Ser Gly Ser Gly Gly Gln Ser Gly Leu
        35                  40                  45

Arg Ser
    50
```